(12) United States Patent
Akino et al.

(10) Patent No.: US 8,608,986 B2
(45) Date of Patent: Dec. 17, 2013

(54) METAL COMPLEX, POLYMER COMPOUND AND DEVICE CONTAINING THOSE

(75) Inventors: Nobuhiko Akino, Tsukuba (JP); Rei Okamura, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 532 days.

(21) Appl. No.: 12/520,302

(22) PCT Filed: Dec. 27, 2007

(86) PCT No.: PCT/JP2007/075069
§ 371 (c)(1),
(2), (4) Date: Sep. 23, 2009

(87) PCT Pub. No.: WO2008/078800
PCT Pub. Date: Jul. 3, 2008

(65) Prior Publication Data
US 2010/0019669 A1    Jan. 28, 2010

(30) Foreign Application Priority Data

Dec. 27, 2006   (JP) .................................. 2006-351846

(51) Int. Cl.
*H01B 1/22* (2006.01)
(52) U.S. Cl.
USPC ............. 252/519.13; 252/519.2; 252/301.16; 528/9; 546/4
(58) Field of Classification Search
USPC ................. 252/519.13, 519.2, 301.16; 528/9; 546/4
See application file for complete search history.

(56) References Cited

U.S. PATENT DOCUMENTS

| | | | |
|---|---|---|---|
| 5,247,190 A | 9/1993 | Friend et al. | |
| 5,707,745 A | 1/1998 | Forrest et al. | |
| 7,011,897 B2 | 3/2006 | Thompson et al. | |
| 8,420,229 B2 * | 4/2013 | Begley et al. | 428/690 |
| 2004/0121184 A1 * | 6/2004 | Thompson et al. | 428/690 |
| 2004/0138455 A1 * | 7/2004 | Stossel et al. | 546/2 |
| 2006/0208222 A1 * | 9/2006 | Ise | 252/301.16 |
| 2006/0246315 A1 * | 11/2006 | Begley et al. | 428/690 |
| 2007/0003789 A1 | 1/2007 | Kwong et al. | |
| 2007/0196689 A1 | 8/2007 | Ragini et al. | |
| 2011/0114890 A1 * | 5/2011 | Asada et al. | 252/301.35 |
| 2011/0124808 A1 * | 5/2011 | Akino et al. | 524/610 |
| 2011/0210322 A1 * | 9/2011 | Ishii et al. | 257/40 |

FOREIGN PATENT DOCUMENTS

| | | |
|---|---|---|
| CN | 1681904 A | 10/2005 |
| JP | 2003109758 A | 4/2003 |
| JP | 2006-513278 A | 4/2006 |
| JP | 2006-188673 A | 7/2006 |
| WO | 2006014599 A2 | 2/2006 |

OTHER PUBLICATIONS

Office Action issued Aug. 25, 2011 in Chinese Patent Application No. 2011082200646000 with English translation.
M.A. Baldo et al., "Very high-efficiency green organic light-emitting devices based on electrophosphorescence", Applied Physics Letters, vol. 75, No. 1, Jul. 5, 1999, pp. 4-6.
Wai-Yeung Wong, et al., "A Multifunctional Platinum-Based Triplet Emitter for OLED Applications", Organometallics, 2005, 24, pp. 4079-4082.
Taiwanese Office Action in Taiwanese Application No. 096150459 dated Mar. 20, 2013.
European Patent Office, "Communication Pursuant to Rule 114(2) EPC," issued in connection with European Patent Application No. 07860291.9, dated Nov. 13, 2012.
Constable et al., "Metallostars containing {Ru(bpy)$_3$} motifs," pp. 158-168, Inorganica Chimica Acta 300-302, 2000.
Japanese Patent Office, "Notice of Reasons for Rejection," issued in connection with Japanese Patent Application No. 2007-329887, dated Dec. 25, 2012.
European Patent Office, "Communication Under Rule 71(3) EPC," issued in connection with European Patent Application No. 07 860 291.9, dated Jul. 5, 2013.

* cited by examiner

*Primary Examiner* — Douglas McGinty
(74) *Attorney, Agent, or Firm* — Sughrue Mion, PLLC

(57) ABSTRACT

Disclosed is a metal complex represented by the following formula (1).

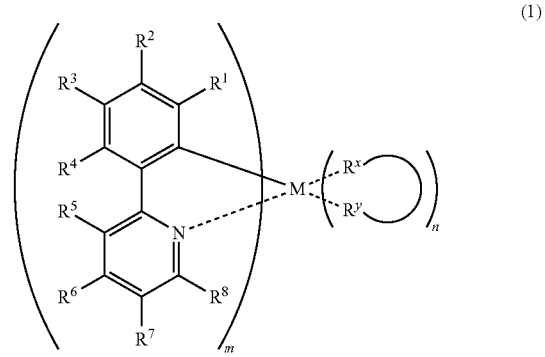

(1)

In the formula, M represents a metal atom; $R^1$-$R^8$ respectively represent a hydrogen atom, a halogen atom or a monovalent group; or alternatively $R^3$ and $R^4$, or $R^5$ and $R^6$ may combine together to form a ring.

25 Claims, No Drawings

METAL COMPLEX, POLYMER COMPOUND AND DEVICE CONTAINING THOSE

TECHNICAL FIELD

The present invention relates to a metal complex and a polymer compound containing a residue of the metal complex. The present invention also relates to a device containing those.

BACKGROUND ART

A metal complex that exhibits light emission from a triplet excited state can be expected as a light-emitting material used in a light-emitting layer in electroluminescent devices to have higher luminous efficiency than that of a fluorescent material which exhibits light emission from a singlet excited state. For example, an ortho-metalated complex having iridium as a central metal (Ir(ppy)$_3$: Tris-Ortho-Metalated Complex of Iridium(III) with 2-Phenylpyridine), which exhibits green light emission, has been proposed (NON-PATENT DOCUMENT 1) as the metal complex which exhibits light emission from a triplet excited state.

NON-PATENT DOCUMENT 1: APPLIED PHYSICS LETTERS, Vol. 75, p. 4 (1999)

DISCLOSURE OF THE INVENTION

Problems to be Solved by the Invention

However, when the metal complex described above was used in the production of electroluminescent devices or the like, the obtained devices were not excellent in luminous efficiency.

Thus, an object of the present invention is to provide a metal complex, etc., that gives devices excellent in luminous efficiency, when used in the production of electroluminescent devices or the like.

Means for Solving the Problems

A first aspect of the present invention provides a metal complex represented by the following formula (1):

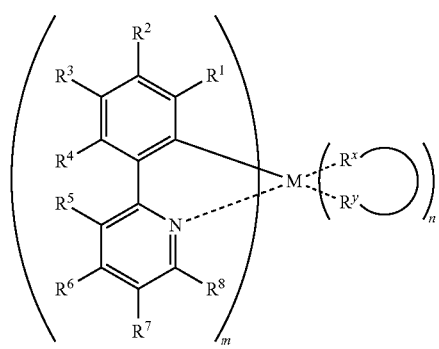

(1)

wherein M is a metal atom of ruthenium, rhodium, palladium, osmium, iridium or platinum; $R^1$ to $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, or $R^3$ and $R^4$ or $R^5$ and $R^6$ may bond to form a ring, provided that at least one of $R^2$ and $R^7$ is a group represented by the following formula (2):

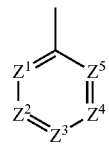

(2)

wherein m is an integer of 1 to 3, and n is an integer of 0 to 2; $Z^1$ to $Z^5$ each independently represent a carbon atom or a nitrogen atom, provided that at least two of $Z^1$ to $Z^5$ are a nitrogen atom, and when any of $Z^1$ to $Z^5$ is a carbon atom, a hydrogen atom bonded to the carbon atom may be substituted by a substituent; the moiety represented by the following formula (3):

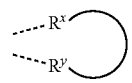

(3)

represents a monoanionic bidentate ligand; and $R^x$ and $R^y$ are an atom bonded to the metal atom M and each independently represent a carbon atom, an oxygen atom or a nitrogen atom.

A second aspect of the present invention provides a method for producing the metal complex, comprising performing a coupling reaction between a heterocyclic aromatic compound having a halogen atom or an alkyl sulfonate group and a compound represented by any of the following formulas (A-1) to (A-3):

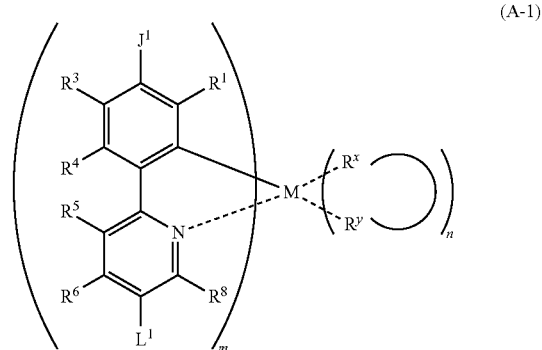

(A-1)

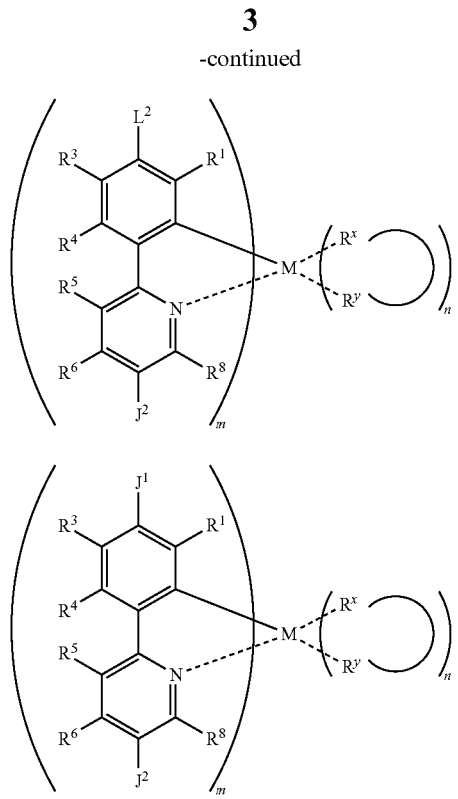

wherein M represents any metal atom of ruthenium, rhodium, palladium, osmium, iridium and platinum; $R^1$, $R^3$, $R^4$, $R^5$, $R^6$, $R^8$, $L^1$ and $L^2$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, or $R^3$ and $R^4$ or $R^5$ and $R^6$ may form a ring through a bond therebetween; m is an integer of 1 to 3, and n is an integer of 0 to 2; the moiety represented by the following formula (3):

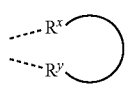 (3)

represents a monoanionic bidentate ligand; $R^x$ and $R^y$ are an atom bonded to the metal atom M and each independently represent a carbon atom, an oxygen atom or a nitrogen atom; and $J^1$ and $J^2$ are each independently a group represented by the following formulas (B-1) to (B-6):

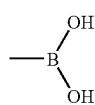 (B-1)

 (B-2)

 (B-3)

 (B-4)

 (B-5)

 (B-6)

A third aspect of the present invention provides compounds represented by the formulas (A-1) to (A-3).

A fourth aspect of the present invention provides a polymer compound containing a residue of the metal complex.

A fifth aspect of the present invention provides a composition containing the metal complex and/or the polymer compound and a charge transport material and/or a light-emitting material.

A sixth aspect of the present invention provides a liquid composition containing the metal complex and/or the polymer compound and a solvent or a dispersion medium.

A seventh aspect of the present invention provides a film containing the metal complex and/or the polymer compound.

An eighth aspect of the present invention provides a device containing the metal complex and/or the polymer compound.

A ninth aspect of the present invention provides a planar light source and illumination which are obtained using the device.

Advantages of the Invention

A metal complex, etc., of the present invention gives devices excellent in luminous efficiency (i.e., having a high quantum yield), when used in the production of electroluminescent devices or the like. Moreover, the metal complex, etc., of the present invention usually emits light. Thus, the metal complex, etc., of the present invention is particularly useful in the production of devices such as light-emitting devices (e.g., electroluminescent devices) and photoelectric devices.

BEST MODE FOR CARRYING OUT THE INVENTION

Hereinafter, the present invention will be described in detail.

<Metal Complex>

First, a metal complex of the present invention will be described.

The metal complex of the present invention is represented by the formula (1).

In the substituent represented by the formula (2), at least two, preferably two or three, of $Z^1$ to $Z^5$ are a nitrogen atom. Particularly, it is preferred that these moieties should make a combination such that these plural nitrogen atoms are not adjacent (i.e., not located in vicinal positions). Specifically, two or three of $Z^1$ to $Z^5$ are a nitrogen atom, and these nitrogen atoms are not adjacent. When any of $Z^1$ to $Z^5$ in the substituent is a carbon atom, a hydrogen atom bonded to the carbon atom may be substituted by a substituent.

The specific structure of the substituent represented by formula (2) is exemplified by structures shown below. Among them, those represented by the formulas (4-1) and (4-7) are preferable.

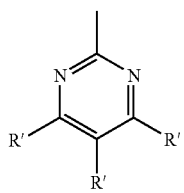
(4-1)

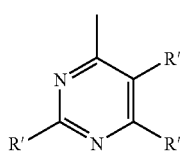
(4-2)

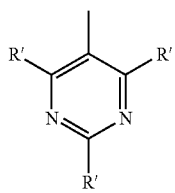
(4-3)

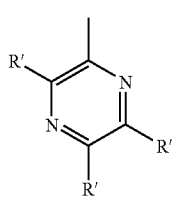
(4-4)

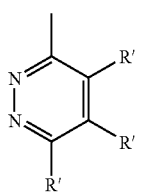
(4-5)

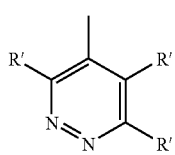
(4-6)

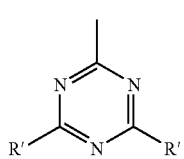
(4-7)

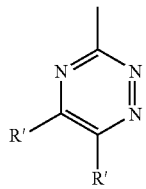
(4-8)

wherein R' is a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, and plural R' may be the same or different.

In the formula, the halogen atom, the alkyl group, the alkoxy group, the alkylthio group, the aryl group, the aryloxy group, the arylthio group, the arylalkyl group, the arylalkoxy group, the arylalkylthio group, the acyl group, the acyloxy group, the amide group, the acid imide group, the imine residue, the substituted amino group, the substituted silyl group, the substituted silyloxy group, the substituted silylthio group, the substituted silylamino group, the monovalent heterocyclic group, the heteroaryloxy group, the heteroarylthio group, the arylalkenyl group, the arylalkynyl group, the substituted carboxyl group and the cyano group represented by R' have the same definition and specific examples as those represented by R described later.

The metal complex represented by the formula (1) comprises a metal atom represented by M, a ligand whose number is defined by a subscript m (hereinafter, also referred to as a "bidentate chelating ligand"), and a monoanionic bidentate ligand represented by the formula (3) whose number is defined by a subscript n (hereinafter, also referred to as a "monoanionic bidentate ligand"). In this context, simply the "ligand" in description below means both of the bidentate chelating ligand and the monoanionic bidentate ligand.

In the formula (1), m is an integer of 1 to 3, and n is an integer of 0 to 2, preferably, 0 or 1, more preferably 0, provided that m+n is the total number of the ligands capable of binding to the central metal M; e.g., m=1 and n=2, m=2 and n=1 or m=3 and n=0, preferably m=3 and n=0 or m=2 and n=1, more preferably m=3 and n=0, when the central metal is iridium.

The metal complex represented by the formula (1) is preferably represented by the following formula (1a):

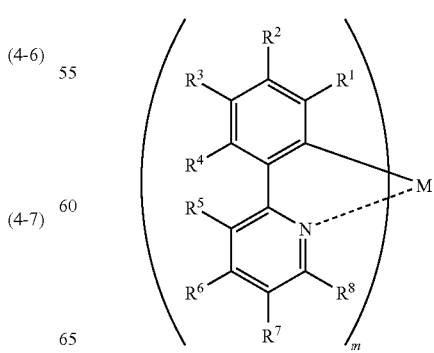
(1a)

wherein M, R¹ to R⁸ and m are as defined above (i.e., n=0). The atoms or the groups represented by R¹ to R⁸ are specifically the same as those described and exemplified as R described later.

The ligand constituting the metal complex influences the emitted light color, emission intensity, luminous efficiency, and so on of the metal complex. Thus, it is preferred that the metal complex should comprise a ligand having a structure that minimizes an energy deactivation process within the ligand. Furthermore, the type and/or substitution position of the substituent in the ligand influence the electronic properties of the ligand and therefore influence the properties of the metal complex. From these points of view, the structure of the metal complex of the present invention represented by the formula (1) can presumably achieve improvement in the luminous efficiency, stability, and so on, of the metal complex.

In the metal complex of the present invention, at least one of R² and R⁷ in the formula (1) or (1a) is a group represented by the formula (2). It is preferred that the R⁷ should be a group represented by the formula (2). Moreover, it is also preferred that the metal complex of the present invention should have a structure wherein the R² and the R⁷ are each independently a group represented by the formula (2). It is more preferred that the R⁷ should be represented by the formula (4-1) and the R² should be a hydrogen atom, that the R⁷ should be represented by the formula (4-7) and the R² should be a hydrogen atom, or that the R² and the R⁷ should each independently be a group represented by the formula (4-1) or (4-7). The metal complex of the present invention has a peak wavelength of preferably 550 nm to 800 nm, more preferably 570 nm to 750 nm, even more preferably 570 nm to 700 nm, particularly preferably 600 nm to 700 nm, in a PL (photoluminescence) emission spectrum (phosphorescence emission spectrum).

The metal atom M that serves as a central metal in the metal complex of the present invention is any metal atom of ruthenium, rhodium, palladium, osmium, iridium or platinum. These metal atoms are capable of causing spin-orbit interaction in the metal complex and causing intersystem crossing between singlet and triplet states. The metal atom M is preferably osmium, iridium or platinum, more preferably iridium or platinum, particularly preferably iridium.

In the metal complex represented by the formula (1) or (1a), specific examples of the bidentate chelating ligand include structures as represented by the following formulas:

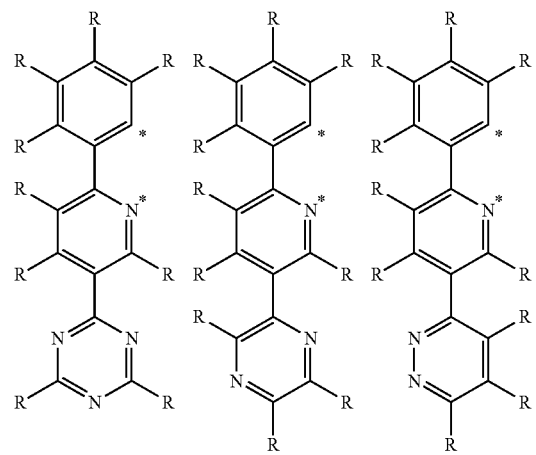

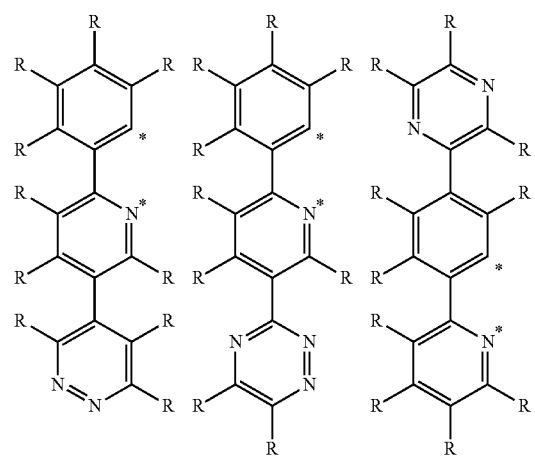

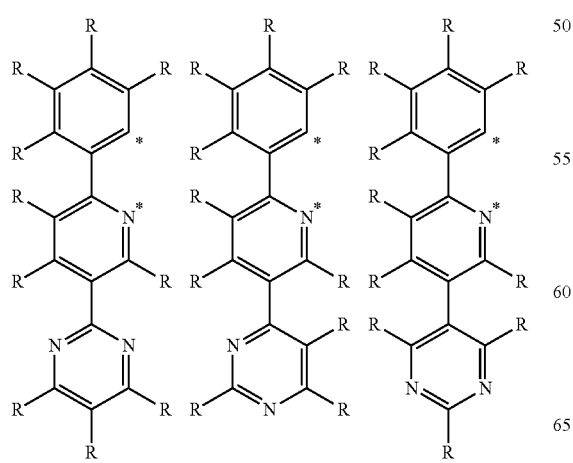

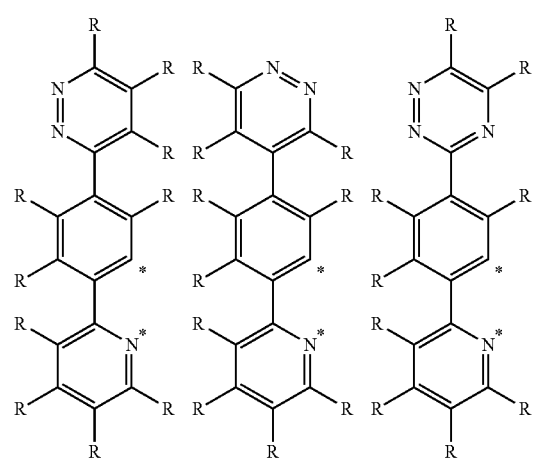

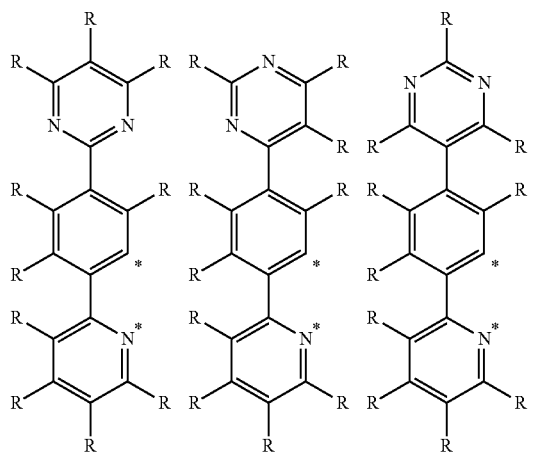

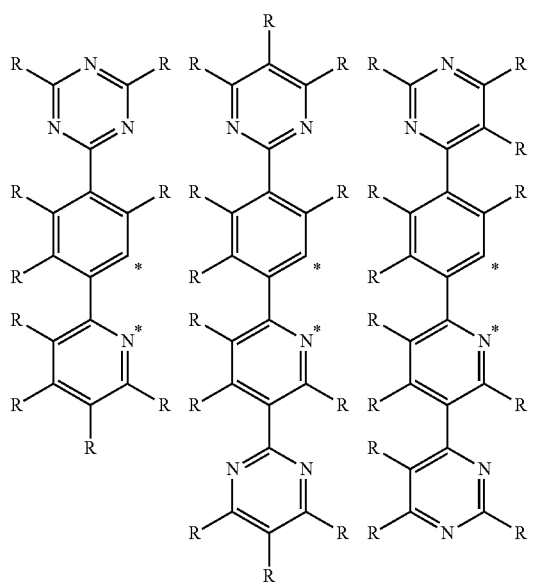

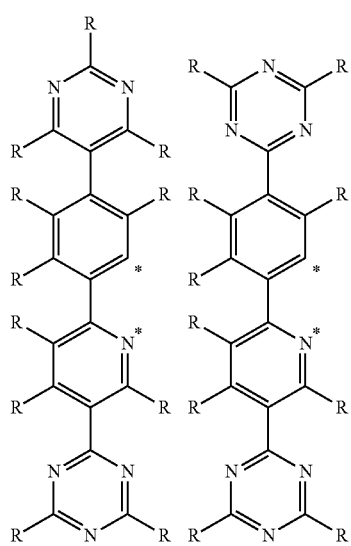

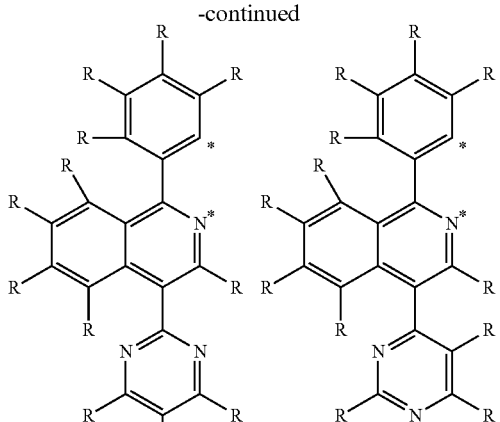

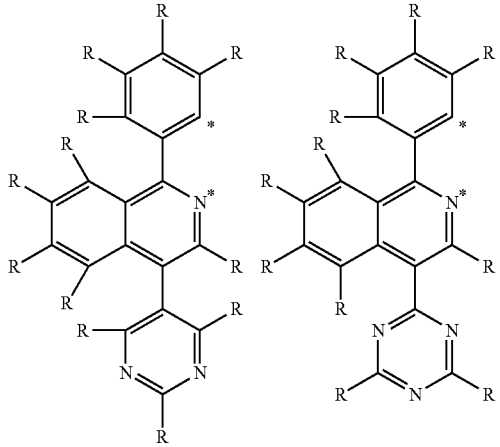

wherein R is a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group; * represents a site bonded to the metal atom M; and plural R may be the same or different.

The halogen atom represented by R is exemplified by fluorine, chlorine, bromine and iodine atoms.

The alkyl group represented by R may be linear, branched or cyclic. This alkyl group usually has approximately 1 to 10 carbon atoms. Specific examples of the alkyl group include methyl, ethyl, propyl, isopropyl, butyl, isobutyl, t-butyl, pentyl, hexyl, cyclohexyl, heptyl, octyl, 2-ethylhexyl, nonyl, decyl, 3,7-dimethyloctyl, lauryl, trifluoromethyl, pentafluoroethyl, perfluorobutyl, perfluorohexyl and perfluorooctyl groups. t-butyl, pentyl, hexyl, octyl, 2-ethylhexyl, decyl and 3,7-dimethyloctyl groups are preferable.

The alkoxy group represented by R may be linear, branched or cyclic. This alkoxy group usually has approximately 1 to 10 carbon atoms. Specific examples of the alkoxy group include methoxy, ethoxy, propyloxy, isopropyloxy, butoxy, isobutoxy, t-butoxy, pentyloxy, hexyloxy, cyclohexyloxy, heptyloxy, octyloxy, 2-ethylhexyloxy, nonyloxy, decyloxy, 3,7-dimethyloctyloxy, lauryloxy, trifluoromethoxy, pentafluoroethoxy, perfluorobutoxy, perfluorohexyl, perfluorooctyl, methoxymethyloxy and 2-methoxyethyloxy groups. Pentyloxy, hexyloxy, octyloxy, 2-ethylhexyloxy, decyloxy and 3,7-dimethyloctyloxy groups are preferable.

The alkylthio group represented by R may be linear, branched or cyclic. This alkylthio group usually has approximately 1 to 10 carbon atoms. Specific examples of the alkylthio group include methylthio, ethylthio, propylthio, isopropylthio, butylthio, isobutylthio, t-butylthio, pentylthio, hexylthio, cyclohexylthio, heptylthio, octylthio, 2-ethylhexylthio, nonylthio, decylthio, 3,7-dimethyloctylthio, laurylthio and trifluoromethylthio groups. Pentylthio, hexylthio, octylthio, 2-ethylhexylthio, decylthio and 3,7-dimethyloctylthio groups are preferable.

The aryl group represented by R usually has approximately 6 to 60 carbon atoms, preferably 7 to 48 carbon atoms. The aryl group is exemplified by phenyl, $C_1$ to $C_{12}$ alkoxyphenyl (the term "$C_1$ to $C_{12}$ alkoxy" means that the alkoxy moiety has 1 to 12 carbon atoms; the same holds true for description below), $C_1$ to $C_{12}$ alkylphenyl (the term "$C_1$ to $C_{12}$ alkyl" means that the alkyl moiety has 1 to 12 carbon atoms; the same holds true for description below), 1-naphthyl, 2-naphthyl, 1-anthracenyl, 2-anthracenyl, 9-anthracenyl and pentafluorophenyl groups. $C_1$ to $C_{12}$ alkoxyphenyl and $C_1$ to $C_{12}$ alkylphenyl groups are preferable. In this context, the aryl group refers to an atomic group derived from aromatic hydrocarbon by removal of one hydrogen atom. This aromatic hydrocarbon includes those having a condensed ring and those comprising two or more independent benzene rings or condensed rings bonded directly or via a group such as vinylene. Furthermore, the aryl group may have a substituent. Examples of the substituent include $C_1$ to $C_{12}$ alkoxyphenyl and $C_1$ to $C_{12}$ alkylphenyl groups.

The $C_1$ to $C_{12}$ alkoxy is exemplified by methoxy, ethoxy, propyloxy, isopropyloxy, butoxy, isobutoxy, t-butoxy, pentyloxy, hexyloxy, cyclohexyloxy, heptyloxy, octyloxy, 2-ethylhexyloxy, nonyloxy, decyloxy, 3,7-dimethyloctyloxy and lauryloxy.

The $C_1$ to $C_{12}$ alkylphenyl group is exemplified by methylphenyl, ethylphenyl, dimethylphenyl, propylphenyl, mesityl, methylethylphenyl, isopropylphenyl, butylphenyl, isobutylphenyl, t-butylphenyl, pentylphenyl, isoamylphenyl, hexylphenyl, heptylphenyl, octylphenyl, nonylphenyl, decylphenyl and dodecylphenyl groups.

The aryloxy group represented by R usually has approximately 6 to 60 carbon atoms, preferably 7 to 48 carbon atoms. The aryloxy group is exemplified by phenoxy, $C_1$ to $C_{12}$ alkoxyphenoxy, $C_1$ to $C_{12}$ alkylphenoxy, 1-naphthyloxy, 2-naphthyloxy and pentafluorophenyloxy groups. $C_1$ to $C_{12}$ alkoxyphenoxy and $C_1$ to $C_{12}$ alkylphenoxy groups are preferable.

The $C_1$ to $C_{12}$ alkoxy is exemplified by methoxy, ethoxy, propyloxy, isopropyloxy, butoxy, isobutoxy, t-butoxy, pentyloxy, hexyloxy, cyclohexyloxy, heptyloxy, octyloxy, 2-ethylhexyloxy, nonyloxy, decyloxy, 3,7-dimethyloctyloxy and lauryloxy.

The $C_1$ to $C_{12}$ alkylphenoxy group is exemplified by methylphenoxy, ethylphenoxy, dimethylphenoxy, propylphenoxy, 1,3,5-trimethylphenoxy, methylethylphenoxy, isopropylphenoxy, butylphenoxy, isobutylphenoxy, t-butylphenoxy, pentylphenoxy, isoamylphenoxy, hexylphenoxy, heptylphenoxy, octylphenoxy, nonylphenoxy, decylphenoxy and dodecylphenoxy groups.

The arylthio group usually has approximately 6 to 60 carbon atoms, preferably 7 to 48 carbon atoms. The arylthio group is exemplified by phenylthio, $C_1$ to $C_{12}$ alkoxyphenylthio, $C_1$ to $C_{12}$ alkylphenylthio, 1-naphthylthio, 2-naphthylthio and pentafluorophenylthio groups. $C_1$ to $C_{12}$ alkoxyphenylthio and $C_1$ to $C_{12}$ alkylphenylthio groups are preferable.

The arylalkyl group represented by R usually has approximately 7 to 60 carbon atoms, preferably 7 to 48 carbon atoms. The arylalkyl group is exemplified by phenyl-$C_1$ to $C_{12}$ alkyl, $C_1$ to $C_{12}$ alkoxyphenyl-$C_1$ to $C_{12}$ alkyl, $C_1$ to $C_{12}$-alkylphenyl-$C_1$ to $C_{12}$ alkyl, 1-naphthyl-$C_1$ to $C_{12}$ alkyl and 2-naphthyl-$C_1$ to $C_{12}$ alkyl groups. $C_1$ to $C_{12}$ alkoxyphenyl-$C_1$ to $C_{12}$ alkyl and $C_1$ to $C_{12}$ alkylphenyl-$C_1$ to $C_{12}$ alkyl groups are preferable.

The arylalkoxy group represented by R usually has approximately 7 to 60 carbon atoms, preferably 7 to 48 carbon atoms. The arylalkoxy group is exemplified by phenyl-$C_1$ to $C_{12}$ alkoxy (e.g., phenylmethoxy, phenylethoxy, phenylbutoxy, phenylpentyloxy, phenylhexyloxy, phenylheptyloxy and phenyloctyloxy), $C_1$ to $C_{12}$ alkoxyphenyl-$C_1$ to $C_{12}$ alkoxy, $C_1$ to $C_{12}$ alkylphenyl-$C_1$ to $C_{12}$ alkoxy, 1-naphthyl-$C_1$ to $C_{12}$ alkoxy and 2-naphthyl-$C_1$ to $C_{12}$ alkoxy groups. $C_1$ to $C_{12}$ alkoxyphenyl-$C_1$ to $C_{12}$ alkoxy and $C_1$ to $C_{12}$ alkylphenyl-$C_1$ to $C_{12}$ alkoxy groups are preferable.

The arylalkylthio group represented by R usually has approximately 7 to 60 carbon atoms, preferably 7 to 48 carbon atoms. The arylalkylthio group is exemplified by phenyl-$C_1$ to $C_{12}$ alkylthio, $C_1$ to $C_{12}$ alkoxyphenyl-$C_1$ to $C_{12}$ alkylthio, $C_1$ to $C_{12}$ alkylphenyl-$C_1$ to $C_{12}$ alkylthio, 1-naphthyl-$C_1$ to $C_{12}$ alkylthio and 2-naphthyl-$C_1$ to $C_{12}$ alkylthio groups. $C_1$ to $C_{12}$ alkoxyphenyl-$C_1$ to $C_{12}$ alkylthio and $C_1$ to $C_{12}$ alkylphenyl-$C_1$ to $C_{12}$ alkylthio groups are preferable.

The acyl group represented by R usually has approximately 2 to 20 carbon atoms, preferably 2 to 18 carbon atoms. The acyl group is exemplified by acetyl, propionyl, butyryl, isobutyryl, pivaloyl, benzoyl, trifluoroacetyl and pentafluorobenzoyl groups.

The acyloxy group represented by R usually has approximately 2 to 20 carbon atoms, preferably 2 to 18 carbon atoms. The acyloxy group is exemplified by acetoxy, propionyloxy, butyryloxy, isobutyryloxy, pivaloyloxy, benzoyloxy, trifluoroacetyloxy and pentafluorobenzoyloxy groups.

The amide group represented by R usually has approximately 2 to 20 carbon atoms, preferably 2 to 18 carbon atoms. The amide group is exemplified by formamide, acetamide, propionamide, butylamide, benzamide, trifluoroacetamide, pentafluorobenzamide, diformamide, diacetamide, dipropionamide, dibutylamide, dibenzamide, ditrifluoroacetamide and dipentafluorobenzamide groups.

The acid imide group represented by R means a monovalent residue derived from acid imide by removal of one hydrogen atom bonded to the nitrogen atom. This acid imide group usually has approximately 2 to 60 carbon atoms, preferably 2 to 48 carbon atoms. The acid imide group is exemplified by groups represented by the following structural formulas:

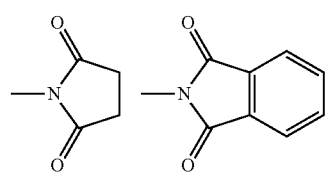

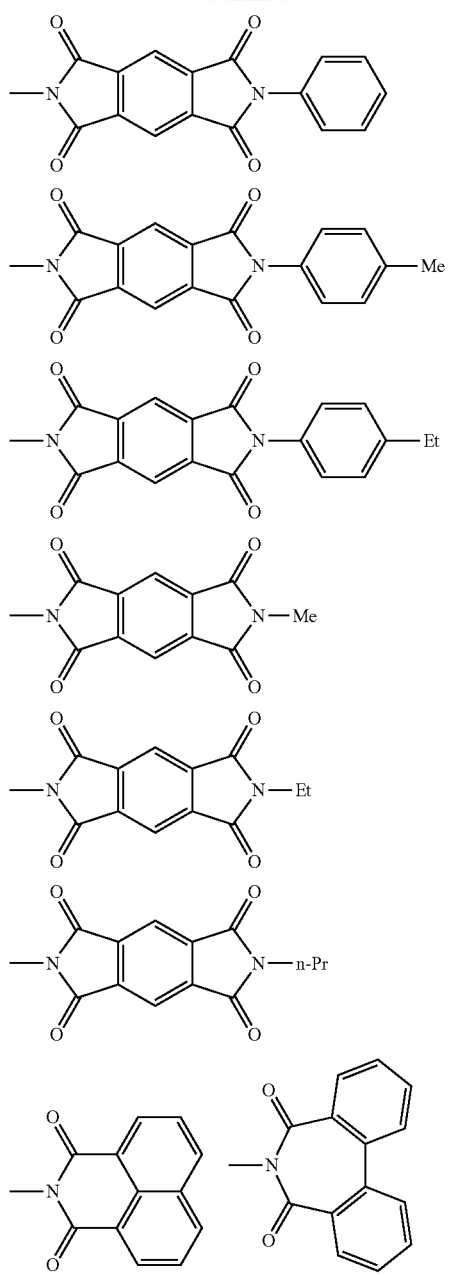

wherein a line coming from the nitrogen atom represents a bond; Me represents a methyl group; Et represents an ethyl group; and n-Pr represents an n-propyl group; the same holds true for description below.

The imine residue represented by R means a monovalent residue derived from an imine compound (i.e., an organic compound having —N═C— in the molecule; examples thereof include aldimine, ketimine, and compounds having an alkyl group or the like substituted for a hydrogen atom bonded to a nitrogen atom in these molecules) by removal of one hydrogen atom. This imine residue usually has approximately 2 to 20 carbon atoms, preferably 2 to 18 carbon atoms. Specifically, the imine residue is exemplified by groups represented by the following structural formulas:

wherein i-Pr represents an isopropyl group; n-Bu represents an n-butyl group; t-Bu represents a t-butyl group; and a bond represented by the wavy line means a "wedge-shaped bond" and/or a "dashed bond", and in this context, the "wedge-shaped bond" means a bond that extends toward the viewer, while the "dashed bond" means a bond that extends away from the viewer.

The substituted amino group represented by R means an amino group substituted by one or two groups selected from the group consisting of an alkyl group, an aryl group, an arylalkyl group and a monovalent heterocyclic group. The alkyl group, the aryl group, the arylalkyl group or the monovalent heterocyclic group may have a substituent. The substituted amino group usually has approximately 1 to 60 carbon atoms, preferably 2 to 48 carbon atoms, exclusive of the carbon number of the substituent. The substituted amino group is exemplified by methylamino, dimethylamino, ethylamino, diethylamino, propylamino, dipropylamino, isopropylamino, diisopropylamino, butylamino, isobutylamino, t-butylamino, pentylamino, hexylamino, cyclohexylamino, heptylamino, octylamino, 2-ethylhexylamino, nonylamino, decylamino, 3,7-dimethyloctylamino, laurylamino, cyclopentylamino, dicyclopentylamino, cyclohexylamino, dicyclohexylamino, pyrrolidyl, piperidyl, ditrifluoromethylamino, phenylamino, diphenylamino, $C_1$ to $C_{12}$ alkoxyphenylamino, di($C_1$ to $C_{12}$ alkoxyphenyl)amino, di($C_1$ to $C_{12}$ alkylphenyl)amino, 1-naphthylamino, 2-naphthylamino, pentafluorophenylamino, pyridylamino, pyridazinylamino, pyrimidylamino, pyrazylamino, triazylamino, phenyl-$C_1$ to $C_{12}$ alkylamino, $C_1$ to $C_{12}$ alkoxyphenyl-$C_1$ to $C_{12}$ alkylamino, $C_1$ to $C_{12}$ alkylphenyl-$C_1$ to $C_{12}$ alkylamino, di($C_1$ to $C_{12}$ alkoxyphenyl-$C_1$ to $C_{12}$ alkyl)amino, di($C_1$ to $C_{12}$ alkylphenyl-$C_1$ to $C_{12}$ alkyl)amino, 1-naphthyl-$C_1$ to $C_{12}$ alkylamino and 2-naphthyl-$C_1$ to $C_{12}$ alkylamino groups.

The substituted silyl group represented by R means a silyl group substituted by one, two or three groups selected from the group consisting of an alkyl group, an aryl group, an arylalkyl group and a monovalent heterocyclic group. The substituted silyl group usually has approximately 1 to 60 carbon atoms, preferably 3 to 48 carbon atoms. In this context, the alkyl group, the aryl group, the arylalkyl group or the monovalent heterocyclic group may have a substituent. The substituted silyl group is exemplified by trimethylsilyl, triethylsilyl, tripropylsilyl, tri-isopropylsilyl, dimethyl-isopropylsilyl, diethyl-isopropylsilyl, t-butylsilyldimethylsilyl, pentyldimethylsilyl, hexyldimethylsilyl, heptyldimethylsilyl, octyldimethylsilyl, 2-ethylhexyl-dimethylsilyl, nonyldimethylsilyl, decyldimethylsilyl, 3,7-dimethyloctyl-dimethylsilyl, lauryldimethylsilyl, phenyl-$C_1$ to $C_{12}$ alkylsilyl, $C_1$ to $C_{12}$ alkoxyphenyl-$C_1$ to $C_{12}$ alkylsilyl, $C_1$ to $C_{12}$ alkylphenyl-$C_1$ to $C_{12}$ alkylsilyl, 1-naphthyl-$C_1$ to $C_{12}$ alkylsilyl, 2-naphthyl-$C_1$ to $C_{12}$ alkylsilyl, phenyl-$C_1$ to $C_{12}$ alkyldimethylsilyl, triphenylsilyl, tri-p-xylylsilyl, tribenzylsilyl, diphenylmethylsilyl, t-butyldiphenylsilyl and dimethylphenylsilyl groups.

The substituted silyloxy group represented by R means a silyloxy group substituted by one, two or three groups selected from the group consisting of an alkoxy group, an aryloxy group, an arylalkoxy group and a monovalent heterocyclic oxy group. The substituted silyloxy group usually has approximately 1 to 60 carbon atoms, preferably 3 to 48 carbon atoms. The alkoxy group, the aryloxy group, the arylalkoxy group and the monovalent heterocyclic oxy group may have a substituent. The substituted silyloxy group is exemplified by trimethylsilyloxy, triethylsilyloxy, tripropylsilyloxy, tri-isopropylsilyloxy, dimethyl-isopropylsilyloxy, diethyl-isopropylsilyloxy, t-butylsilyldimethylsilyl, pentyldimethylsilyloxy, hexyldimethylsilyloxy, heptyldimethylsilyloxy, octyldimethylsilyloxy, 2-ethylhexyl-dimethylsilyloxy, nonyldimethylsilyloxy, decyldimethylsilyloxy, 3,7-dimethyloctyl-dimethylsilyloxy, lauryldimethylsilyloxy, phenyl-$C_1$ to $C_{12}$ alkylsilyloxy, $C_1$ to $C_{12}$ alkoxyphenyl-$C_1$ to $C_{12}$ alkylsilyloxy, $C_1$ to $C_{12}$ alkylphenyl-$C_1$ to $C_{12}$ alkylsilyloxy, 1-naphthyl-$C_1$ to $C_{12}$ alkylsilyloxy, 2-naphthyl-$C_1$ to $C_{12}$ alkylsilyloxy, phenyl-$C_1$ to $C_{12}$ alkyldimethylsilyloxy, triphenylsilyloxy, tri-p-xylylsilyloxy, tribenzylsilyloxy, diphenylmethylsilyloxy, t-butyldiphenylsilyloxy and dimethylphenylsilyloxy groups.

The substituted silylthio group represented by R means a silylthio group substituted by one, two or three groups selected from the group consisting of an alkylthio group, an arylthio group, an arylalkylthio group and a monovalent heterocyclic thio group. The substituted silylthio group usually has approximately 1 to 60 carbon atoms, preferably 3 to 48 carbon atoms. The alkoxy group, the arylthio group, the arylalkylthio group or the monovalent heterocyclic thio group may have a substituent. The substituted silylthio group is exemplified by trimethylsilylthio, triethylsilylthio, tripropylsilylthio, tri-isopropylsilylthio, dimethyl-isopropylsilylthio, diethyl-isopropylsilylthio, t-butylsilyldimethylsilylthio, pentyldimethylsilylthio, hexyldimethylsilylthio, heptyldimethylsilylthio, octyldimethylsilylthio, 2-ethylhexyl-dimethylsilylthio, nonyldimethylsilylthio, decyldimethylsilylthio, 3,7-dimethyloctyl-dimethylsilylthio, lauryldimethylsilylthio, phenyl-$C_1$ to $C_{12}$ alkylsilylthio, $C_1$ to $C_{12}$ alkoxyphenyl-$C_1$ to $C_{12}$ alkylsilylthio, $C_1$ to $C_{12}$ alkylphenyl-$C_1$ to $C_{12}$ alkylsilylthio, 1-naphthyl-$C_1$ to $C_{12}$ alkylsilylthio, 2-naphthyl-$C_1$ to $C_{12}$ alkylsilylthio, phenyl-$C_1$ to $C_{12}$ alkyldimethylsilylthio, triphenylsilylthio, tri-p-xylylsilylthio, tribenzylsilylthio, diphenylmethylsilylthio, t-butyldiphenylsilylthio and dimethylphenylsilylthio groups.

The substituted silylamino group represented by R means a silylamino group substituted by one, two or three groups selected from the group consisting of an alkylamino group, an arylamino group, an arylalkylamino group and a monovalent heterocyclic amino group. The substituted silylamino group usually has approximately 1 to 60 carbon atoms, preferably 3 to 48 carbon atoms. The alkoxy group, the arylamino group, the arylalkylamino group or the monovalent heterocyclic amino group may have a substituent. The substituted silylamino group is exemplified by trimethylsilylamino, triethylsilylamino, tripropylsilylamino, tri-isopropylsilylamino, dimethyl-isopropylsilylamino, diethyl-isopropylsilylamino, t-butylsilyldimethylsilylamino, pentyldimethylsilylamino, hexyldimethylsilylamino, heptyldimethylsilylamino, octyldimethylsilylamino, 2-ethylhexyl-dimethylsilylamino, nonyldimethylsilylamino, decyldimethylsilylamino, 3,7-dimethyloctyl-dimethylsilylamino, lauryldimethylsilylamino, phenyl-$C_1$ to $C_{12}$ alkylsilyloxy group, $C_1$ to $C_{12}$ alkoxyphenyl-$C_1$ to $C_{12}$ alkylsilylamino, $C_1$ to $C_{12}$ alkylphenyl-$C_1$ to $C_{12}$ alkylsilylamino, 1-naphthyl-$C_1$ to $C_{12}$ alkylsilylamino, 2-naphthyl-$C_1$ to $C_{12}$ alkylsilylamino, phenyl-$C_1$ to $C_{12}$ alkyldimethylsilylamino, triphenylsilylamino, tri-p-xylylsilylamino, tribenzylsilylamino, diphenylmethylsilylamino, t-butyldiphenylsilylamino and dimethylphenylsilylamino groups.

The monovalent heterocyclic group represented by R means an atomic group derived from a heterocyclic compound by removal of one hydrogen atom. The monovalent heterocyclic group usually has approximately 3 to 60 carbon atoms, preferably 3 to 20 carbon atoms. In this context, the carbon number of the substituent is excluded from the carbon number of the monovalent heterocyclic group. In this context, the heterocyclic compound refers to, of organic compounds having a cyclic structure, those endocyclically containing not only a carbon atom but also heteroatoms such as oxygen, sulfur, nitrogen, phosphorus and boron as elements constituting the ring. The monovalent heterocyclic group is exemplified by thienyl, $C_1$ to $C_{12}$ alkylthienyl, pyrrolyl, furyl, pyridyl, $C_1$ to $C_{12}$ alkylpyridyl, piperidyl, quinolyl and isoquinolyl groups. Thienyl, $C_1$ to $C_{12}$ alkylthienyl, pyridyl and $C_1$ to $C_{12}$ alkylpyridyl groups are preferable. Moreover, the monovalent heterocyclic group is preferably a monovalent aromatic heterocyclic group.

The heteroaryloxy group represented by R usually has approximately 6 to 60 carbon atoms, preferably 7 to 48 carbon atoms. The heteroaryloxy group is exemplified by thienyl, $C_1$ to $C_{12}$ alkoxythienyl, $C_1$ to $C_{12}$ alkylthienyl, pyridyloxy, pyridyloxy and isoquinolyloxy groups. $C_1$ to $C_{12}$ alkoxypyridyl and $C_1$ to $C_{12}$ alkylpyridyl groups are preferable.

The $C_1$ to $C_{12}$ alkoxy is exemplified by methoxy, ethoxy, propyloxy, isopropyloxy, butoxy, isobutoxy, t-butoxy, pentyloxy, hexyloxy, cyclohexyloxy, heptyloxy, octyloxy, 2-ethylhexyloxy, nonyloxy, decyloxy, 3,7-dimethyloctyloxy and lauryloxy.

The $C_1$ to $C_{12}$ alkylpyridyloxy group is exemplified by methylpyridyloxy, ethylpyridyloxy, dimethylpyridyloxy, propylpyridyloxy, 1,3,5-trimethylpyridyloxy, methylethylpyridyloxy, isopropylpyridyloxy, butylpyridyloxy, isobutylpyridyloxy, t-butylpyridyloxy, pentylpyridyloxy, isoamylpyridyloxy, hexylpyridyloxy, heptylpyridyloxy, octylpyridyloxy, nonylpyridyloxy, decylpyridyloxy and dodecylpyridyloxy groups.

The heteroarylthio group represented by R usually has approximately 6 to 60 carbon atoms, preferably 7 to 48 carbon atoms. The heteroarylthio group is exemplified by pyridylthio, $C_1$ to $C_{12}$ alkoxypyridylthio, $C_1$ to $C_{12}$ alkylpyridylthio and isoquinolylthio groups. $C_1$ to $C_{12}$ alkoxypyridylthio and $C_1$ to $C_{12}$ alkylpyridylthio groups are preferable.

The arylalkenyl group represented by R usually has approximately 8 to 60 carbon atoms, preferably 8 to 48 carbon atoms. The arylalkenyl group is exemplified by phenyl-$C_2$ to $C_{12}$ alkenyl (the term "$C_2$ to $C_{12}$ alkenyl" means that the alkenyl moiety has 2 to 12 carbon atoms; the same holds true for description below), $C_1$ to $C_{12}$ alkoxyphenyl-$C_2$ to $C_{12}$ alkenyl, $C_1$ to $C_{12}$ alkylphenyl-$C_2$ to $C_{12}$ alkenyl, 1-naphthyl-$C_2$ to $C_{12}$ alkenyl and 2-naphthyl-$C_2$ to $C_{12}$ alkenyl groups. $C_1$ to $C_{12}$ alkoxyphenyl-$C_2$ to $C_{12}$ alkenyl and $C_2$ to $C_{12}$ alkylphenyl-$C_1$ to $C_{12}$ alkenyl groups are preferable.

The arylalkynyl group represented by R usually has approximately 8 to 60 carbon atoms, preferably 8 to 48 carbon atoms. The arylalkynyl group is exemplified by phenyl-$C_2$ to $C_{12}$ alkynyl (the term "$C_2$ to $C_{12}$ alkynyl" means that the alkynyl moiety has 2 to 12 carbon atoms; the same holds true for description below), $C_1$ to $C_{12}$ alkoxyphenyl-$C_2$ to $C_{12}$ alkynyl, $C_1$ to $C_{12}$ alkylphenyl-$C_2$ to $C_{12}$ alkynyl, 1-naphthyl-$C_2$ to $C_{12}$ alkynyl and 2-naphthyl-$C_2$ to $C_{12}$ alkynyl groups. $C_1$ to $C_{12}$ alkoxyphenyl-$C_2$ to $C_{12}$ alkynyl and $C_1$ to $C_{12}$ alkylphenyl-$C_2$ to $C_{12}$ alkynyl groups are preferable.

The substituted carboxyl group represented by R usually means a carboxyl group that has approximately 2 to 60 carbon atoms, preferably 2 to 48 carbon atoms and is substituted by an alkyl group, an aryl group, an arylalkyl group or a monovalent heterocyclic group. Examples of the substituted carboxyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, cyclohexyloxycarbonyl, heptyloxycarbonyl, octyloxycarbonyl, 2-ethylhexyloxycarbonyl, nonyloxycarbonyl, decyloxycarbonyl, 3,7-dimethyloctyloxycarbonyl, dodecyloxycarbonyl, trifluoromethoxycarbonyl, pentafluoroethoxycarbonyl, perfluorobutoxycarbonyl, perfluorohexyloxycarbonyl, perfluorooctyloxycarbonyl, pyridyloxycarbonyl, naphthoxycarbonyl and pyridyloxycarbonyl groups. The alkyl group, the aryl group, the arylalkyl group or the monovalent heterocyclic group may have a substituent. The carbon number of the substituent is excluded from the carbon number of the substituted carboxyl group.

In the formula (3), it is preferred that the arc-shaped moiety that connects Rx and Ry should be a divalent group having 3 to 30 atoms except for a hydrogen atom. The monoanionic bidentate ligand is not particularly limited as long as it is a monoanionic bidentate ligand. Examples thereof include the following structures:

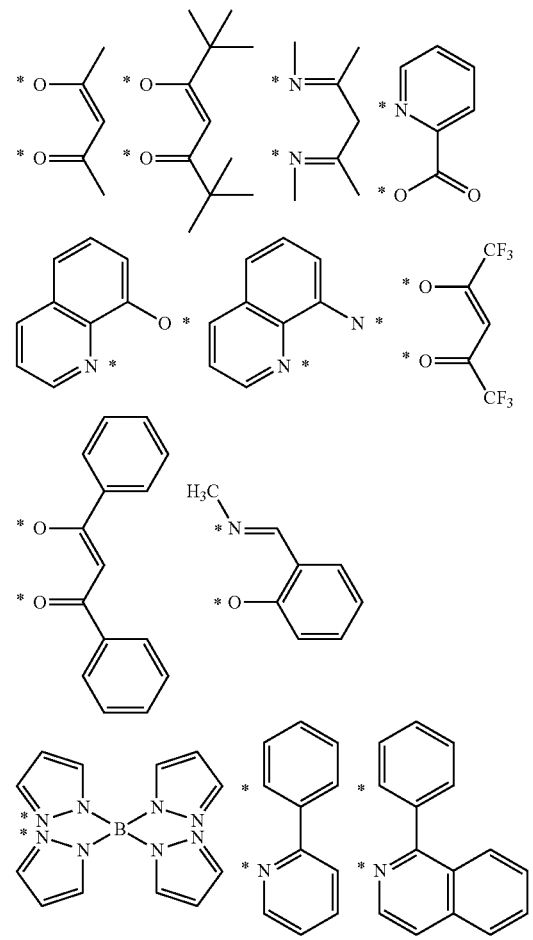

wherein * represents a site bonded to the metal atom M.

Examples of the metal complex of the present invention include the followings:

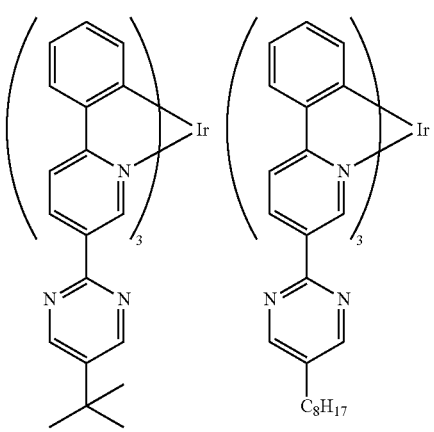

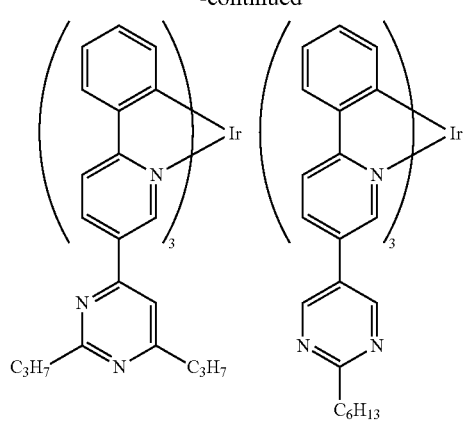
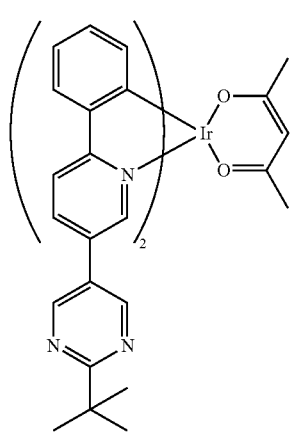
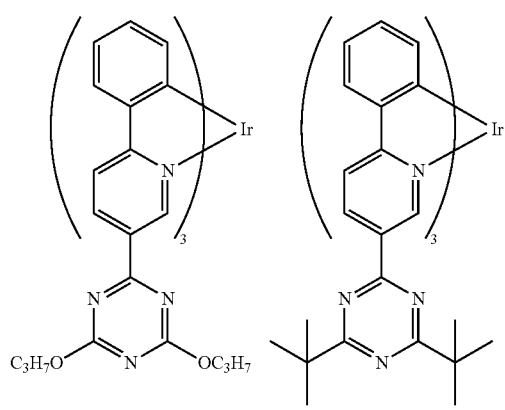
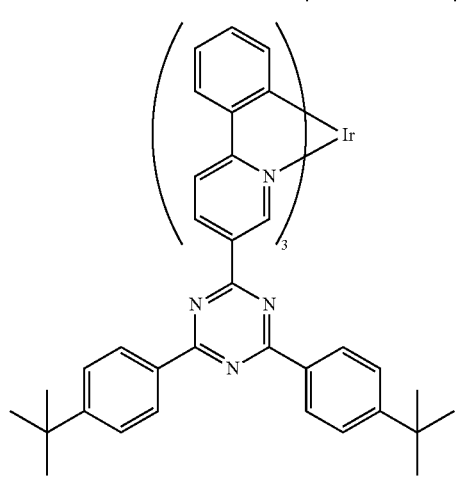
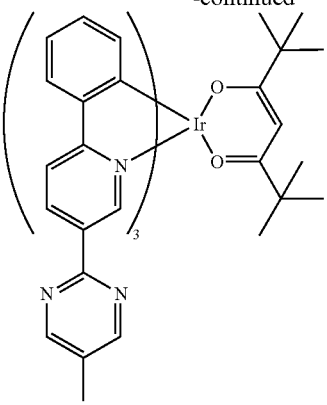
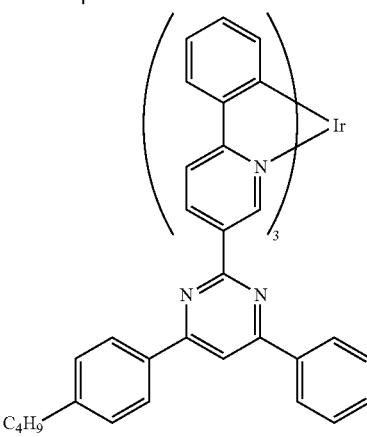
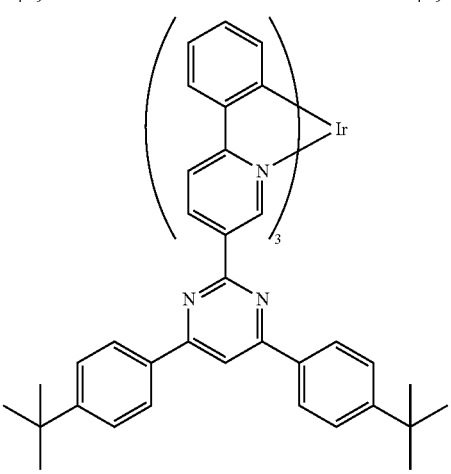
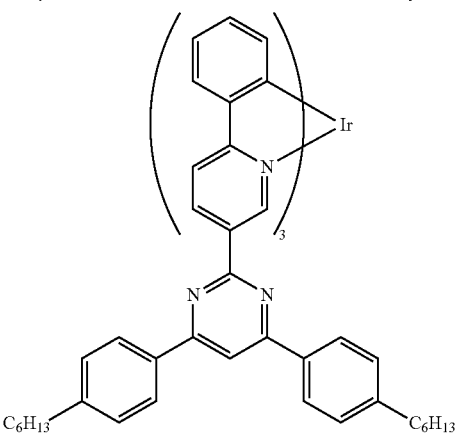

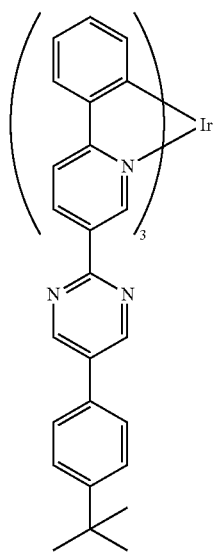
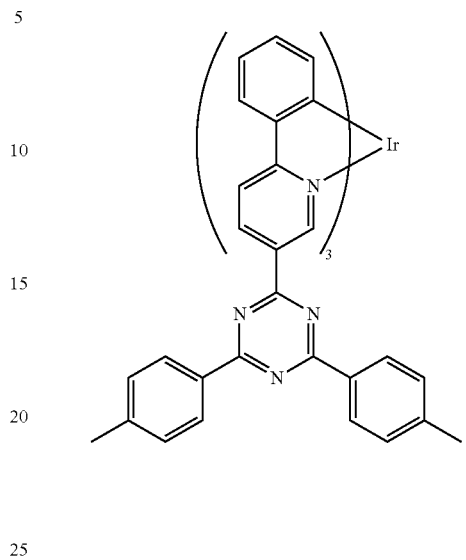
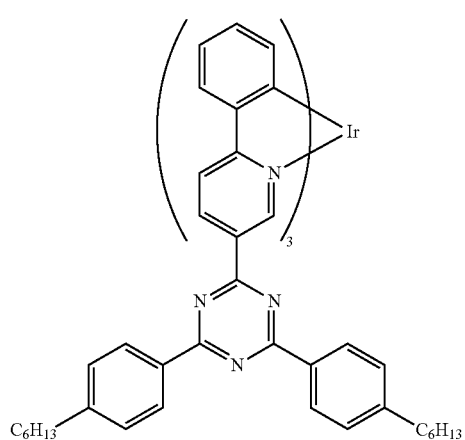
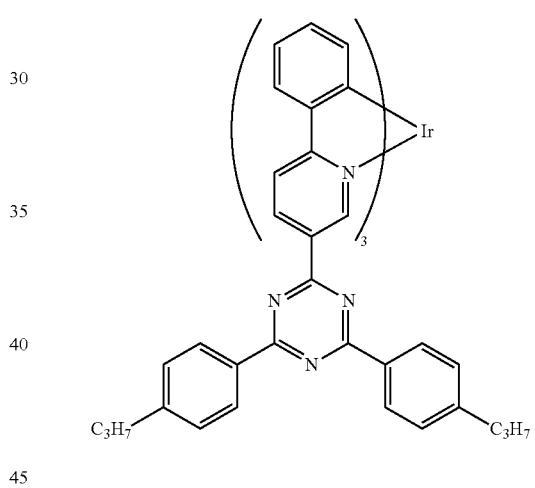
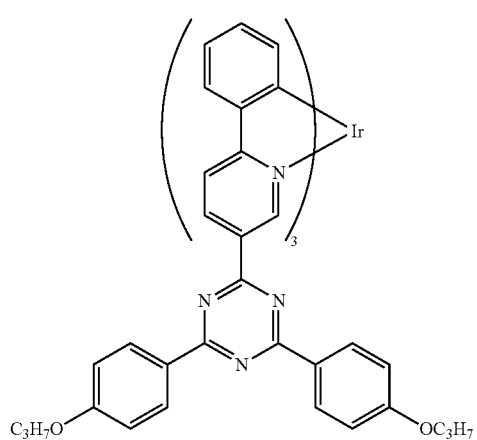
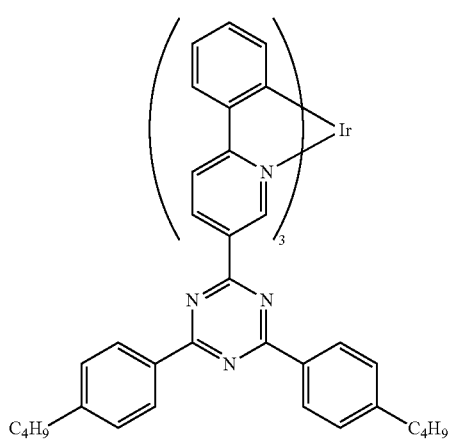

23
-continued
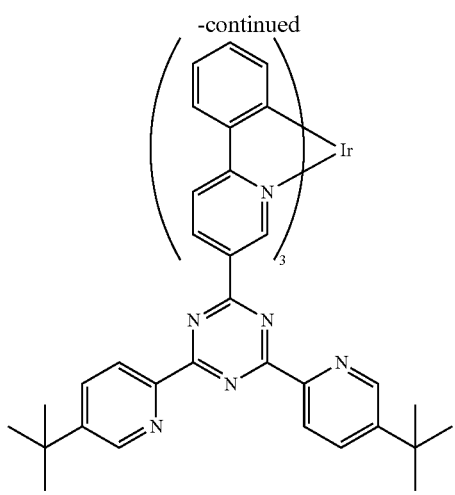
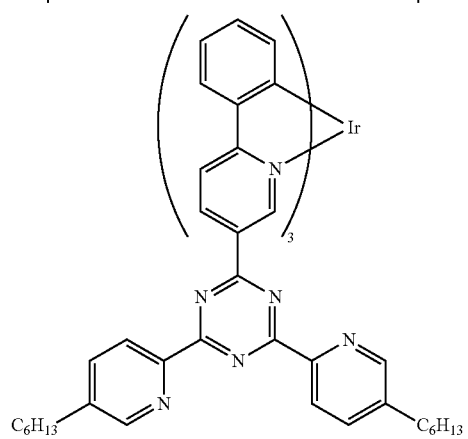
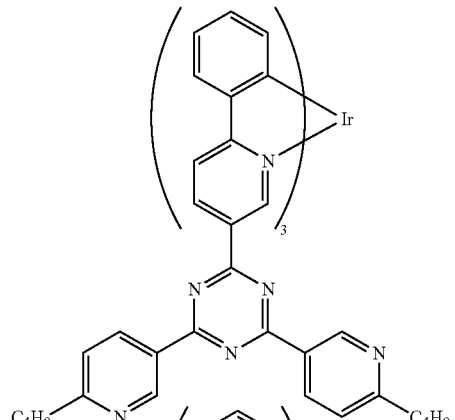
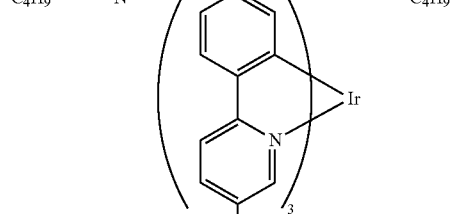
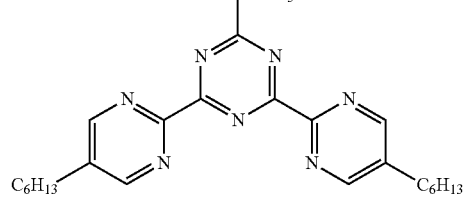
24
-continued
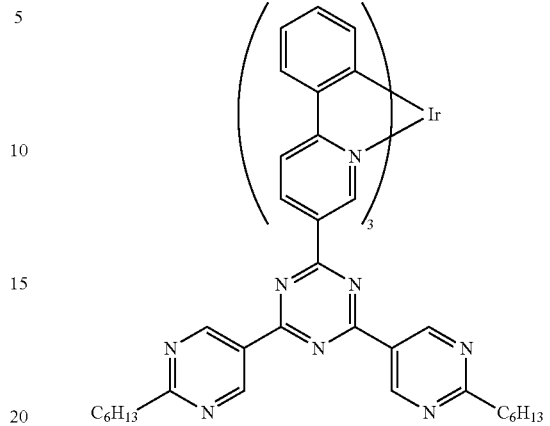
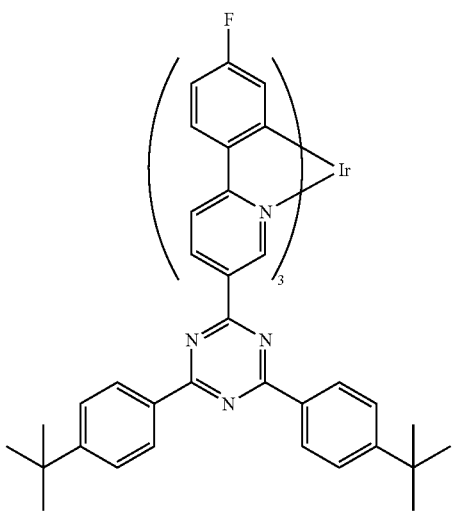
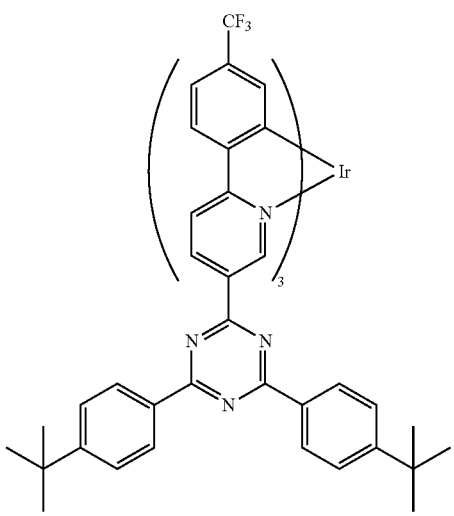

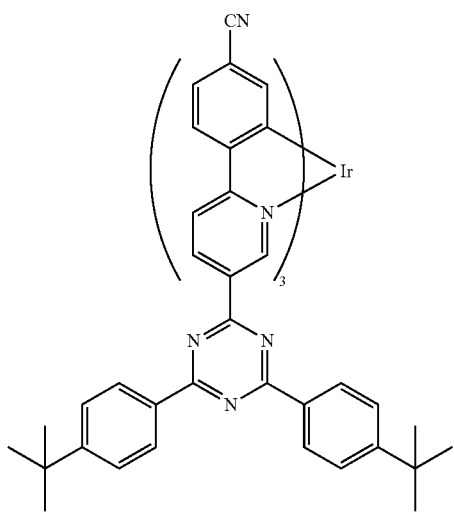
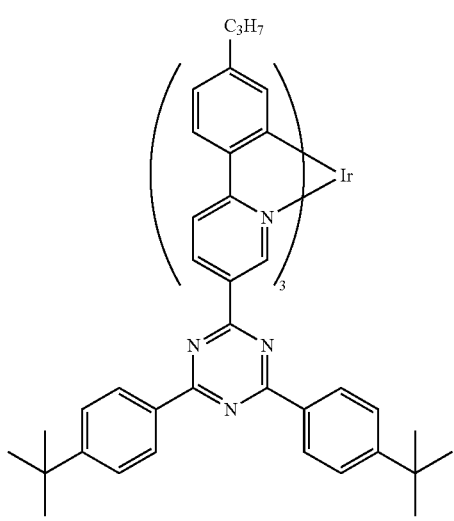
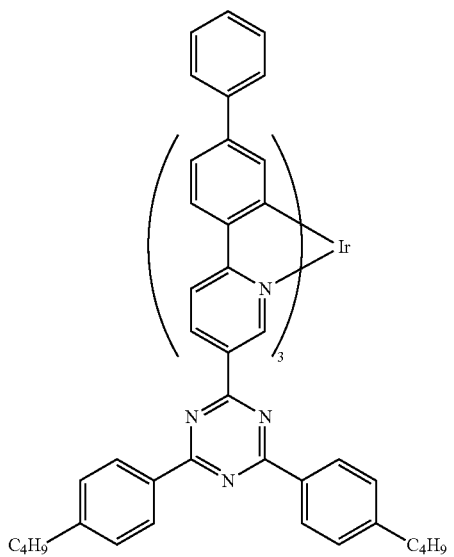
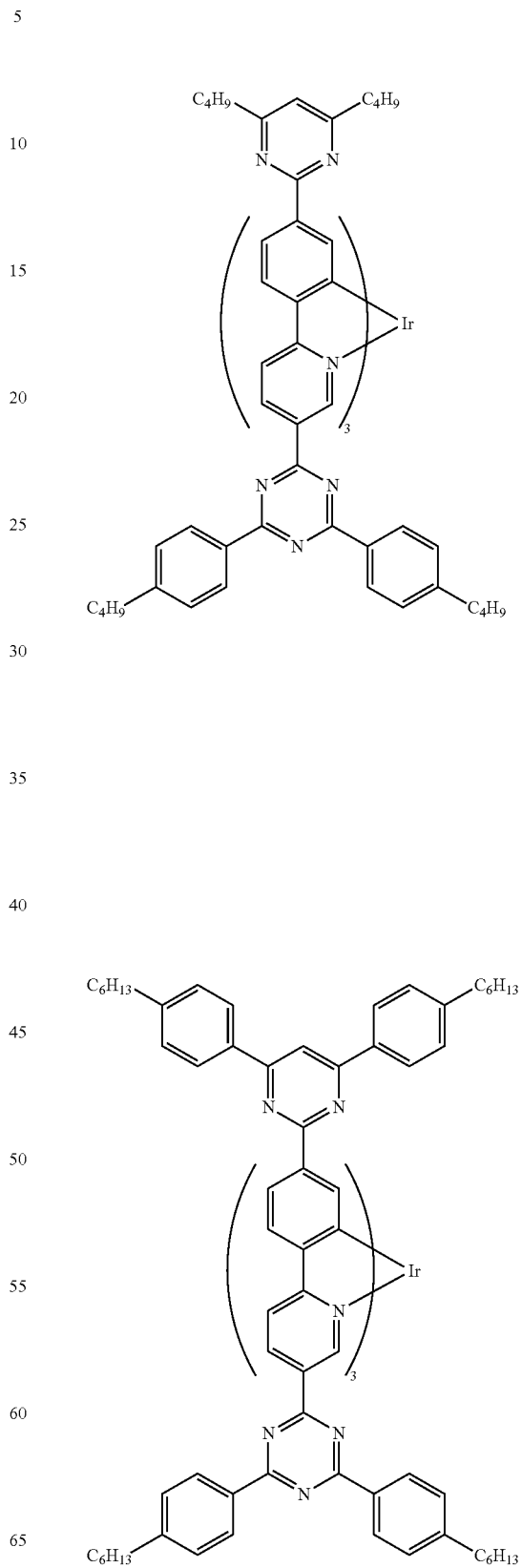

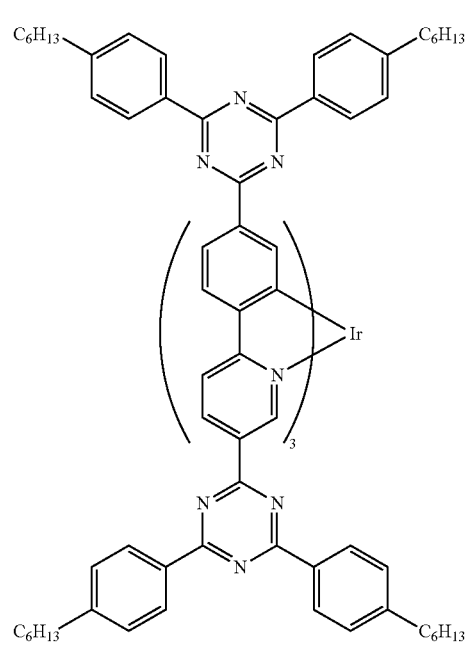
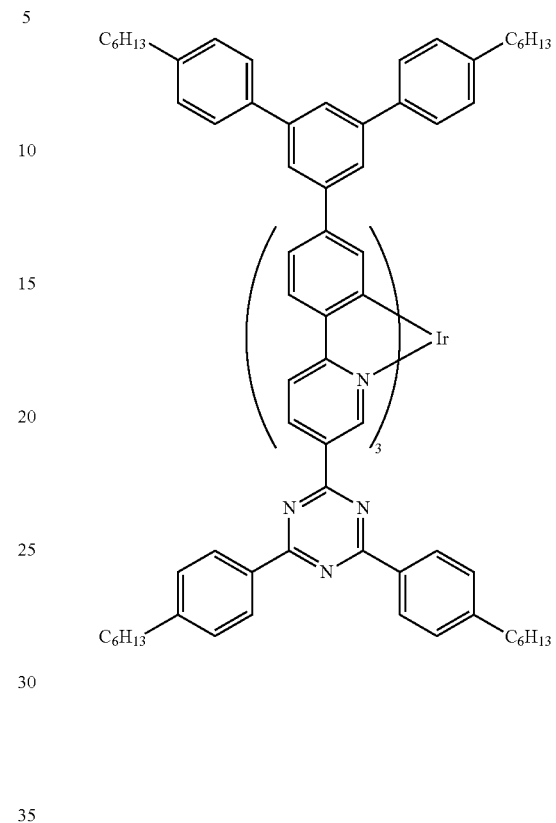
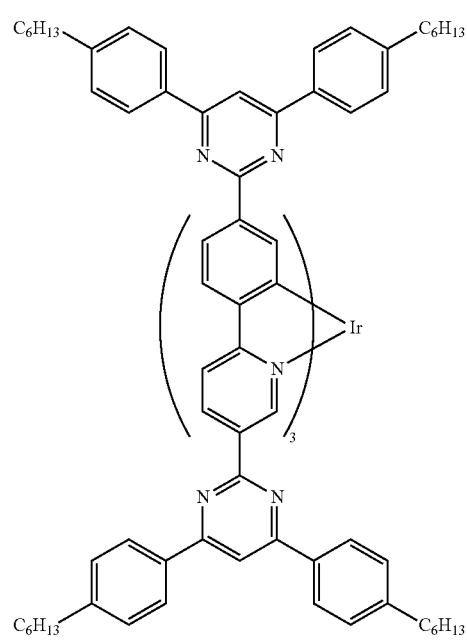
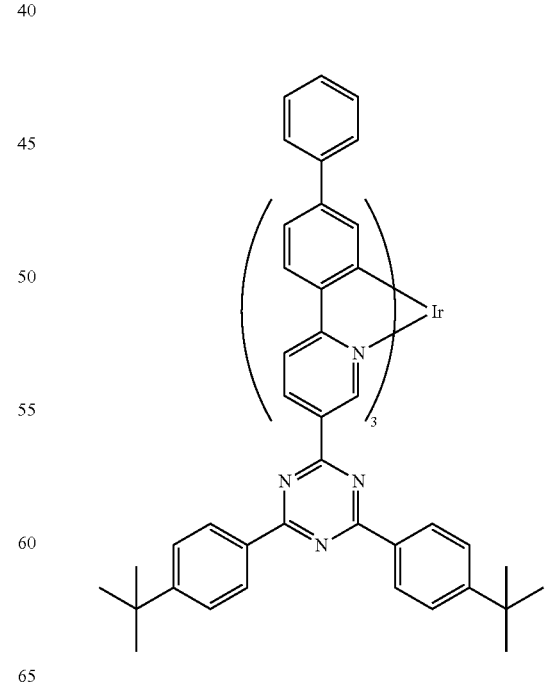

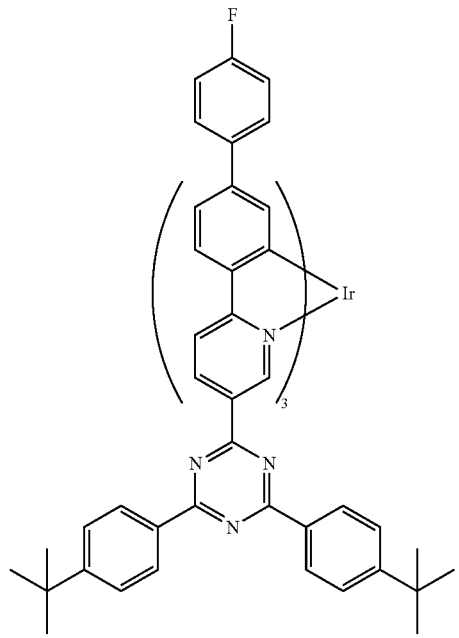
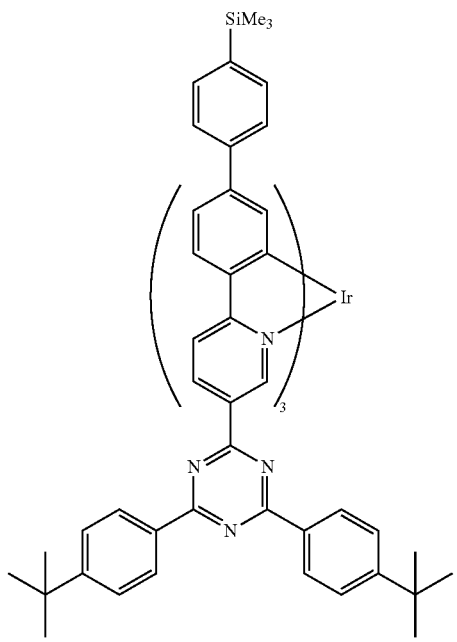
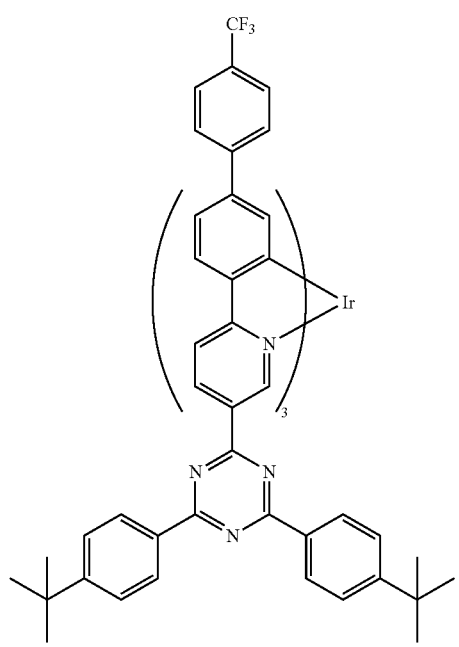
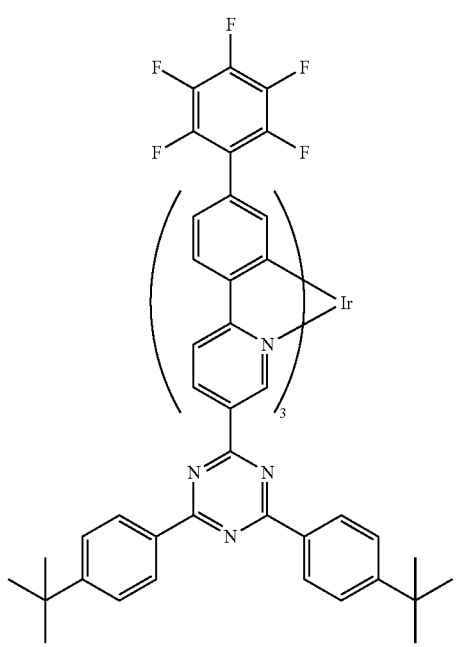

31
-continued
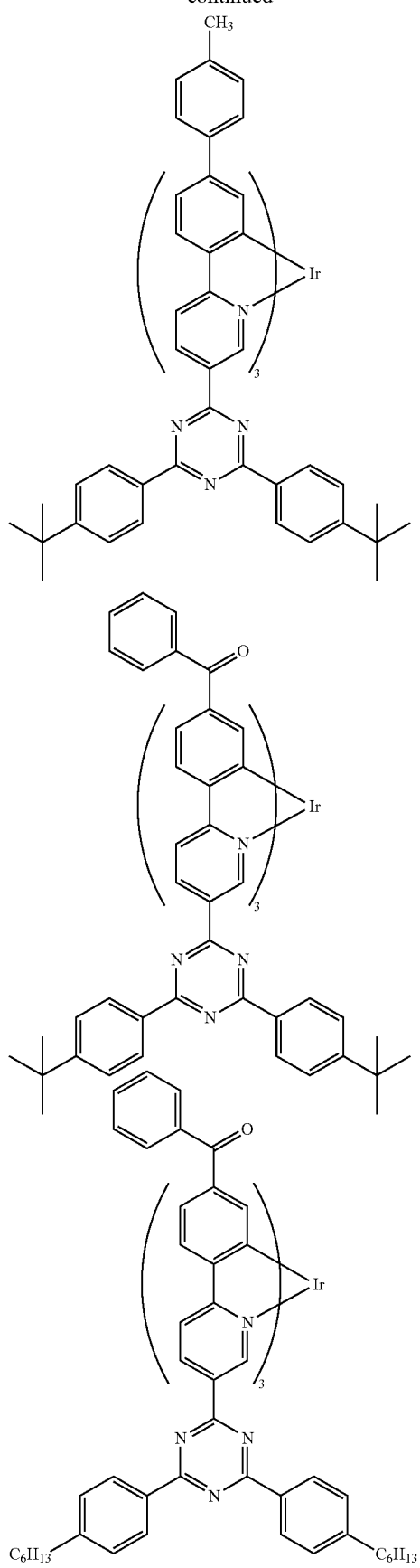
32
-continued
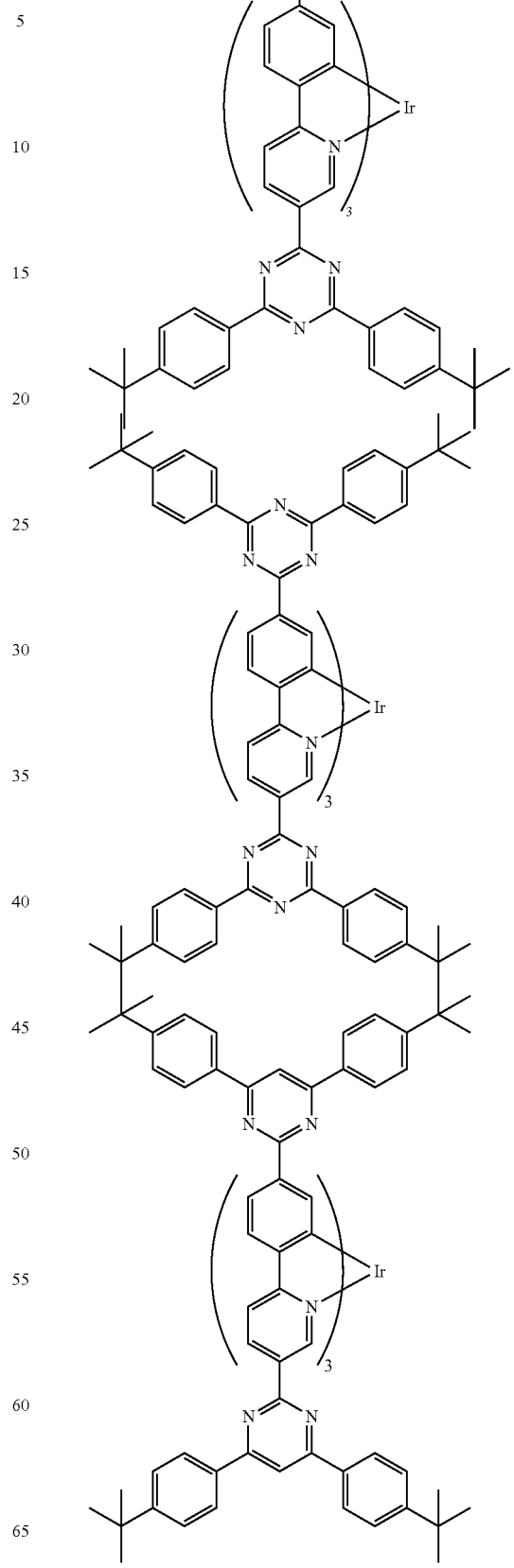

33
-continued
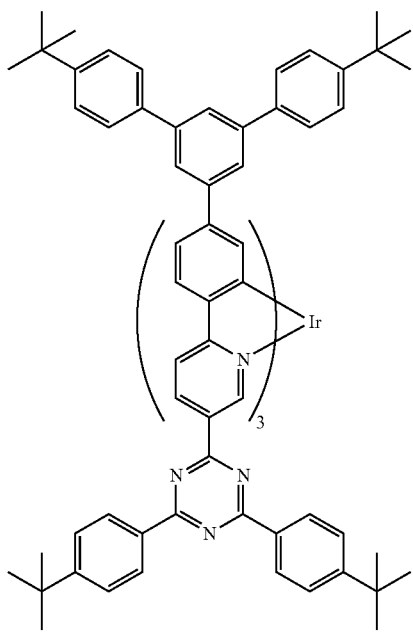
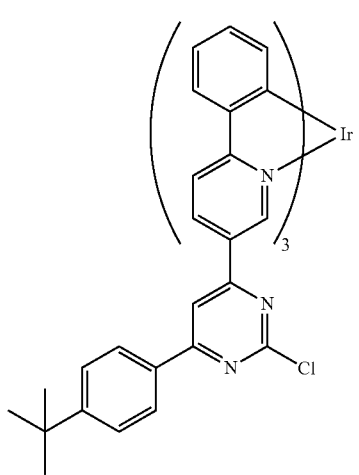
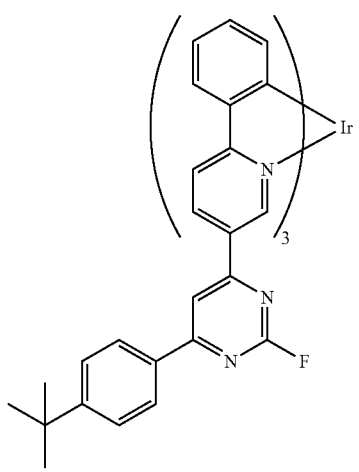
34
-continued
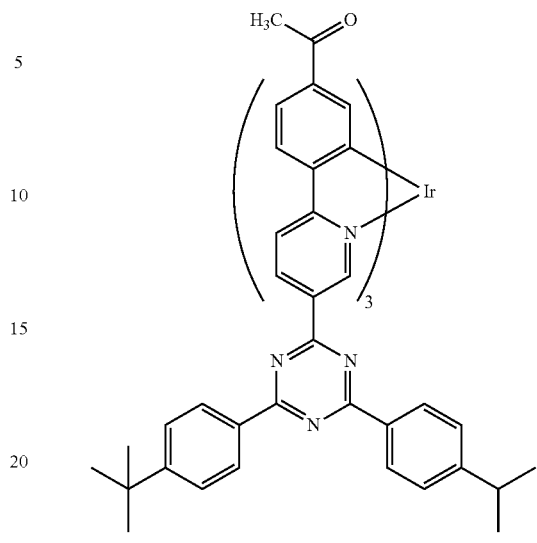

-continued

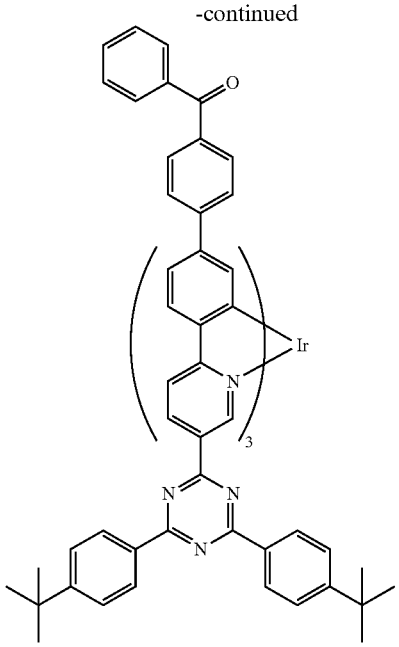

The metal complex of the present invention is preferably a metal complex whose triplet excited state has a short lifetime, which effectively makes forbidden transition allowable, from the viewpoint of stable light emission with high efficiency.

—Method for Producing Metal Complex—

Next, a method for producing the metal complex of the present invention will be described.

The metal complex of the present invention can be synthesized, for example, by reacting a compound serving as a ligand with a metal compound in a solution. The reaction system may contain a base, a silver chloride, and so on, if necessary. Alternatively, the metal complex of the present invention can be synthesized by performing a coupling reaction between a metal complex having a 2-phenylpyridine derivative as a ligand and a heterocyclic aromatic compound.

The complexation method (i.e., the method for reacting a compound serving as a ligand with a metal compound in a solution) is exemplified by: for an iridium complex, methods described in, e.g., J. Am. Chem. Soc. 1984, 106, 6647; Inorg. Chem. 1991, 30, 1685; Inorg. Chem. 1994, 33, 545; Inorg. Chem. 2001, 40, 1704; and Chem. Lett., 2003, 32, 252; for a platinum complex, methods described in, e.g., Inorg. Chem., 1984, 23, 4249; Chem. Mater. 1999, 11, 3709; and Organometallics, 1999, 18, 1801; and for a palladium complex, methods described in e.g., J. Org. Chem., 1987, 52, 73.

The complexation reaction temperature is not particularly limited, and the reaction can usually be performed at a temperature between the melting point and boiling point of a solvent, preferably −78° C. to the boiling point of a solvent. The reaction time is not particularly limited and is usually approximately 30 minutes to 30 hours. However, when a microwave reactor is used in the complexation reaction, the reaction can be performed even at a temperature equal to or higher than the boiling point of a solvent for a reaction time of, but not particularly limited to, approximately a few minutes to a few hours.

The compound serving as a ligand can be synthesized, for example, by Suzuki coupling, Grignard coupling, Stille coupling, or the like between a 2-phenylpyridine derivative and a heterocyclic aromatic compound. If necessary, these materials can be dissolved in an organic solvent and reacted at a temperature between the melting point and boiling point (inclusive) of the organic solvent using, for example, an alkali and an appropriate catalyst to synthesize the compound serving as a ligand. In this synthesis, methods can be used which are described in, e.g., "Organic Syntheses", Collective Volume VI, p. 407-411, John Wiley & Sons, Inc., 1988; Chem. Rev., vol. 106, p. 2651, (2006); Chem. Rev., vol. 102, p. 1359, (2002); Chem. Rev., vol. 95, p. 2457, (1995); and J. Organomet. Chem., vol. 576, p. 147, (1999).

The heterocyclic aromatic compound can be synthesized by methods described in e.g., "HOUBEN-WEYL METHODS OF ORGANIC CHEMISTRY $4^{TH}$ EDITION", vol. E9b, p. 1, GEORG THIEME VERLAG STUTTGART; and HOUBEN-WEYL METHODS OF ORGANIC CHEMISTRY $4^{TH}$ EDITION, vol. E9c, p. 667, GEORG THIEME VERLAG STUTTGART.

Moreover, it is also preferred that the metal complex of the present invention should be produced by a method comprising performing a coupling reaction between a heterocyclic aromatic compound having a halogen atom or an alkyl sulfonate group and a compound represented by any of the formulas (A-1) to (A-3). In the formulas (A-1) to (A-3), M, $R^1$, $R^3$, $R^4$, $R^5$, $R^6$, $R^8$, m, n, $R^x$ and $R^y$ are as defined above. $L^1$ and $L^2$ have the same definition as those described and exemplified as $R^1$.

A catalyst used in the coupling reaction is not particularly limited and is preferably a palladium catalyst. The palladium catalyst is exemplified by palladium acetate, bis(triphenylphosphine)palladium(II) dichloride, tetrakis(triphenylphosphine)palladium(0), [1,1'-bis(diphenylphosphino)ferrocene]dichloropalladium(II) and tris(dibenzylideneacetone)dipalladium(0). Tetrakis(triphenylphosphine)palladium(0), [1,1'-bis(diphenylphosphino)ferrocene]dichloropalladium(II) and tris(dibenzylideneacetone)dipalladium(0) are preferable. The palladium catalyst may contain a phosphorus ligand, if necessary. The phosphorus ligand is exemplified by triphenylphosphine, tri(o-tolyl)phosphine, tri(t-butyl)phosphine, tricyclohexylphosphine and 1,1'-bis(diphenylphosphino)ferrocene.

The amount of the catalyst used in the coupling reaction is not particularly limited and is preferably 1 mol % or larger, more preferably 10 mol % or larger, particularly preferably 30 mol % or larger, with respect to the compound represented by any of the formulas (A-1) to (A-3).

The compound represented by any of the formulas (A-1) to (A-3) can be synthesized, for example, by borating or borate-esterifying a compound represented by any of the following formulas (C-1) to (C-3):

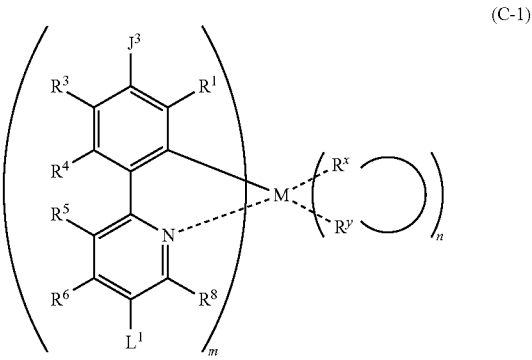

(C-1)

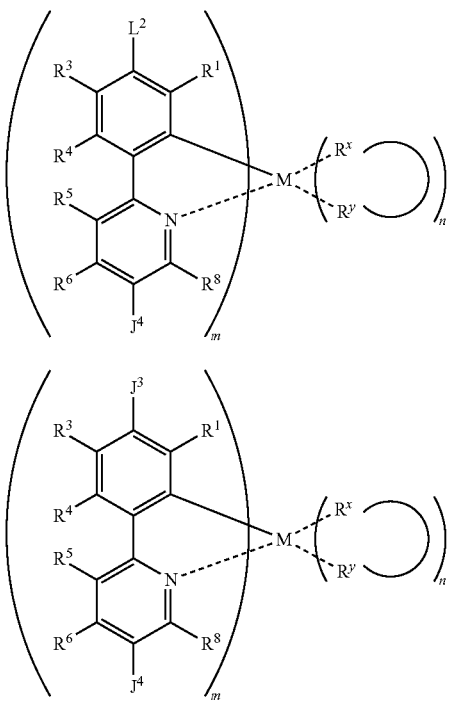

(C-2)

(C-3)

wherein M, $R^1$, $R^3$ to $R^6$, $R^8$, $L^1$, $L^2$, $R^x$, $R^y$, m and n are as defined above; and $J^3$ and $J^4$ each independently represent a halogen atom.

Alternatively, the metal complex of the present invention can be synthesized by Suzuki coupling, Grignard coupling, Stille coupling, or the like between the compound represented by any of the formulas (C-1) to (C-3) and the heterocyclic aromatic compound.

The obtained metal complex can be identified and analyzed by CHN elementary analysis, NMR analysis and MS analysis.

<Polymer Compound>

A polymer compound of the present invention contains a residue of the metal complex of the present invention and is preferably a conjugated polymer from the viewpoint of conductivity. Examples of the molecule containing a residue of the metal complex include polymer organic compounds used as charge transport materials described later. Conjugated polymer organic compounds are preferable, because extended conjugation enhances carrier (electron or hole) mobility.

When the metal complex of the present invention is contained in the polymer organic compound, examples of the polymer compound having a polymer organic compound structure and a residue of the metal complex in one molecule include:

1. a polymer compound having the residue of the metal complex in the main chain of the polymer organic compound;
2. a polymer compound having the residue of the metal complex in the end of the polymer organic compound; and
3. a polymer compound having the residue of the metal complex in the side chain of the polymer organic compound.

The polymer compound having the residue of the metal complex in the main chain includes those containing the metal complex incorporated in the main chain of a linear polymer as well as those containing three or more polymer chains bonded to the metal complex.

Examples of the polymer compound include those containing a residue of the metal complex having a structure represented by the formula (1) or the like in the side chain, main chain or end thereof, or two or more of them and having a number-average molecular weight of $1 \times 10^3$ to $1 \times 10^8$ based on polystyrene standards.

The polymer compound having the residue of the metal complex in the main chain of the polymer organic compound is represented by, for example, the following formula:

wherein $M_1$ and $M_2$ represent a residue of the metal complex whose bond is held by the ligand in the metal complex, and the $M_1$ and the $M_2$ are bonded via the bond to a repeating unit constituting the polymer main chain.

The polymer compound having the residue of the metal complex in the end of the polymer organic compound is represented by, for example, the following formula:

wherein $M_3$ represents a monovalent residue of the metal complex whose bond is held by the ligand in the metal complex, and the $M_3$ is bonded via the bond to X; and X represents a single bond, an alkenylene group which may be substituted, an alkynylene group which may be substituted, an arylene group which may be substituted or a divalent heterocyclic group which may be substituted.

The polymer compound having the residue of the metal complex in the side chain of the polymer organic compound is represented by, for example, the formula —Ar'—, wherein Ar' represents a divalent aromatic group or a divalent heterocyclic group having one or more atoms selected from the group consisting of an oxygen atom, a silicon atom, a germanium atom, a tin atom, a phosphorus atom, a boron atom, a sulfur atom, a selenium atom and a tellurium atom, and the Ar' has 1 to 4 groups represented by -L-X; X represents a monovalent residue of the metal complex; L represents a single bond, —O—, —S—, —C(=O)—, —C(=O)O—, —S(=O)—, —S(=O)$_2$—, —Si($R^{68}$)($R^{69}$)—, N($R^{70}$)—, —B($R^{71}$)—, —P($R^{72}$)—, —P(=O)($R^{73}$)—, an alkylene group which may be substituted, an alkenylene group which may be substituted, an alkynylene group which may be substituted, an arylene group which may be substituted or a divalent heterocyclic group which may be substituted, and when the alkylene group, the alkenylene group and the alkynylene group contains a —CH$_2$— group, one or more —CH$_2$— groups contained in the alkylene group, one or more —CH$_2$—groups contained in the alkenylene group, and one or more —CH$_2$— groups contained in the alkynylene group may respectively be substituted by a group selected from the group consisting of —O—, —S—, —C(=O)—, —C(=O)O—, —S(=O)—, —S(=O)$_2$—, —Si($R^{74}$)($R^{75}$)—, N($R^{76}$)—, —B($R^{77}$)—, —P($R^{78}$)— and —P(=O)($R^{79}$)—; $R^{68}$ to $R^{79}$ each independently represent a group selected from the group consisting of a hydrogen atom, an alkyl group, an aryl group, a monovalent heterocyclic group and a cyano group; and Ar may have, in addition to the group represented by -L-X, a substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group, and when Ar' has plural substituents, they may be the same or different.

In the formula, the alkyl group, the aryl group, the monovalent heterocyclic group and the cyano group represented by $R^{68}$ to $R^{79}$ as well as the alkyl group, the alkoxy group, the alkylthio group, the aryl group, the aryloxy group, the arylthio group, the arylalkyl group, the arylalkoxy group, the arylalkylthio group, the arylalkenyl group, the arylalkynyl group, the amino group, the substituted amino group, the silyl group, the substituted silyl group, the halogen atom, the acyl group, the acyloxy group, the imine residue, the amide group, the acid imide group, the monovalent heterocyclic group, the carboxyl group, the substituted carboxyl group and the cyano group as substituents which may be contained in Ar' are the same as those described and exemplified as the substituents represented by R.

In the formula, examples of the divalent aromatic group include phenylene, pyridinylene, pyrimidylene and naphthylene.

In the formula, the divalent heterocyclic group means an atomic group derived from a heterocyclic compound by removal of two hydrogen atoms. The divalent heterocyclic group usually has approximately 4 to 60 carbon atoms, preferably 4 to 20 carbon atoms. In this context, the carbon number of the substituent is excluded from the carbon number of the divalent heterocyclic group. The heterocyclic compound is the same as those described and exemplified as the monovalent heterocyclic group. Moreover, the divalent heterocyclic group is preferably a divalent aromatic heterocyclic group.

The polymer compound of the present invention is not particularly limited as long as it has a residue of the metal complex of the present invention. It is preferred that the polymer compound should not largely impair charge transport properties, charge injection properties, or the like. Specifically, the polymer compound is preferably a conjugated polymer excellent in carrier (electron or hole) transport properties.

It is preferred that the polymer compound of the present invention should contain a group represented by the following formula (I):

—Ar— (I)

wherein Ar represents an arylene group, a divalent heterocyclic group or a divalent aromatic amine group, and these groups may have a substituent.

In the formula (I), the arylene group represented by Ar is exemplified by a phenylene group which may have a substituent, a naphthylene group which may have a substituent, and a group represented by the following formula (3a):

(3a)

wherein the P ring which may be absent and the Q ring each independently represent an aromatic ring, wherein two bonds are respectively present on the P ring or the Q ring in the presence of the P ring and are respectively present on a $Y^1$-containing five-membered or six-membered ring or the Q ring in the absence of the P ring; the P ring, the Q ring and the $Y^1$-containing five-membered or six-membered ring may each independently have at least one substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; $Y^1$ represents —C($R^{11}$)($R^{12}$)—, —C($R^{14}$)($R^{15}$)—C($R^{16}$)($R^{17}$)— or —C($R^{32}$)=C($R^{33}$)—; and $R^{11}$, $R^{12}$, $R^{14}$ to $R^{17}$, $R^{32}$ and $R^{33}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

In the formula (I), the alkyl group, the alkoxy group, the alkylthio group, the aryl group, the aryloxy group, the arylthio group, the arylalkyl group, the arylalkoxy group, the arylalkylthio group, the arylalkenyl group, the arylalkynyl group, the amino group, the substituted amino group, the silyl group, the substituted silyl group, the halogen atom, the acyl group, the acyloxy group, the imine residue, the amide group, the acid imide group, the monovalent heterocyclic group, the carboxyl group, the substituted carboxyl group and the cyano group as substituents which may be contained in the P ring, the Q ring and the $Y^1$-containing five-membered or six-membered ring are the same as those described and exemplified as the groups represented by R.

In the formula (I), the alkyl group, the alkoxy group, the alkylthio group, the aryl group, the aryloxy group, the arylthio group, the arylalkyl group, the arylalkoxy group, the arylalkylthio group, the arylalkenyl group, the arylalkynyl group, the amino group, the substituted amino group, the silyl group, the substituted silyl group, the silyloxy group, the substituted silyloxy group, the monovalent heterocyclic group and the halogen atom represented by $R^{11}$, $R^{12}$, $R^{14}$ to $R^{17}$, $R^{32}$ and $R^{33}$ are the same as those described and exemplified as the groups represented by R.

In the formula (I), the divalent heterocyclic group represented by Ar refers to an atomic group derived from a heterocyclic compound by removal of two hydrogen atoms. The group may have a substituent. The heterocyclic compound refers to, of organic compounds having a cyclic structure, those having not only a carbon atom but also one or more atoms selected from the group consisting of an oxygen atom, a nitrogen atom, a silicon atom, a germanium atom, a tin atom, a phosphorus atom, a boron atom, a sulfur atom, a selenium atom and a tellurium atom as elements constituting the ring. Moreover, the divalent heterocyclic group is preferably a divalent aromatic heterocyclic group. The divalent heterocyclic group usually has approximately 3 to 60 carbon atoms in the moiety exclusive of the substituent. The divalent heterocyclic group usually has a total of approximately 3 to 100 carbon atoms, inclusive of the substituent.

In the formula (I), the divalent heterocyclic group represented by Ar is exemplified by a group represented by the following formula (3b):

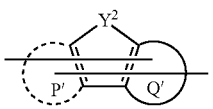

(3b)

wherein the P' ring which may be absent and the Q' ring each independently represent an aromatic ring, wherein two bonds are respectively present on the P' ring or the Q' ring in the presence of the P' ring and are respectively present on a $Y^2$-containing five-membered or six-membered ring or the Q' ring in the absence of the P' ring; the P' ring, the Q' ring and the $Y^2$-containing five-membered or six-membered ring may each independently have at least one substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; $Y^2$ represents —O—, —S—, —Se—, —B($R^6$)—, —Si($R^7$)($R^8$)—, —P($R^9$)—, —P$R^{10}$(=O)—, —N($R^{13}$)—, —O—C($R^{18}$)($R^{19}$)—, —S—C($R^{20}$)($R^{21}$)—, —N—C($R^{22}$)($R^{23}$)—, —Si($R^{24}$)($R^{25}$)—C($R^{26}$)($R^{27}$)—, —Si($R^{28}$)($R^{29}$)—Si($R^{30}$)($R^{31}$)—, —N=C($R^{34}$)— or —Si($R^{35}$)=C($R^{36}$)—; and $R^6$ to $R^{10}$, $R^{13}$, $R^{18}$ to $R^{31}$ and $R^{34}$ to $R^{36}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

In the formula, the alkyl group, the alkoxy group, the alkylthio group, the aryl group, the aryloxy group, the arylthio group, the arylalkyl group, the arylalkoxy group, the arylalkylthio group, the arylalkenyl group, the arylalkynyl group, the amino group, the substituted amino group, the silyl group, the substituted silyl group, the halogen atom, the acyl group, the acyloxy group, the imine residue, the amide group, the acid imide group, the monovalent heterocyclic group, the carboxyl group, the substituted carboxyl group and the cyano group as substituents which may be contained in the P' ring, the Q' ring and the $Y^2$-containing five-membered or six-membered ring are the same as those described and exemplified as the groups represented by R.

In the formula, the alkyl group, the alkoxy group, the alkylthio group, the aryl group, the aryloxy group, the arylthio group, the arylalkyl group, the arylalkoxy group, the arylalkylthio group, the arylalkenyl group, the arylalkynyl group, the amino group, the substituted amino group, the silyl group, the substituted silyl group, the silyloxy group, the substituted silyloxy group, the monovalent heterocyclic group and the halogen atom represented by $R^6$ to $R^{10}$, $R^{13}$, $R^{18}$ to $R^{31}$ and $R^{34}$ to $R^{36}$ are the same as those described and exemplified as the groups represented by R.

In the formula (I), the divalent aromatic amine group represented by Ar means an atomic group derived form aromatic amine by removal of two hydrogen atoms. The divalent aromatic amine group usually has approximately 5 to 100 carbon atoms, preferably 15 to 60 carbon atoms. In this context, the carbon number of the substituent is excluded from the carbon number of the divalent aromatic amine group.

In the formula (I), the divalent aromatic amine group represented by Ar is exemplified by a group represented by the following formula (7):

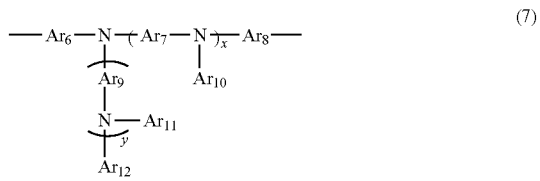

(7)

wherein $Ar_6$, $Ar_7$, $Ar_8$ and $Ar_9$ each independently represent an arylene group or a divalent heterocyclic group; $Ar_{10}$, $Ar_{11}$, and $Ar_{12}$ each independently represent an aryl group or a monovalent heterocyclic group; $Ar_6$ to $Ar_{12}$ may have a substituent; and x and y are each independently 0 or 1, wherein $0 \leq x+y \leq 1$.

In the formula (7), the arylene group represented by $Ar_6$ to $Ar_9$ refers to an atomic group derived from aromatic hydrocarbon by removal of two hydrogen atoms. The aromatic hydrocarbon includes those having a condensed ring and those comprising two or more independent benzene rings or condensed rings bonded directly or via a group such as vinylene. The arylene group may have a substituent. The arylene group usually has approximately 6 to 60 carbon atoms, preferably 6 to 20 carbon atoms, in the moiety exclusive of the substituent. The arylene group usually has a total of approximately 6 to 100 carbon atoms, inclusive of the substituent.

In the formula (7), the divalent heterocyclic group represented by $Ar_6$ to $Ar_9$ is the same as those described and exemplified as the divalent heterocyclic groups represented by Ar.

In the formula (7), the aryl group and the monovalent heterocyclic group represented by $Ar_{10}$ to $Ar_{12}$ are the same as those described and exemplified as the aryl groups and the monovalent heterocyclic groups represented by R.

In the formula (7), examples of the substituent which may be contained in the arylene group, the divalent heterocyclic group, the aryl group and the monovalent heterocyclic group include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, a cyano group and a nitro group. These substituents are specifically the same as those described and exemplified as the substituents which may be contained in the ligand constituting the metal complex of the present invention.

In the formula (3a), examples of the group represented by the formula (3b) include: a group represented by the following formula (3-1), (3-2) or (3-3):

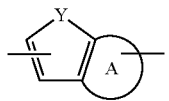

Formula (3-1)

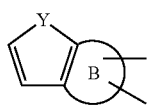

Formula (3-2)

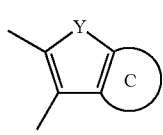

Formula (3-3)

wherein the A ring, the B ring and the C ring each independently represent an aromatic ring; the formulas (3-1), (3-2) and (3-3) may respectively have one or more substituents selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; and Y is the same as those represented by $Y^1$ or $Y^2$; and a group represented by the following formula (3-4) or (3-5):

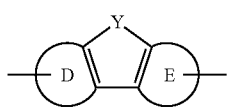

Formula (3-4)

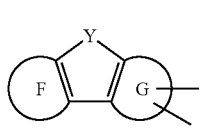

Formula (3-5)

wherein the D ring, the E ring, the F ring and the G ring each independently represent an aromatic ring which may have one or more substituents selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; and Y is as defined above.

The group represented by the formula (3-4) or (3-5) is preferable.

In the formula, Y is preferably —S—, —O— or —C($R^{11}$)($R^{12}$)— from the viewpoint of high luminous efficiency, more preferably —S— or —O—. In this context, $R^{11}$ and $R^{12}$ are as defined above.

Examples of the aromatic ring in the formulas (3-1) to (3-5) include: aromatic hydrocarbon rings such as benzene, naphthalene, anthracene, tetracene, pentacene, pyrene and phenanthrene rings; and heterocyclic aromatic rings such as pyridine, bipyridine, phenanthroline, quinoline, isoquinoline, thiophene, furan and pyrrole rings.

The substituent which may be contained in the groups represented by the formulas (3-1) to (3-5) is preferably an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, an acyloxy group, an imine residue, an amide group, an acid imide group, a monovalent heterocyclic group, a carboxyl group or a substituted carboxyl group.

<Composition>

A composition of the present invention contains the metal complex and/or the polymer compound and, preferably, further contains a charge transport material and/or a light-emitting material.

The charge transport material is classified into a hole transport material and an electron transport material. Specifically, an organic compound (low-molecular organic compound and/or polymer organic compound) can be used.

Examples of the hole transport material include those known in the art as hole transport materials for organic EL devices, such as aromatic amine, carbazole derivatives and polyparaphenylene derivatives. Examples of the electron transport material include those known in the art as electron transport materials for organic EL devices, for example, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives and metal complexes of 8-hydroxyquinoline and derivatives thereof. The low-molecular organic compound serving as the charge transport material means host compounds and charge injection/transport compounds used in low-molecular organic EL devices. Specific examples thereof include compounds described in, e.g., "Organic EL Display" (S. Tokito, C. Adachi and H. Murata, Ohmsha, Ltd.), p. 107; Monthly Display, vol. 9, No. 9, 2003, p. 26-30; JP-A-2004-244400; and JP-A-2004-277377. Depending on the types of these charge transport materials, it is generally preferred for obtaining favorable light emission from the metal complex that the lowest triplet excitation energy of these charge transport materials should be larger than that of the metal complex.

Examples of the low-molecular organic compound serving as the charge transport material can include the following compounds:

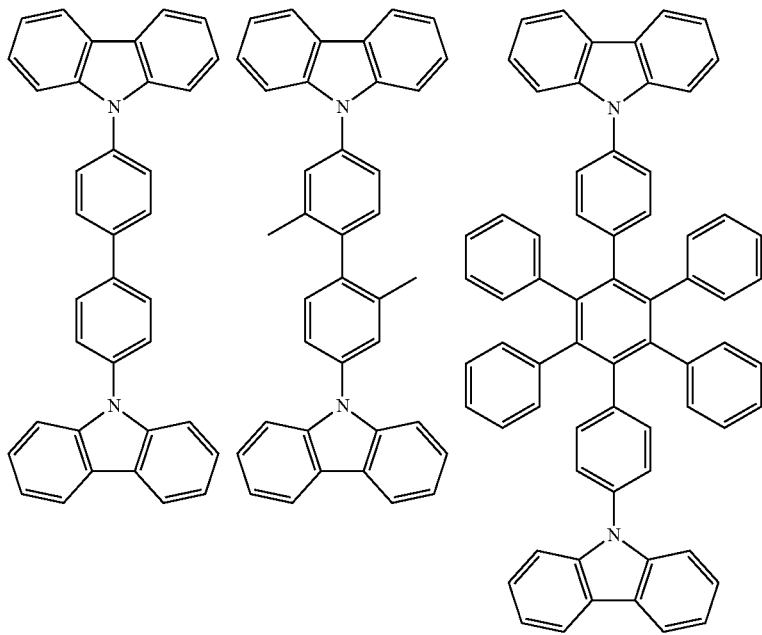
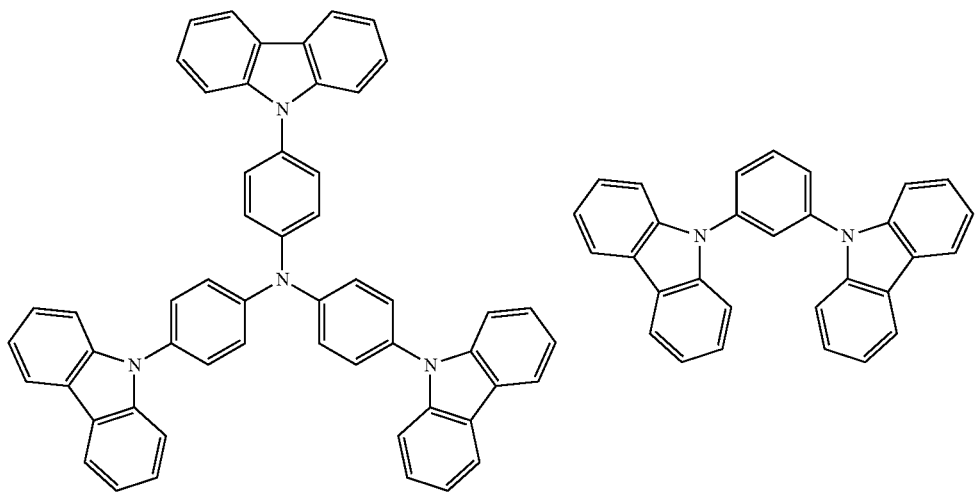
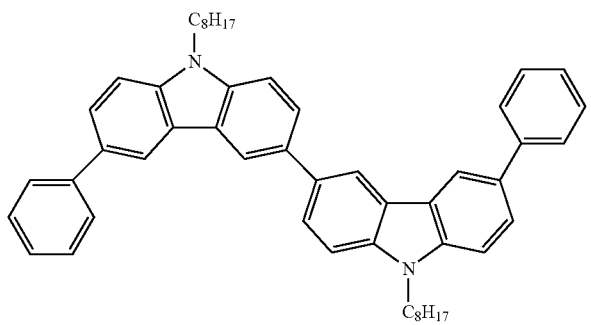

-continued
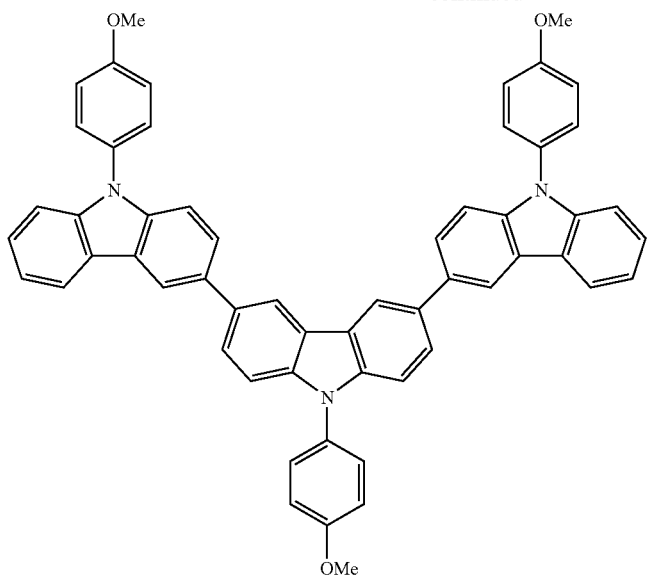
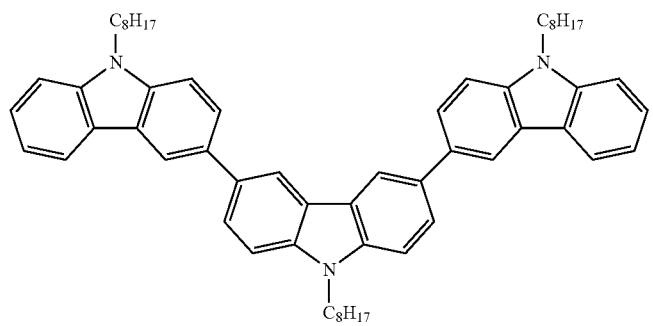
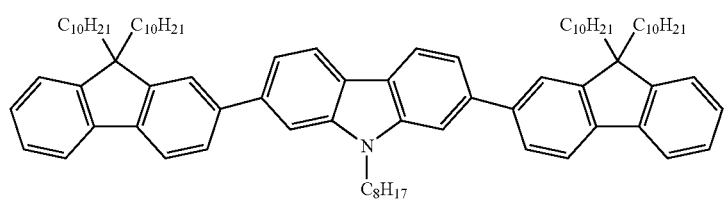
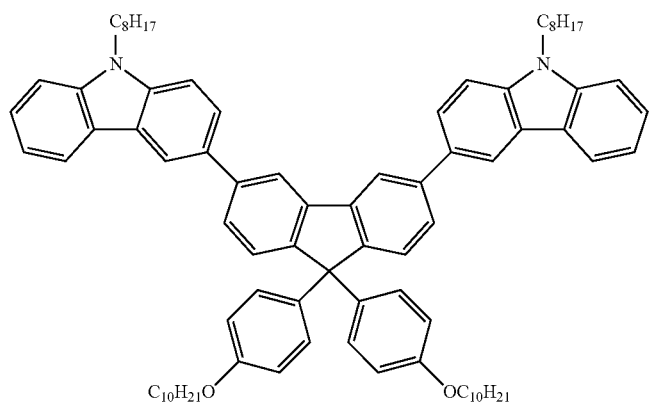

-continued
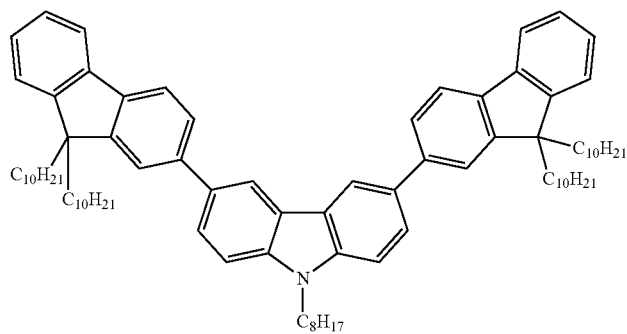
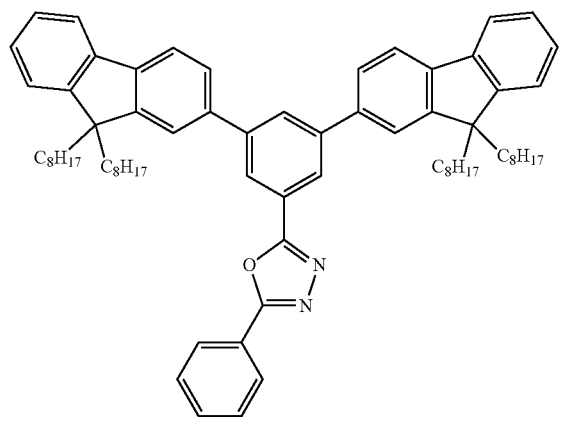
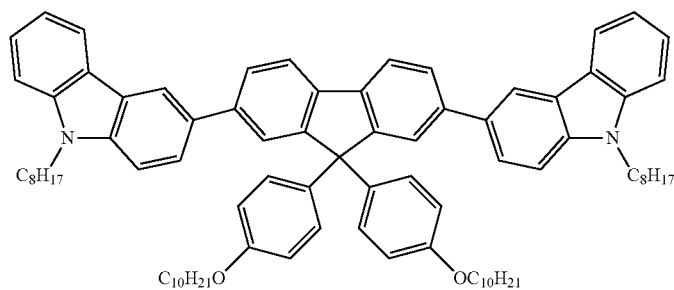
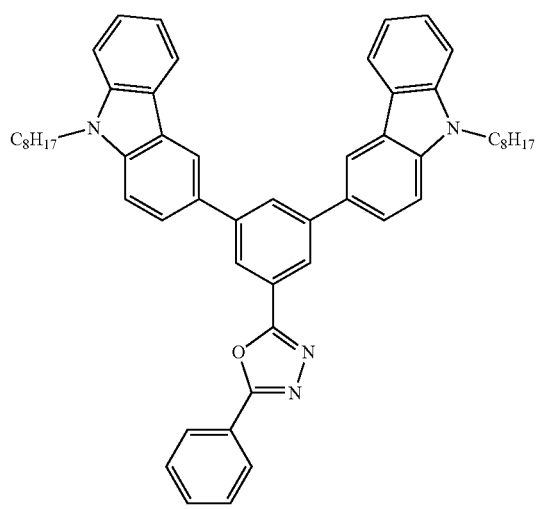
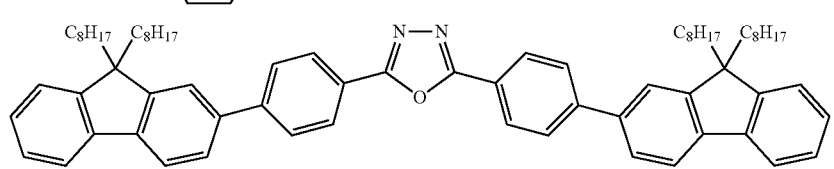

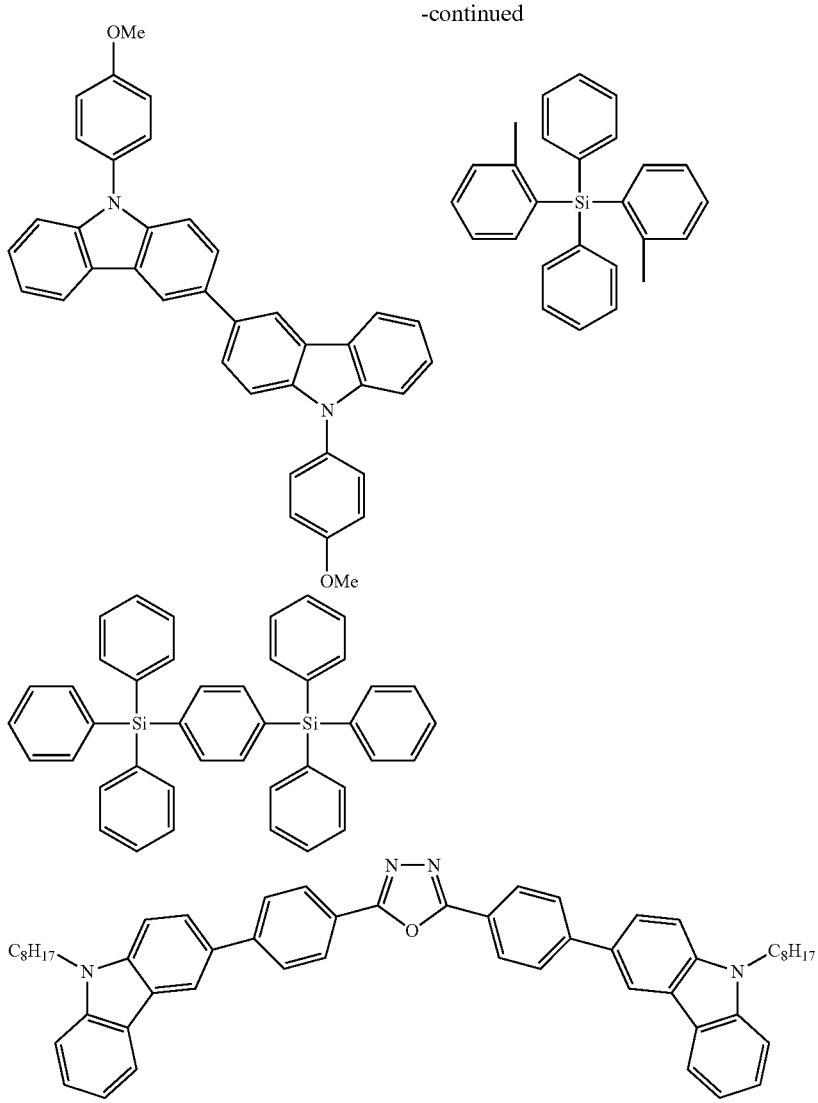

Examples of the polymer organic compound serving as the charge transport material include non-conjugated polymers and conjugated polymers. Examples of the non-conjugated polymers include polyvinylcarbazole. Examples of the conjugated polymers include polymers containing an aromatic ring in the main chain. Examples thereof include those containing a phenylene group which may have a substituent, fluorene which may have a substituent, dibenzothiophene which may have a substituent, dibenzofuran which may have a substituent or dibenzosilole which may have a substituent as a repeating unit in the main chain, and copolymers with these units. Specific examples thereof include polymer compounds characterized by having a benzene ring which may have a substituent as a partial structure. Further specific examples thereof include polymers described in, e.g., JP-A-2003-231741, JP-A-2004-059899, JP-A-2004-002654, JP-A-2004-292546, U.S. Pat. No. 5,708,130, WO99/54385, WO00/46321, WO02/077060, "Organic EL Display" (S. Tokito, C. Adachi and H. Murata, Ohmsha, Ltd.), p. 111, and Monthly Display, vol. 9, No. 9, 2002, p. 47-51.

Other examples of the polymer organic compound serving as the charge transport material include polymers containing a repeating unit represented by the formula (3a) or (3b). Examples thereof include those containing the following groups (i.e., groups exemplified below, exclusive of the moiety inside the parentheses) and those containing the following structures as repeating units:

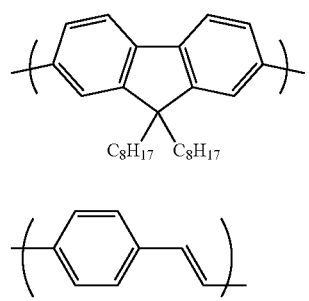

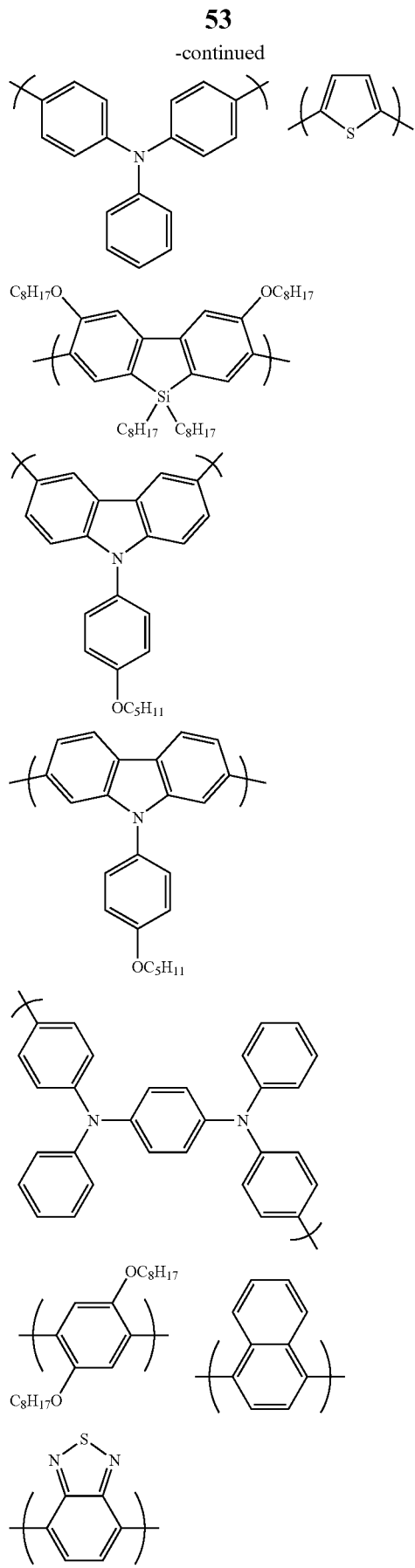

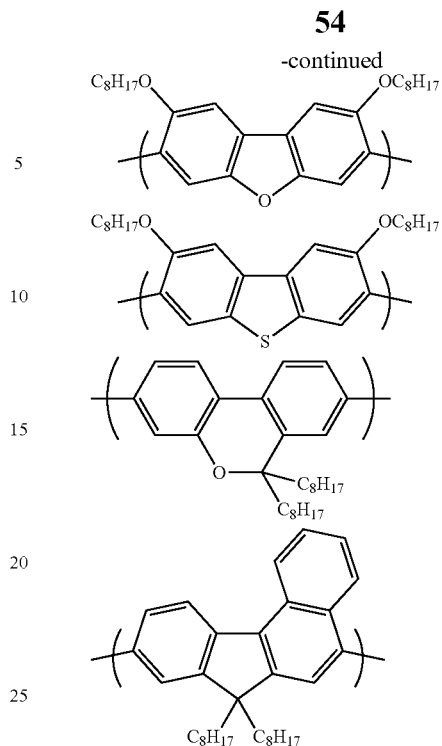

It is preferred that the low-molecular organic compound or the polymer organic compound serving as the charge transport material should have a lowest triplet excitation energy (TH) that satisfies the relationship with a lowest triplet excitation energy (TM) of the metal complex: TH>TM−0.2 (eV).

When the polymer organic compound is used as the charge transport material, the polymer organic compound has a number-average molecular weight of preferably $10^3$ to $10^8$, more preferably $10^4$ to $10^6$, based on polystyrene standards. Moreover, the polymer has a weight-average molecular weight of preferably $10^3$ to $10^8$, more preferably $5\times10^4$ to $5\times10^6$, based on polystyrene standards.

Materials known in the art can be used as the light-emitting material. Examples thereof include low-molecular light-emitting materials such as naphthalene derivatives, anthracene and derivatives thereof, perylene and derivatives thereof, dyes (e.g., polymethine, xanthene, coumarin and cyanine), metal complexes of 8-hydroxyquinoline and derivatives thereof, aromatic amine, tetraphenylcyclopentadiene and derivatives thereof and tetraphenylbutadiene and derivatives thereof.

The amount of the metal complex of the present invention formulated in the composition of the present invention differs depending on the type of the organic compound combined therewith and a property to be optimized and therefore, is not particularly limited. The amount is usually 0.01 to 80 parts by weight, preferably 0.1 to 60 parts by weight, with respect to 100 parts by weight in total of the composition of the present invention. The metal complex may be used alone or in combination of two or more of them.

<Device>

A device of the present invention contains the metal complex of the present invention and/or the polymer compound of the present invention and has, for example, electrodes comprising an anode (a positive electrode) and a cathode (a negative electrode), and a layer disposed between the electrodes, the layer containing the metal complex of the present invention and/or the polymer compound of the present invention.

Hereinafter, a light-emitting device as a typical example of the device of the present invention will be described.

The light-emitting device of the present invention comprises a pair of electrodes comprising an anode (a positive electrode) and a cathode (a negative electrode), and a thin film sandwiched between the electrodes, the thin film comprising one layer (single-layered) or plural layers (multilayered) having at least a light-emitting layer. At least one of the thin film layers contains the metal complex of the present invention and/or the polymer compound of the present invention. The total content of the metal complex of the present invention and/or the polymer compound of the present invention in the thin film is usually 0.1 to 100 wt %, preferably 0.1 to 30 wt %, more preferably 0.5 to 15 wt %, particularly preferably 1 to 10 wt %, with respect to the total weight of the light-emitting layer. For the light-emitting device of the present invention, it is preferred that the light-emitting layer should contain the metal complex of the present invention and/or the polymer compound of the present invention as light-emitting materials.

When the light-emitting device of the present invention takes the single-layered form, the thin film is a light-emitting layer, and this light-emitting layer contains the metal complex of the present invention. Alternatively, when the light-emitting device of the present invention takes the multilayered form, it has, for example, the following layer structures:

(a) anode/hole injection layer (hole transport layer)/light-emitting layer/cathode;
(b) anode/light-emitting layer/electron injection layer (electron transport layer)/cathode; and
(c) anode/hole injection layer (hole transport layer)/light-emitting layer/electron injection layer (electron transport layer)/cathode.

The anode in the light-emitting device of the present invention supplies holes to the hole injection layer, the hole transport layer, the light-emitting layer, or the like and effectively has a work function of 4.5 eV or higher. Metals, alloys, metal oxides, electroconductive compounds, and mixtures thereof, and so on can be used as materials for the anode. Specific examples thereof include: conductive metal oxides such as tin oxide, zinc oxide, indium oxide and indium tin oxide (ITO); metals such as gold, silver, chromium and nickel; mixtures or laminates with these conductive metal oxides and metals; inorganic conductive substances such as copper iodide and copper sulfide; organic conductive materials such as polyanilines, polythiophenes (PEDOT, etc.) and polypyrrole; and laminates of these conductive materials with ITO.

The cathode in the light-emitting device of the present invention supplies electrons to the electron injection layer, the electron transport layer, the light-emitting layer, or the like. Metals, alloys, metal halides, metal oxides, electroconductive compounds, and mixtures thereof can be used as materials for the cathode. Specific examples of the materials for the cathode include alkali metals (lithium, sodium, potassium, etc.) and fluorides and oxides thereof, alkaline-earth metals (magnesium, calcium, barium, cesium, etc.) and fluorides and oxides thereof, gold, silver, lead, aluminum, alloys and mixed metals (sodium-potassium alloy, sodium-potassium mixed metal, lithium-aluminum alloy, lithium-aluminum mixed metal, magnesium-silver alloy, magnesium-silver mixed metal, etc.) and rare-earth metals (indium, ytterbium, etc.).

The hole injection layer and the hole transport layer in the light-emitting device of the present invention need only to have any of the function of injecting holes from the anode, the function of transporting holes, and the function of blocking electrons injected from the cathode. Materials known in the art can be selected appropriately and used as materials for these layers. Specific examples thereof include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, poly(N-vinylcarbazole) derivatives, organic silane derivatives, the metal complex of the present invention, and polymers containing them. Other examples thereof include conductive polymer oligomers such as aniline copolymers, thiophene oligomers and polythiophene. These materials may comprise a single component alone or plural components in combination. Moreover, the hole injection layer and the hole transport layer may have a single-layered structure comprising one or two or more of the materials or may have a multilayered structure comprising plural layers with the same or different compositions.

The electron injection layer and the electron transport layer in the light-emitting device of the present invention need only to have any of the function of injecting electrons from the cathode, the function of transporting electrons, and the function of blocking holes injected from the anode. Materials known in the art can be selected appropriately and used for these layers. Specific examples thereof include triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, tetracarboxylic anhydrides having an aromatic ring (e.g., naphthalene and perylene), phthalocyanine derivatives, metal complexes of 8-quinolinol derivatives or various metal complexes typified by metal complexes having metallophthalocyanine, benzoxazole or benzothiazole as a ligand, organic silane derivatives and the metal complex compound of the present invention. Moreover, the electron injection layer and the electron transport layer may have a single-layered structure comprising one or two or more of the materials or may have a multilayered structure comprising plural layers with the same or different compositions.

Moreover, in the light-emitting device of the present invention, inorganic compounds serving as insulators or semiconductors can also be used as materials for the electron injection layer and the electron transport layer. The insulator or the semiconductor constituting the electron injection layer or the electron transport layer can effectively prevent current leakage and improve electron injection properties. At least one metal compound selected from the group consisting of alkali metal chalcogenide, alkaline-earth metal chalcogenide, alkali metal halides and alkaline-earth metal halides can be used as such an insulator. Specific examples of preferable alkali metal chalcogenide include CaO, BaO, SrO, BeO, BaS and CaSe. Moreover, examples of the semiconductor constituting the electron injection layer or the electron transport layer include oxides, nitrides or oxynitrides containing at least one element selected from the group consisting of Ba, Ca, Sr, Yb, Al, Ga, In, Li, Na, Cd, Mg, Si, Ta, Sb and Zn. These oxides, nitrides and oxynitrides may be used alone or in combination of two or more thereof.

In the present invention, a reducing dopant may be added to the interface region between the cathode and the thin film. The reducing dopant is preferably at least one compound selected from the group consisting of alkali metals, alkaline-earth metal oxides, alkaline-earth metals, rare-earth metals, alkali metal oxides, alkali metal halides, alkaline-earth metal oxides, alkaline-earth metal halides, rare-earth metal oxides, rare-earth metal halides, alkali metal complexes, alkaline-earth metal complexes and rare-earth metal complexes.

The light-emitting layer in the light-emitting device of the present invention has the function of capable of injecting holes from the anode or the hole injection layer and injecting electrons from the cathode or the electron injection layer upon voltage application, the function capable of moving the injected charges (electrons and holes) through the force of an electric field, and the function of providing a site for recombination of the electrons and the holes, which leads to light emission. It is preferred that the light-emitting layer in the light-emitting device of the present invention should contain at least the metal complex of the present invention and/or the polymer compound of the present invention. The light-emitting layer may contain a host material, with the metal complex and/or the polymer compound as guest materials. Examples of the host material include those having a fluorene skeleton, those having a carbazole skeleton, those having a diarylamine skeleton, those having a pyridine skeleton, those having a pyrazine skeleton, those having a triazine skeleton and those having an arylsilane skeleton. It is preferred that the host material should have larger T1 (energy level of a lowest triplet excited state) than that of the guest material. It is more preferred that the difference between them should be larger than 0.2 eV. The host material may be a low-molecular compound or a polymer compound. Moreover, the light-emitting layer comprising the light-emitting material doped into the host material can be formed, for example, by the application or codeposition of a mixture of the host material and the light-emitting material such as the metal complex.

In the light-emitting device of the present invention, a method for forming each of the layers is not particularly limited, and methods known in the art can be used. Specific examples thereof include vacuum deposition (resistance heating deposition, electron beam, etc.), sputtering, LB, molecular stacking and application (casting, spin coating, bar coating, blade coating, roll coating, gravure printing, screen printing, inkjet, etc.) methods. Among them, application is preferably used for film formation in terms of simplified production processes. In the application method, the metal complex of the present invention and/or the polymer compound of the present invention are dissolved in a solvent to prepare a coating solution, which can in turn be applied onto the desired layer (or electrode) and dried to form the thin film. The coating solution may contain the host material and/or a resin as a binder. The resin can be in a dissolved or dispersed state in a solvent. Non-conjugated polymers (e.g., polyvinylcarbazole) and conjugated polymers (e.g., polyolefin polymers) can be used as the resin. More specifically, the resin can be selected according to a purpose from, for example, polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resins, ketone resins, phenoxy resins, polyamide, ethylcellulose, vinyl acetate, ABS resins, polyurethane, melamine resins, unsaturated polyester resins, alkyd resins, epoxy resins and silicon resins. The solution may contain an antioxidant, a viscosity modifier, and so on as optional components according to a purpose.

—Photoelectric Device—

The metal complex and the polymer compound of the present invention can be used in the production of photoelectric devices.

The photoelectric device is, for example, a photoelectric conversion device. Specific examples thereof include: a device comprising a layer disposed between two electrodes, at least one of which is transparent or semitransparent, the layer containing the metal complex of the present invention and/or the polymer compound of the present invention; and a device having comb-shaped electrodes formed on a layer formed on a substrate, the layer containing the metal complex of the present invention and/or the polymer compound of the present invention. Fullerene, carbon nanotube, or the like may be mixed thereinto for improving the properties.

A method for producing the photoelectric conversion device is exemplified by a method described in Japanese Patent No. 3146296. Specifically, the method for producing the photoelectric conversion device is exemplified by: a method comprising forming a layer (thin film) containing the metal complex of the present invention and/or the polymer compound of the present invention on a substrate having a first electrode and forming a second electrode thereon; and a method comprising forming a layer (thin film) containing the metal complex of the present invention and/or the polymer compound of the present invention on a set of comb-shaped electrodes formed on a substrate. One of the first and second electrodes is transparent or semitransparent.

The method for forming the layer (thin film) containing the metal complex of the present invention and/or the polymer compound of the present invention or the method for mixing Fullerene or carbon nanotube thereinto is not particularly limited, and those exemplified for the light-emitting device can be used preferably.

<Liquid Composition>

A liquid composition of the present invention contains the metal complex of the present invention and/or the polymer compound of the present invention and a solvent or a dispersion medium. A solvent that is stable even when uniformly dissolving or dispersing therein components of a thin film can be selected appropriately from solvents known in the art and used as the solvent or the dispersion medium used in the liquid composition of the present invention. Examples of such a solvent include chlorine solvents (chloroform, methylene chloride, 1,2-dichloroethane, 1,1,2-trichloroethane, chlorobenzene, o-dichlorobenzene, etc.), ether solvents (tetrahydrofuran, dioxane, etc.), aromatic hydrocarbon solvents (benzene, toluene, xylene, etc.), aliphatic hydrocarbon solvents (cyclohexane, methylcyclohexane, n-pentane, n-hexane, n-heptane, n-octane, n-nonane, n-decane, etc.), ketone solvents (acetone, methyl ethyl ketone, cyclohexanone, etc.), ester solvents (ethyl acetate, butyl acetate, ethyl cellosolve acetate, etc.), polyhydric alcohols and derivatives thereof (ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol, etc.), alcoholic solvents (methanol, ethanol, propanol, isopropanol, cyclohexanol, etc.), sulfoxide solvents (dimethyl sulfoxide, etc.) and amide solvents (N-methyl-2-pyrrolidone, N,N-dimethylformamide, etc.). These solvents may be used alone or in combination of two or more thereof.

When the liquid composition is applied to an inkjet method, the liquid composition may contain an additive known in the art for enhancing the discharge properties of the liquid composition and reproducibility thereof. Examples of this additive known in the art include high-boiling solvents (anisole, bicyclohexylbenzene, etc.) for reducing vaporization from a nozzle. In addition, it is preferred that the liquid composition containing this additive known in the art should have a viscosity of 1 to 100 mPa·s at 25° C.

The preferable film thickness of each layer in the light-emitting device of the present invention differs depending on the type of the material and a layer structure and is not particularly limited. In general, too thin a film thickness tends to cause defects such as pinholes, whereas too thick a film thickness requires a high applied voltage, resulting in poor luminous efficiency. Therefore, the film thickness is preferably a few nm to 1 μm.

The use of the light-emitting device of the present invention is not particularly limited. Examples thereof include planar light sources, light sources for illumination (or light sources), light sources for signs, light sources for backlights, display devices and printer heads. The display devices can have a structure selected from a segment structure, a dot matrix structure, or the like using a drive technique, a drive circuit, and so on known in the art.

<Other Uses>

The metal complex of the present invention and the polymer compound of the present invention are not only useful in the preparation of devices but also can be used as a semiconductor material (e.g., an organic semiconductor material), a light-emitting material, an optical material, a conductive material (e.g., which is applied by doping), or the like. Thus, the metal complex and the polymer compound can be used to prepare films such as light-emitting films, conductive films and organic semiconductor films (i.e., films containing the metal complex and/or the polymer compound).

The metal complex of the present invention and the polymer compound of the present invention can be used to form conductive thin films and semiconductor thin films and make them into devices in the same way as in the method for preparing a light-emitting film used as the light-emitting layer in the light-emitting device. For the semiconductor thin films, it is preferred that, of electron mobility and hole mobility, the larger one should have $10^{-5}$ cm$^2$/V/second or larger. Moreover, the organic semiconductor films can be used in organic solar cells, organic transistors, and so on.

EXAMPLES

Hereinafter, the present invention will be described more specifically with reference to Examples. However, the present invention is not intended to be limited to them.

Example 1

Synthesis of Metal Complex (MC-1)

A solution containing a metal complex (MC-1) and an organic solvent is prepared, and its photoluminescence is measured. As a result, light emission is observed.

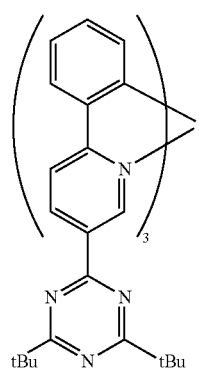

(MC-1)

Example 2

Synthesis of Metal Complex (MC-2)

Synthesis of 5-bromo-2-phenylpyridine

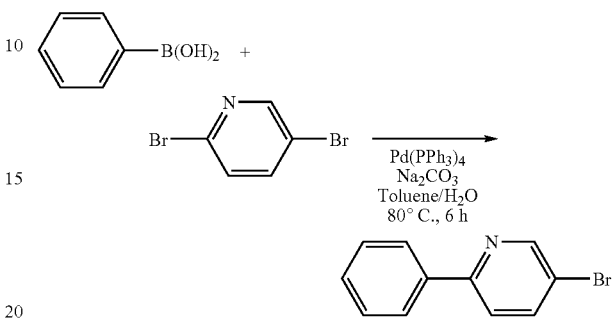

2,5-dibromopyridine (7.11 g, 30 mmol), toluene (130 mL), phenylboronic acid (4.57 g, 37.5 mmol) and tetrakis(triphenylphosphine)palladium(0) (1.73 g, 1.5 mmol) were weighed into a reaction vessel, and the reaction mixture was dissolved with stirring at 50° C. in a nitrogen stream. To this solution, a 2 M aqueous sodium carbonate solution (30 mL) was added, and the mixture was stirred at 80° C. for 6 hours. The organic layer of the obtained reaction solution was collected and washed with an aqueous sodium carbonate solution and a saturated brine. The organic layer was dried over sodium sulfate, filtered, and evaporated to dryness. This residue was purified by silica gel column chromatography (hexane/toluene). The eluate was evaporated to obtain 5-bromo-2-phenylpyridine (6.21 g, 26.5 mmol).

Synthesis of Metal Complex (Complexes 1 and 2)

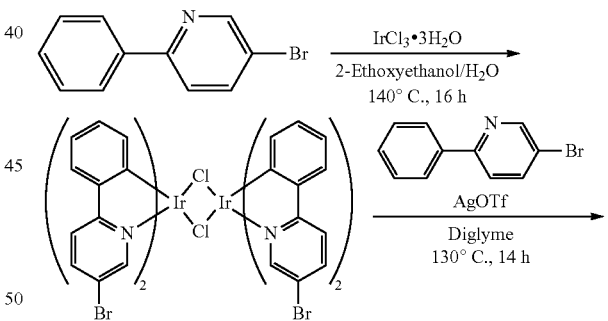

complex 1

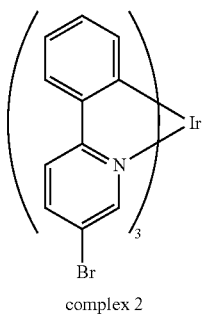

complex 2

5-bromo-2-phenylpyridine (7.39 g, 30 mmol), iridium chloride trihydrate (4.76 g, 13.5 mmol), 2-ethoxyethanol (58 mL) and water (19 mL) were weighed into a reaction vessel and heated at 140° C. for 16 hours in a nitrogen stream. After air cooling, the obtained reaction mixture was filtered, and the solid was washed with water, methanol and hexane in this order to obtain a metal complex represented by the formula (complex 1, 9.10 g, 6.58 mmol) as a yellow solid.

The metal complex (complex 1, 6.94 g, 5.0 mmol), 5-bromo-2-phenylpyridine (7.32 g, 30.0 mmol) and diglyme (43 mL) were weighed into a reaction vessel. Silver trifluoromethanesulfonate (2.57 g, 10.0 mmol) was added thereto, and the mixture was stirred at 130° C. for 14 hours. The obtained reaction mixture was filtered, and the solid was dissolved in methylene chloride (1.3 L). This solution was filtered, and the filtrate was concentrated to approximately 150 mL. The deposited solid was collected by filtration and washed with hexane to obtain a metal complex represented by the formula (complex 2, 6.35 g, 7.1 mmol).

LC-MS (positive) m/z: 890 ([M+H]$^+$)

$^1$H NMR (300 MHz, DMSO-d$_6$)

δ 6.51 (d, J=7.8 Hz, 3H), δ 6.72 (m, 3H), δ 6.84 (m, 3H), δ 7.66 (d, J=2.0 Hz, 3H), δ 7.80 (d, J=7.8 Hz, 3H), δ 8.05 (dd, J=2.0, 8.8 Hz, 3H), δ 8.14 (d, J=8.8 Hz, 3H)

Synthesis of Metal Complex (Complex 3)

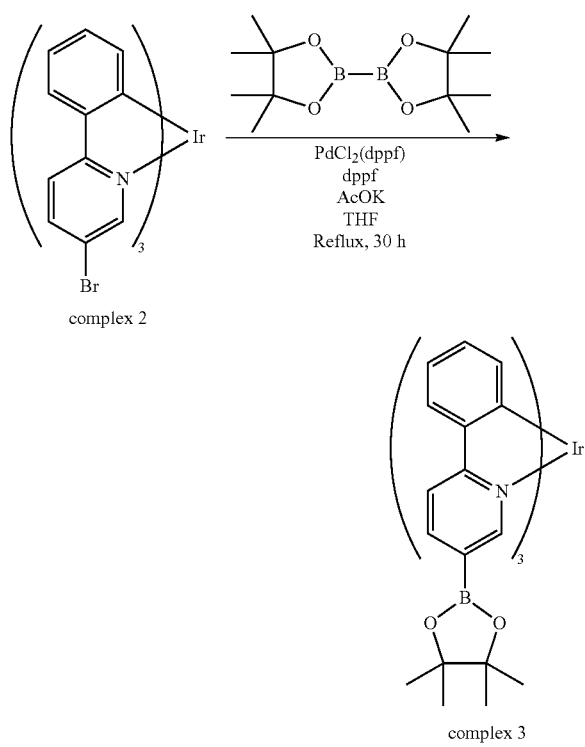

complex 3

The metal complex (complex 2, 3.27 g, 3.7 mmol), potassium acetate (3.27 g, 33.3 mmol), bis(pinacolato)diboron (3.38 g, 13.3 mmol), 1,1'-bis(diphenylphosphino)ferrocene (245 mg, 0.44 mmol), [1,1'-bis(diphenylphosphino)ferrocene]dichloropalladium(II) (361 mg, 0.44 mmol) and tetrahydrofuran (400 mL) were weighed into a reaction vessel in a nitrogen stream and refluxed for 30 hours. The obtained reaction solution was concentrated and dissolved by the addition of methylene chloride (150 mL). Then, the solution was filtered. This filtrate was purified by silica gel chromatography (methylene chloride). The eluate was evaporated, and the residue was washed with diethyl ether to obtain a metal complex represented by the formula (complex 3, 2.55 g, 2.47 mmol).

LC-MS (positive) m/z: 1072 ([M+K]$^+$)

$^1$H NMR (300 MHz, CDCl$_3$)

δ 1.21 (s, 36H), δ 6.87 (m, 9H), δ 7.69 (d, J=7.7 Hz, 3H), δ 7.82 (s, 3H), δ 7.86 (m, 6H)

Synthesis of 2-chloro-4,6-di(4$^1$-tert-butyl)phenylpyrimidine

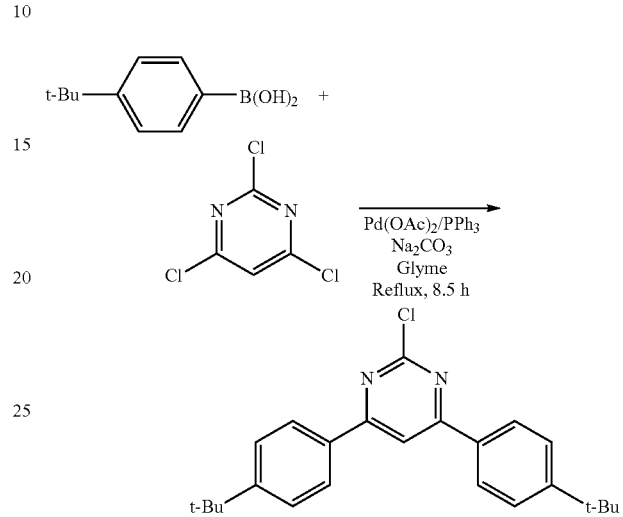

cyanuric chloride (1.83 g, 10 mmol), 4-tert-butylphenylboronic acid (3.73 g, 21 mmol), sodium carbonate (6.57 g, 62 mmol), palladium acetate (89 mg, 0.40 mmol), triphenylphosphine (0.21 g, 0.80 mmol), glyme (50 mL) and water (20 mL) were charged into a reaction vessel in a nitrogen stream and refluxed for 8.5 hours. The obtained reaction mixture was evaporated, then, chloroform (50 mL) was added. The organic layer was extracted, dried over magnesium sulfate and filtered. The filtrate was evaporated to dryness. This residue was purified twice by silica gel chromatography (hexane/toluene). The eluate was evaporated to obtain 2-chloro-4,6-di(4'-tert-butyl)phenylpyrimidine (2.64 g, 7.0 mmol).

LC-MS (APPI, positive) m/z: 379.2 ([M+H]$^+$)

$^1$H NMR (300 MHz, CDCl$_3$)

δ 1.38 (s, 18H), δ 7.55 (d, J=6.9 Hz, 4H), δ 7.97 (s, 1H), δ 8.07 (d, J=6.9 Hz, 4H)

Synthesis of Metal Complex (MC-2)

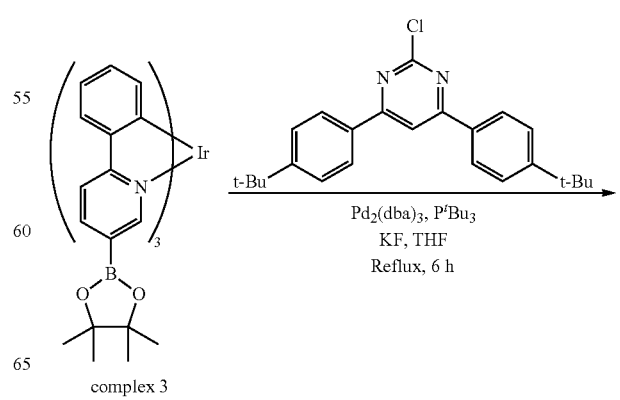

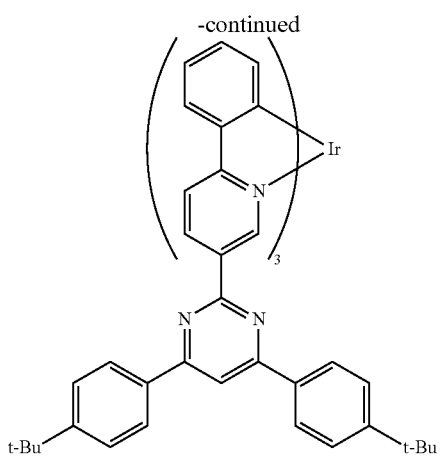

The metal complex represented by the formula (complex 3, 103 mg, 0.10 mmol), 2-chloro-4,6-di(4'-tert-butyl)phenylpyrimidine (125 mg, 0.33 mmol), potassium fluoride (58 mg, 1.0 mmol), tris(dibenzylideneacetone)dipalladium(0) (13.7 mg, 0.015 mmol) and tetrahydrofuran (10 mL) were weighed into a reaction vessel in a nitrogen stream. Tri-tert-butylphosphine (7.3 μL) was added thereto, and the mixture was refluxed for 6 hours. The obtained reaction solution was concentrated, dissolved in toluene, and dried over sodium sulfate. This organic layer was purified by silica gel chromatography (toluene), and the eluate was evaporated to dryness. The residue was washed with methanol to obtain a metal complex (MC-2) represented by the following formula:

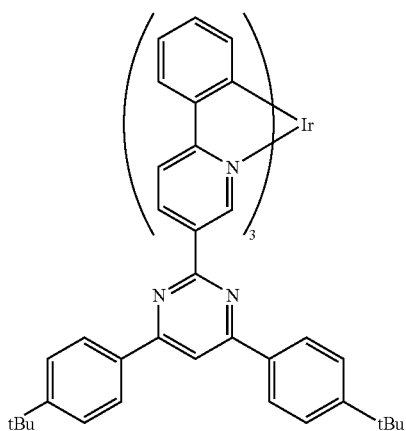

(MC-2)

(69.8 mg, 0.042 mmol).

LC-MS (APCI, positive) m/z: 1683 ([M+H]$^+$)

$^1$H NMR (300 MHz, CDCl$_3$)

δ 1.19 (s, 54H), δ 6.93 (m, 9H), δ 7.41 (d, J=8.4 Hz, 12H), δ 7.79 (d, J=7.5 Hz, 3H), δ 7.82 (s, 3H), δ 7.90 (d, J=8.4 Hz, 12H), δ 8.12 (d, J=8.4 Hz, 3H), δ 9.12 (d, J=8.4 Hz, 3H), δ 9.34 (s, 3H)

Physical Property Measurement of Metal Complex (MC-2)

The metal complex (MC-2) and a polymethyl methacrylate resin (manufactured by Sigma-Aldrich, Inc.) (hereinafter, referred to as "PMMA") were mixed at a weight ratio of 2:98 and prepared into a 10 wt % chloroform solution. This solution was added dropwise onto a quartz substrate and dried to form a metal complex (MC-2)-doped PMMA film on the quartz substrate. The obtained substrate was used to measure photoluminescence. As a result, light emission with a peak at 575 nm was observed, and the quantum yield was 80%. The photoluminescence quantum yield was measured at an excitation wavelength of 325 nm using an organic EL emission property evaluation apparatus (manufactured by OPTEL Co., Ltd., trade name: IES-150).

Example 3

Synthesis of Metal Complex (MC-3)

Synthesis of 2,4-dichloro-6-(4-tert-butyl)phenylpyrimidine

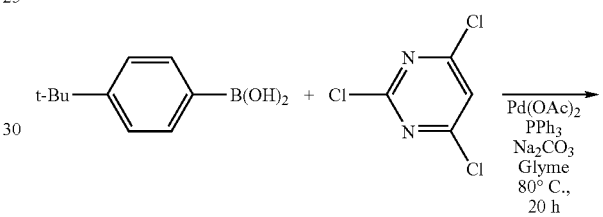

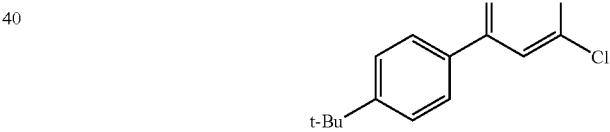

2,4,6-trichloropyrimidine (18.3 g, 100 mmol), 4-tert-butylphenylboronic acid (37.4 g, 210 mmol), sodium carbonate (65.7 g, 620 mmol), palladium acetate (0.56 g, 2.5 mmol), triphenylphosphine (1.31 g, 5.0 mmol) and glyme (500 mL) were charged into a reaction vessel in a nitrogen stream and refluxed at 80° C. for 20 hours. The obtained reaction mixture was evaporated, then ethyl acetate (200 mL) and water (200 mL) were added. The organic layer was extracted, dried over magnesium sulfate and filtered. The filtrate was evaporated to dryness. This residue was purified by silica gel chromatography (hexane/ethyl acetate), and the eluate was evaporated to dryness. This residue was recrystallized from hexane to obtain 2,4-dichloro-6-(4-tert-butyl)phenylpyrimidine (2.0 g, 7.1 mmol).

LC-MS (positive) m/z: 281 ([M+H]$^+$)

$^1$H NMR (300 MHz, CDCl$_3$)

δ 1.36 (s, 9H), δ 7.54 (d, J=6.9 Hz, 2H), δ 7.64 (s, 1H), δ 8.01 (d, J=6.9 Hz, 2H)

Synthesis of Metal Complex (MC-3)

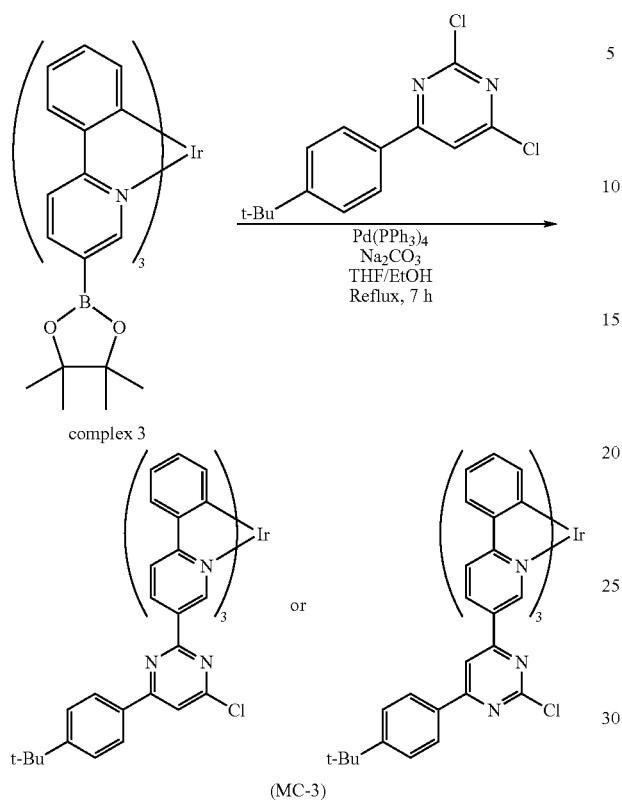

The metal complex (complex 3, 341 mg, 0.33 mmol), 2,4-dichloro-6-(4-tert-butyl)phenylpyrimidine (540 mg, 1.7 mmol), potassium carbonate (547 mg, 3.9 mmol), tetrakis(triphenylphosphine)palladium(0) (97 mg, 0.084 mmol), tetrahydrofuran (60 mL) and ethanol (10 mL) were weighed into a reaction vessel in a nitrogen stream and refluxed for 7 hours. The obtained reaction solution was filtered. The filtrate was concentrated, and methanol (50 mL) was added thereto. The formed precipitate was collected by filtration, dissolved in methylene chloride, and the solution was dried over sodium sulfate. This solution was filtered. Then, this filtrate was purified twice by silica gel chromatography (first: methylene chloride, second: toluene), and the eluent was evaporated to dryness. The residue was washed with methanol and hexane to obtain a metal complex represented by the formula (MC-3, 56.0 mg, 0.040 mmol).

LC-MS (positive) m/z: 1388 ([M+H]$^+$)

$^1$H NMR (300 MHz, CDCl$_3$)

δ 1.31 (s, 27H), δ 6.99 (m, 6H), δ 7.08 (m, 3H), δ 7.42 (d, J=6.8 Hz, 6H), δ 7.55 (s, 3H), δ 7.80 (m, 9H), δ 8.05 (d, J=8.4 Hz, 3H), δ 8.40 (m, 6H)

Physical Property Measurement of Metal Complex (MC-3)

The metal complex (MC-3) was dissolved at a concentration of 2 wt % in a 10 wt % toluene solution of a polymethyl methacrylate resin (manufactured by Sigma-Aldrich, Inc.) to prepare a solution. This solution was added dropwise onto a quartz substrate and dried to form a metal complex (MC-3)-doped PMMA film on the quartz substrate. The obtained substrate was used to measure photoluminescence. As a result, light emission with a peak at 630 nm was observed, and the quantum yield was 65%. The photoluminescence quantum yield was measured at an excitation wavelength of 325 nm using an organic EL emission property evaluation apparatus (manufactured by OPTEL Co., Ltd., trade name: IES-150).

Example 4

Synthesis of Metal Complex (MC-4)

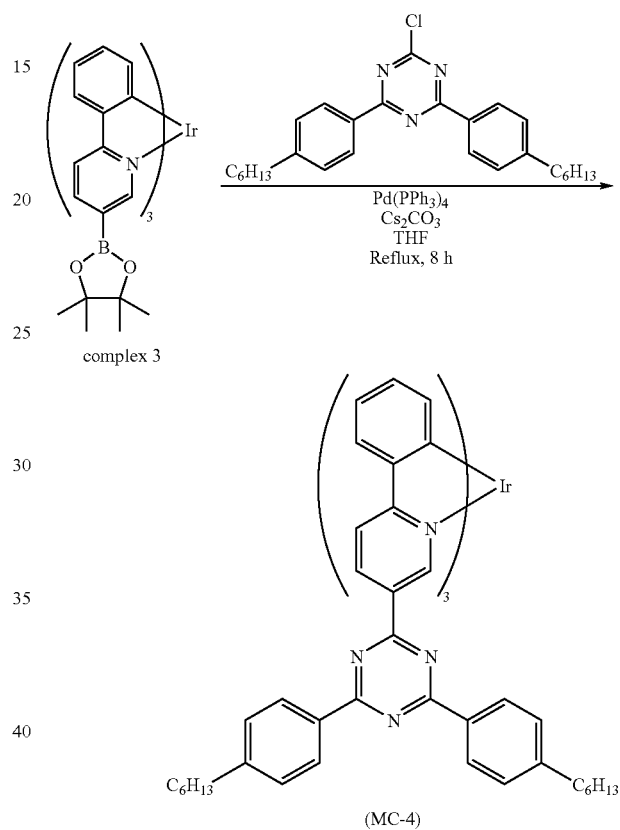

The metal complex (complex 3, 929 mg, 0.90 mmol), 2-chloro-4,6-di(4'-hexylphenyl)-1,3,5-triazine (1.29 g, 3.0 mmol), cesium carbonate (2.93 g, 9.0 mmol), tetrakis(triphenylphosphine)palladium(0) (312 mg, 0.27 mmol) and tetrahydrofuran (90 mL) were weighed into a reaction vessel in a nitrogen stream and refluxed for 8 hours. To the obtained reaction mixture, toluene was added. The solution was filtered, and the filtrate was concentrated. This toluene solution was purified three times by silica gel chromatography (developing solvent in the first run: toluene/eluent in the second and third runs: hexane/toluene=1/1), and the eluate was evaporated to dryness. This residue was washed with methanol to obtain a metal complex represented by the formula (MC-4) (227 mg, 0.12 mmol).

LC-MS (APCI, positive) m/z: 1854 ([M+H]$^+$)

$^1$H NMR (300 MHz, CDCl$_3$)

δ 0.88 (t, J=6.6 Hz, 18H), δ 1.22 (m, 36H), δ 1.49 (m, 12H), δ 2.48 (m, 12H), δ 6.96 (m, 9H), δ 7.22 (d, J=7.8 Hz, 12H), δ 7.83 (d, J=7.5 Hz, 3H), δ 8.18 (d, J=8.4 Hz, 3H), δ 8.35 (d, J=7.8 Hz, 12H), δ 9.19 (d, J=8.4 Hz, 3H), δ 9.31 (s, 3H)

Physical Property Measurement of Metal Complex (MC-4)

The metal complex (MC-4) and PMMA were mixed at a weight ratio of 2:98 and prepared into a 10 wt % chloroform solution. This solution was added dropwise onto a quartz substrate and dried to form a metal complex (MC-4)-doped PMMA film on the quartz substrate. The obtained substrate was used to measure photoluminescence. As a result, light emission with a peak at 605 nm was observed, and the quantum yield was 88%.

Synthesis of Compound (P-1)

9,9-dioctylfluorene-2,7-diboronic acid ethylene glycol ester (3.18 g, 6.0 mmol), 9,9-dioctyl-2,7-dibromofluorene (3.06 g, 5.4 mmol), N,N'-bis(4-bromophenyl)-N,N'-bis(2,6-dibromo-4-tert-butylphenyl)-1,4-phenylenediamine (0.44 g, 0.6 mmol), methyltrioctylammonium chloride (trade name: Aliquat 336, manufactured by Sigma-Aldrich, Inc., 0.82 g) and toluene (60 mL) were added to a 200-mL separable flask connected with a Dimroth condenser. Bis(triphenylphosphine)palladium dichloride (4.2 mg) was added thereto under a nitrogen atmosphere, and the mixture was heated to 85° C. To the obtained solution, a 17.5 wt % aqueous sodium carbonate solution (16.3 mL) was added dropwise, while the mixture was heated to 105° C. and then stirred for 1.5 hours. Next, phenylboronic acid (0.74 g), bis(triphenylphosphine)palladium dichloride (4.2 mg) and toluene (30 mL) were added thereto, and the mixture was stirred at 105° C. for 17 hours.

After removal of the aqueous layer from the obtained solution, sodium N,N-diethyldithiocarbamate trihydrate (3.65 g) and ion-exchanged water (36 mL) were added to the solution, and the mixture was stirred at 85° C. for 2 hours. The organic layer was separated from the aqueous layer and then washed with ion-exchanged water (80 mL, twice), a 3 wt % aqueous acetic acid solution (80 mL, twice) and ion-exchanged water (80 mL, twice) in this order.

The organic layer was added dropwise to methanol (930 mL) to precipitate a polymer. The precipitate was collected by filtration and then dried to obtain a solid. This solid was dissolved in toluene (190 mL), and the solution was passed through a silica gel/alumina column through which toluene was flowed in advance. This solution was added dropwise to methanol (930 mL) to precipitate a polymer. The precipitate was collected by filtration and then dried to obtain a compound represented by the following formula:

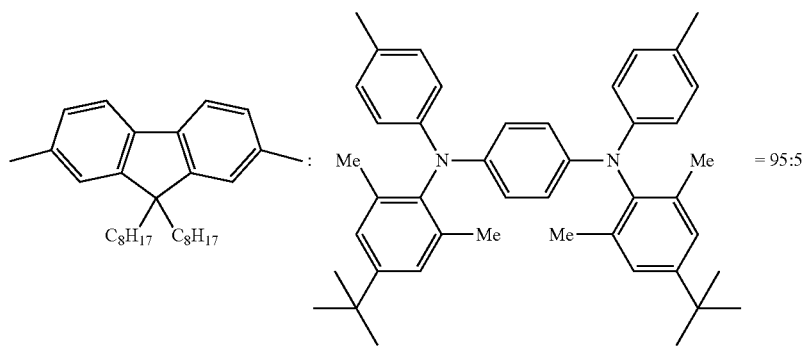

(P-1, 4.17 g). This compound (P-1) had a number-average molecular weight Mn of $2.7 \times 10^5$ based on polystyrene standards and a weight-average molecular weight Mw of $7.1 \times 10^5$ based on polystyrene standards.

The metal complex (MC-4) was added at a proportion of 5 wt % to the compound (P-1), and the mixture was prepared into a 1.0 wt % xylene solution. In addition, the following polymer (TFB) was prepared into a 0.5 wt % xylene solution:

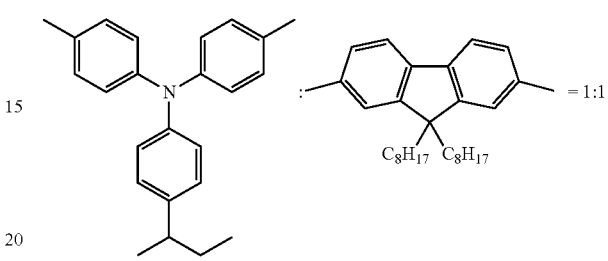

A film of a poly(ethylenedioxythiophene)/polystyrene sulfonic acid solution (Bayer AG, trade name: Baytron P) was formed at a thickness of 50 nm by spin coating on a glass substrate coated with an ITO film at a thickness of 150 nm by a sputtering method. The film was dried at 200° C. for 10 minutes on a hot plate. Next, a film of the xylene solution of TFB thus prepared was formed thereon at a rotation speed of 2000 rpm by spin coating and dried at 180° C. for 15 minutes in a nitrogen gas atmosphere. This substrate was cooled to room temperature. Then, a film of the mixed xylene solution of the metal complex (MC-4) and the compound (P-1) thus prepared was formed thereon at a rotation speed of 2000 rpm by spin coating. The obtained film had an average film thickness of approximately 100 nm. This film was dried at 130° C. for 10 minutes in a nitrogen gas atmosphere. Then, barium (approximately 5 nm) and subsequently aluminum (approximately 80 nm) were deposited thereonto as a cathode to prepare an EL device. In this context, the metal deposition was started after the degree of vacuum reached $1 \times 10^{-4}$ Pa or lower. To the obtained device, a voltage was applied to obtain red EL emission with a peak at 605 nm. The luminous efficiency was 7.8 cd/A at the maximum.

Furthermore, this device was driven for 50 hours at a constant current, with initial brightness set to 4000 cd/m². As a

Example 5

Synthesis of Metal Complex (MC-5)

Synthesis of 2,4-di(4'-tert-butylphenyl)-6-chloro-1,3,5-triazine

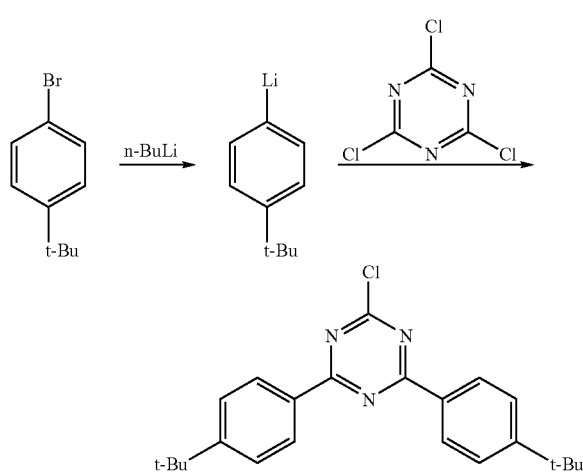

1-bromo-4-tert-butylbenzene (125 g, 587 mmol) and tetrahydrofuran (470 mL) were charged into a reaction vessel in an argon stream and cooled to −70° C. A n-butyllithium/hexane solution (1.6 M, 367 mL, 587 mmol) was added dropwise thereto at −70° C. over 90 minutes. After the completion of dropwise addition, the mixture was stirred at −70° C. for 2 hours to obtain a 4-tert-butylphenyllithium/THF solution. Cyanuric chloride (50.8 g, 276 mmol) and tetrahydrofuran (463 mL) were charged into another reaction vessel in an argon stream and cooled to −70° C. The 4-tert-butylphenyllithium/THF solution thus prepared was gradually added dropwise thereto, while cooled to keep the reaction temperature to −60° C. or lower. After the completion of dropwise addition, the reaction solution was stirred at −40° C. for 4 hours and at room temperature for 4 hours. The mixture was quenched by addition of water (50 mL), and tetrahydrofuran was evaporated. From this residue, the organic layer was extracted by the addition of water (1 L) and chloroform (2 L) and the organic layer was washed with water (1 L), and evaporated to dryness. This residue was dissolved in acetonitrile (600 mL), and insoluble solid was filtered off hot. The obtained filtrate was concentrated to approximately 100 mL and cooled to −70° C., and the deposited solid was collected by filtration. The collected solid was dissolved in a chloroform (200 mL)/hexane (600 mL) mixed solvent and purified by silica gel column chromatography (eluent: chloroform/hexane). The eluate was evaporated to dryness, and this residue was recrystallized from acetonitrile to obtain 2,4-di(4'-tert-butylphenyl)-6-chloro-1,3,5-triazine (41.3 g, 109 mmol).

LC-MS (APPI, positive) m/z: 380 ([M+H]$^+$)

$^1$H NMR (300 MHz, CDCl$_3$)

δ 1.39 (s, 18H), δ 7.56 (d, J=8.4 Hz, 4H), δ 8.54 (d, J=8.4 Hz, 4H)

Synthesis of Metal Complex (MC-5)

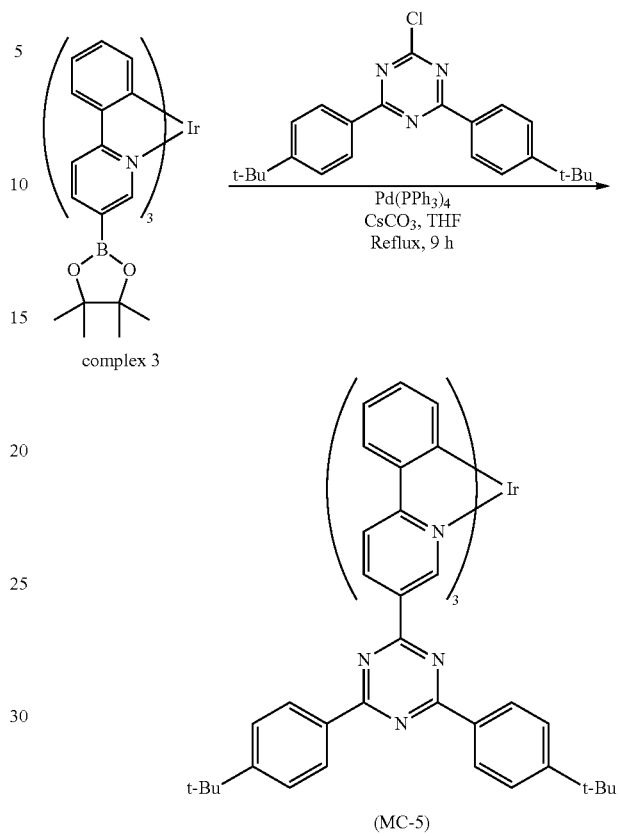

The metal complex (complex 3, 546 mg, 0.53 mmol), 2,4-di(4'-tert-butylphenyl)-6-chloro-1,3,5-triazine (702 mg, 1.85 mmol), cesium carbonate (1.73 g, 5.31 mmol), tetrakis (triphenylphosphine)palladium(0) (196 mg, 0.17 mmol) and tetrahydrofuran (53 mL) were weighed into a reaction vessel in a nitrogen stream and refluxed for 9 hours. The obtained reaction solution was concentrated and dissolved by the addition of toluene. This solution was filtered, and the filtrate was purified twice by silica gel chromatography (eluent in the first run: toluene, eluent in the second run: hexane/toluene=1/1). The eluate was evaporated to dryness, and the residue was washed with methanol to obtain a metal complex represented by the formula (MC-5, 257 mg, 0.15 mmol).

LC-MS (APCI, positive) m/z: 1686 ([M+H]$^+$)

$^1$H NMR (300 MHz, CDCl$_3$)

δ 1.14 (s, 54H), δ 6.96 (m, 9H), δ 7.39 (d, J=8.4 Hz, 12H), δ 7.83 (d, J=7.5 Hz, 3H), δ 8.18 (d, J=8.4 Hz, 3H), δ 8.36 (d, J=8.4 Hz, 12H), δ 9.14 (d, J=8.4 Hz, 3H), δ 9.33 (s, 3H)

Physical Property Measurement of Metal Complex (MC-5)

The metal complex (MC-5) was dissolved at a concentration of 2 wt % in a 10 wt % toluene solution of a polymethyl methacrylate resin (manufactured by Sigma-Aldrich, Inc.) to prepare a solution. This solution was added dropwise onto a quartz substrate and dried to form a metal complex (MC-5)-doped PMMA film on the quartz substrate. The obtained substrate was used to measure photoluminescence. As a result, light emission with a peak at 610 nm was observed, and the quantum yield was 89%.

An EL device was prepared in the same way as in Example 4 except that the metal complex (MC-5) was used instead of the metal complex (MC-4) in Example 4.

To the obtained EL device, a voltage was applied to obtain red EL emission with a peak at 620 nm. The luminous efficiency was 6.9 cd/A at the maximum. This device was driven for 50 hours, with initial brightness set to 4000 cd/m². As a result, the device maintained 73% brightness with respect to the initial brightness and was thus had a long lifetime.

Example 6

Synthesis of Metal Complex (MC-6)

Synthesis of 2-(4'-benzoylphenyl)-5-bromopyridine

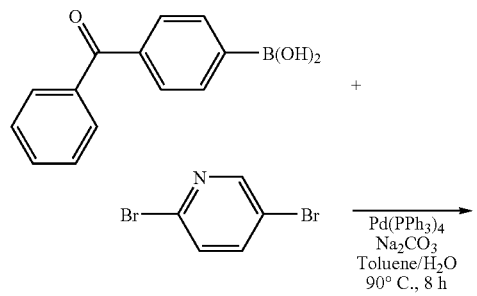

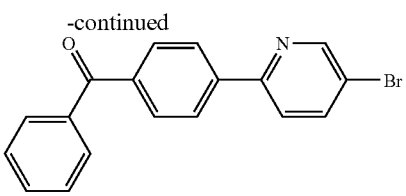

2,5-dibromopyridine (15.85 g, 66.0 mmol) was weighed into a reaction vessel in an argon stream and prepared into a solution by the addition of toluene (300 mL). 4-benzoylphenylboronic acid (18.86 g, 83.0 mmol), tetrakis(triphenylphosphine)palladium(0) (3.05 g, 2.6 mmol) and a 1.41 M aqueous sodium carbonate solution (100 mL) were added thereto, and the mixture was stirred at 90° C. for 8 hours. From the obtained reaction mixture, the solid was collected by filtration. This solid was washed with cold toluene and cold diethyl ether in this order. This solid was dissolved in a toluene/chloroform mixed solvent (volume ratio: 2/1) and purified by silica gel column chromatography. The eluate was evaporated to dryness, and the obtained residue was dissolved in a chloroform/ethanol mixed solvent (volume ratio: 9/2) and recrystallized several times to obtain 2-(4'-benzoylphenyl)-5-bromopyridine (3.00 g, 8.87 mmol) as a yellow solid.

¹H NMR (300 MHz, CDCl₃)
δ 7.49-7.92 (m, 9H), δ 8.08 (d, J=7.8 Hz, 2H), δ 8.77 (s, 1H)
¹³C NMR (75 MHz, CDCl₃)
δ 120.5, δ 122.9, δ 126.9, δ 128.6, δ 130.3, δ 130.9, δ 132.8, δ 137.7, δ 138.3, δ 139.8, δ 142.0, δ 151.2, δ 154.9, δ 196.5

Synthesis of Metal Complex (Complexes 4 and 5)

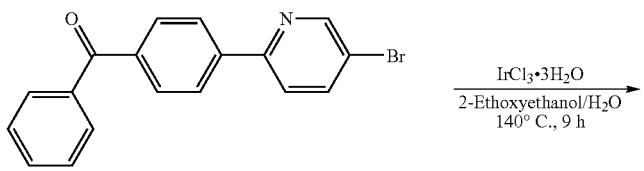

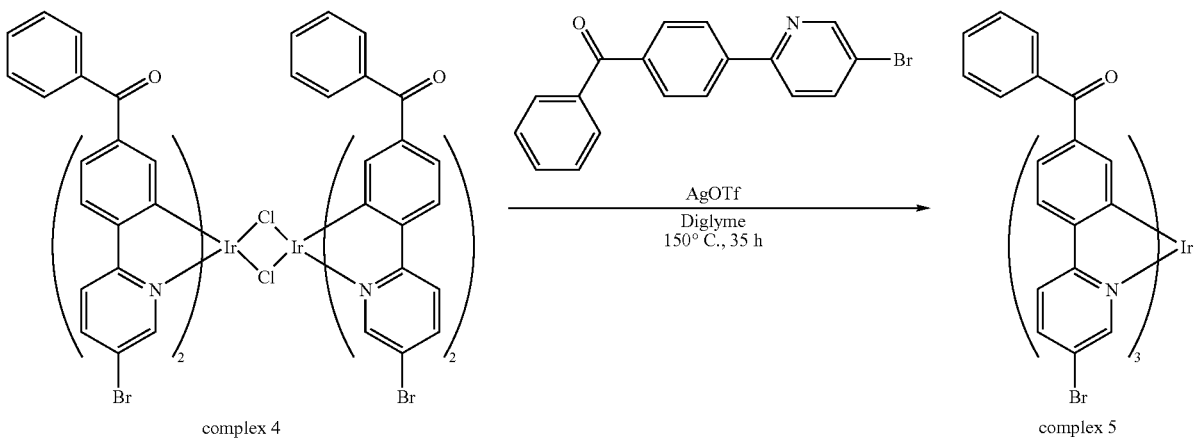

complex 4 complex 5

2-(4'-benzoylphenyl)-5-bromopyridine (1.01 g, 3.0 mmol), iridium chloride trihydrate (0.48 g, 1.4 mmol), 2-ethoxyethanol (12 mL) and water (4 mL) were weighed into a reaction vessel and heated at 140° C. for 9 hours in a nitrogen stream. After air cooling, the obtained reaction mixture was filtered, and the solid was washed with methanol and hexane in this order to obtain a metal complex represented by the formula (complex 4, 1.23 g, 0.68 mmol) as an orange solid.

The metal complex (complex 4, 1.23 g, 0.68 mmol), 2-(4'-benzoylphenyl)-5-bromopyridine (1.38 g, 4.1 mmol) and diglyme (12 mL) were weighed into a reaction vessel. Silver trifluoromethanesulfonate (0.35 g, 1.4 mmol) was added thereto, and the mixture was stirred at 150° C. for 35 hours. The obtained reaction mixture was filtered, and the solid was dissolved in methylene chloride (100 mL). This solution was filtered, and the solvent was distilled off from the filtrate. This residue was washed with methanol and hexane in this order to obtain a metal complex represented by the formula (complex 5, 1.26 g, 1.05 mmol).

LC-MS (APPI, positive) m/z: 1203.9 ([M+H]$^+$)

$^1$H NMR (300 MHz, CDCl$_3$)

δ 7.02 (s, 3H), δ 7.19 (dd, J=7.1, 7.5 Hz, 6H), δ 7.35 (m, 12H), δ 7.64 (s, 3H), δ 7.67 (d, J=8.1 Hz, 3H), δ 7.89 (dd, J=6.9, 8.8 Hz, 6H)

$^{13}$C NMR (75 MHz, CDCl$_3$)

δ 119.1, δ 121.3, δ 123.0, δ 124.5, δ 128.1, δ 130.1, δ 132.1, δ 137.9, δ 138.3, δ 138.9, δ 140.3, δ 146.5, δ 148.6, δ 157.6, δ 164.3, δ 197.4

Synthesis of Metal Complex (Complex 6)

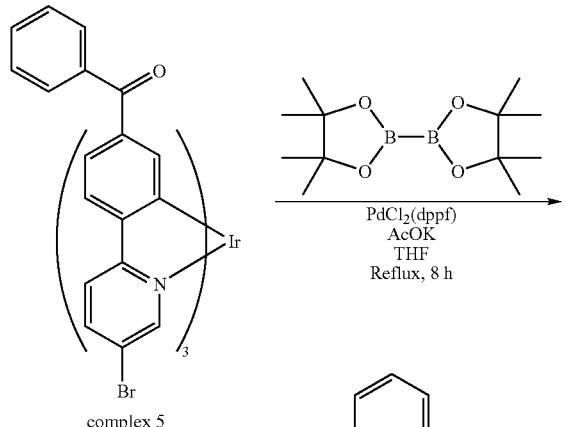

The metal complex (complex 5, 1.21 g, 1.0 mmol), potassium acetate (1.10 g, 11.2 mmol), bis(pinacolato)diboron (1.19 g, 4.2 mmol), [1,1'-bis(diphenylphosphino)ferrocene]dichloropalladium(II) (0.32 g, 0.35 mmol) and tetrahydrofuran (100 mL) were weighed into a reaction vessel in a nitrogen stream and refluxed for 8 hours. The obtained reaction solution was concentrated and dissolved by the addition of methylene chloride. Then, the solution was filtered. This filtrate was purified by silica gel chromatography (methylene chloride/methanol=10/1), and the eluate was evaporated to dryness. This residue was washed with methanol and hexane in this order to obtain a metal complex represented by the formula (complex 6, 0.62 g, 0.46 mmol).

LC-MS (APPI, positive) m/z: 1346.4 ([M+H]$^+$)

$^1$H NMR (300 MHz, CDCl$_3$)

δ 1.24 (s, 36H), δ 7.17 (m, 9H), δ 7.34 (m, 12H), δ 7.73 (d, J=8.1 Hz, 3H), δ 7.84 (s, 3H), δ 7.95 (d, J=8.1 Hz, 3H), δ 8.02 (d, J=8.1 Hz, 3H)

Synthesis of Metal Complex (MC-6)

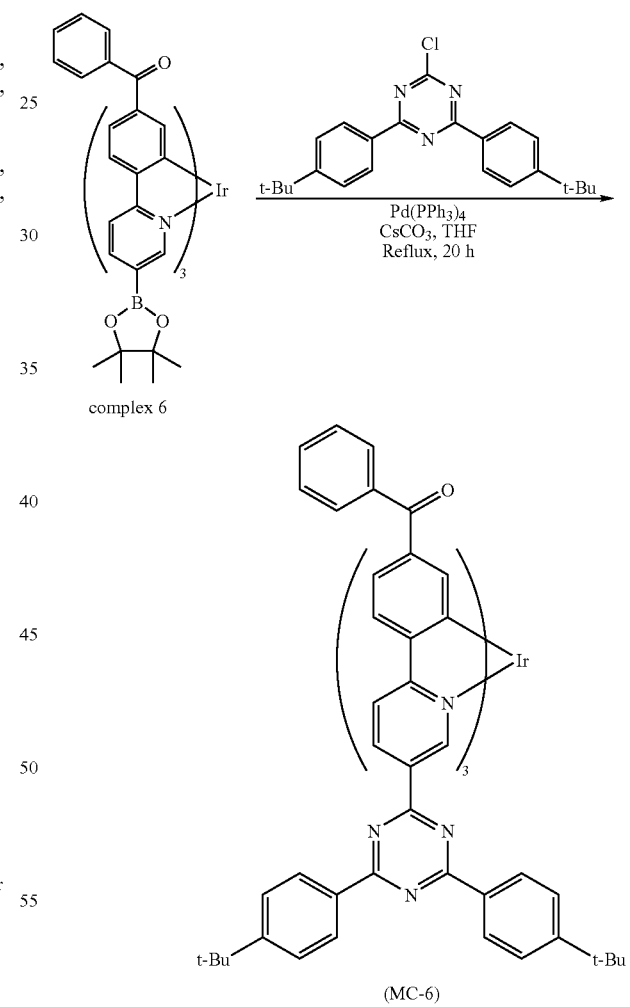

The metal complex (complex 6, 460 mg, 0.342 mmol), 2,4-di(4'-tert-butylphenyl)-6-chloro-1,3,5-triazine (456 mg, 1.20 mmol), cesium carbonate (1.11 g, 3.40 mmol), tetrakis(triphenylphosphine)palladium(0) (121 mg, 0.105 mmol) and tetrahydrofuran (34 mL) were weighed into a reaction vessel in a nitrogen stream and refluxed for 20 hours. The obtained reaction solution was concentrated and dissolved by the addition of methylene chloride. Then, the solution was filtered. This filtrate was purified three times by silica gel chromatography (methylene chloride/methanol:20/1), and the eluate was evaporated to dryness. This residue was washed with methanol to obtain a metal complex represented by the formula (MC-6, 121 mg, 0.060 mmol).

ESI-MS (positive) m/z: 2036 ([M+K]$^+$)

$^1$H NMR (300 MHz, CDCl$_3$)

δ 1.20 (s, 54H), δ 7.18-7.45 (m, 33H), δ 7.87 (d, J=8.2 Hz, 3H), δ 8.30 (d, J=8.6 Hz, 3H), δ 8.38 (d, J=8.4 Hz, 12H), δ 9.25 (d, J=8.6 Hz, 3H), δ 9.39 (s, 3H)

Physical Property Measurement of Metal Complex (MC-6)

The metal complex (MC-6) was dissolved at a concentration of 2 wt % in a 10 wt % toluene solution of a polymethyl methacrylate resin (manufactured by Sigma-Aldrich, Inc.) to prepare a solution. This solution was added dropwise onto a quartz substrate and dried to form a metal complex (MC-6)-doped PMMA film on the quartz substrate. The obtained substrate was used to measure photoluminescence. As a result, light emission with a peak at 620 nm was observed. In this context, the photoluminescence was measured at an excitation wavelength of 325 nm using a PL quantum yield measurement apparatus (manufactured by Hamamatsu Photonics K.K., trade name: C9920-02).

Example 7

Synthesis of Metal Complex (MC-7)

Synthesis of 2-(4'-biphenyl)-5-bromopyridine

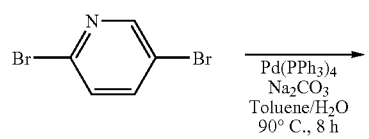

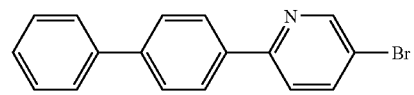

2,5-dibromopyridine (2.37 g, 10 mmol) was weighed into a reaction vessel in an argon stream and prepared into a solution by the addition of toluene (100 mL). 4-biphenylboronic acid (2.47 g, 12.5 mmol), tetrakis(triphenylphosphine)palladium(0) (0.46 g, 0.4 mmol) and a 2 M aqueous sodium carbonate solution (10 mL) were added thereto, and the mixture was stirred at 90° C. for 8 hours. From the obtained reaction mixture, the solid was collected by filtration. This solid was washed with cold toluene. This solid was dissolved in a chloroform/ethanol mixed solvent (volume ratio: 1/1) and recrystallized several times to obtain 2-(4'-biphenyl)-5-bromopyridine (1.10 g, 3.55 mmol) in a yellow solid form.

$^1$H NMR (300 MHz, CDCl$_3$)

δ 7.72-7.28 (m, 8H), δ 7.88 (d, J=10.5 Hz, 1H), δ 8.05 (d, J=6.6 Hz, 2H), δ 8.75 (s, 1H)

Synthesis of Metal Complex (Complexes 7 and 8)

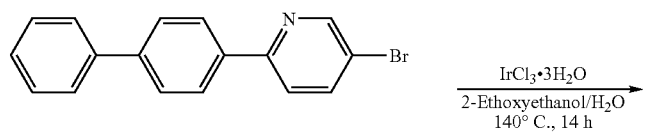

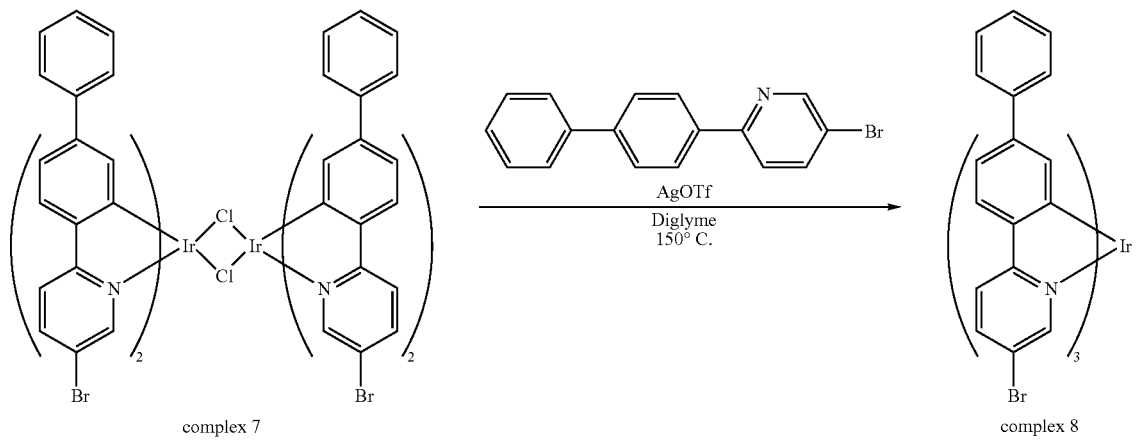

complex 7 complex 8

2-(4'-biphenyl)-5-bromopyridine (463 mg, 1.5 mmol), iridium chloride trihydrate (241 mg, 0.68 mmol), 2-ethoxyethanol (6 mL) and water (2 mL) were weighed into a reaction vessel and heated at 140° C. for 14 hours in a nitrogen stream. After air cooling, the obtained reaction mixture was filtered, and the solid was washed with methanol and hexane in this order to obtain a metal complex represented by the formula (complex 7, 539 mg, 0.32 mmol) in a yellow solid form.

The metal complex (complex 7, 539 mg, 0.32 mmol), 2-(4'-biphenyl)-5-bromopyridine (609 mg, 0.20 mmol) and diglyme (12 mL) were weighed into a reaction vessel. Silver trifluoromethanesulfonate (175 mg, 0.68 mmol) was added thereto, and the mixture was stirred at 150° C. for 11 hours. The obtained reaction mixture was filtered, and the solid was dissolved in methylene chloride. This solution was filtered, and the solvent was distilled off from the filtrate. This residue was washed with methanol and hexane in this order to obtain a metal complex represented by the formula (complex 8, 580 mg, 0.52 mmol).

Synthesis of Metal Complex (Complex 9)

The metal complex (complex 8, 580 mg, 0.52 mmol), potassium acetate (468 mg, 4.8 mmol), bis(pinacolato)diboron (538 mg, 2.1 mmol), [1,1'-bis(diphenylphosphino)ferrocene]dichloropalladium(II) (130 mg, 0.16 mmol) and tetrahydrofuran (60 mL) were weighed into a reaction vessel in a nitrogen stream and refluxed for 18 hours. The obtained reaction solution was concentrated and dissolved in methylene chloride. The solution was filtered. This filtrate was purified by silica gel chromatography (methylene chloride/methanol=20/1), and the eluate was evaporated to dryness. This residue was washed with methanol to obtain a metal complex represented by the formula (complex 9, 483 mg, 0.38 mmol).

Synthesis of Metal Complex (MC-7)

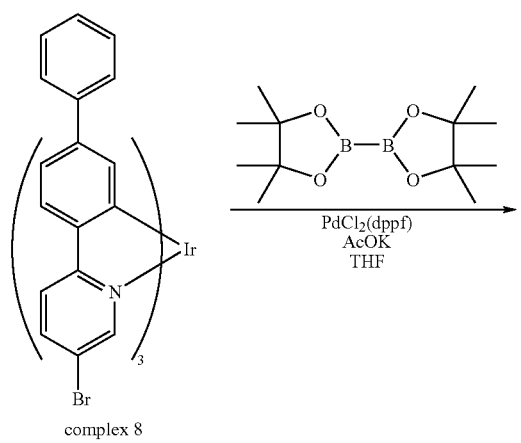

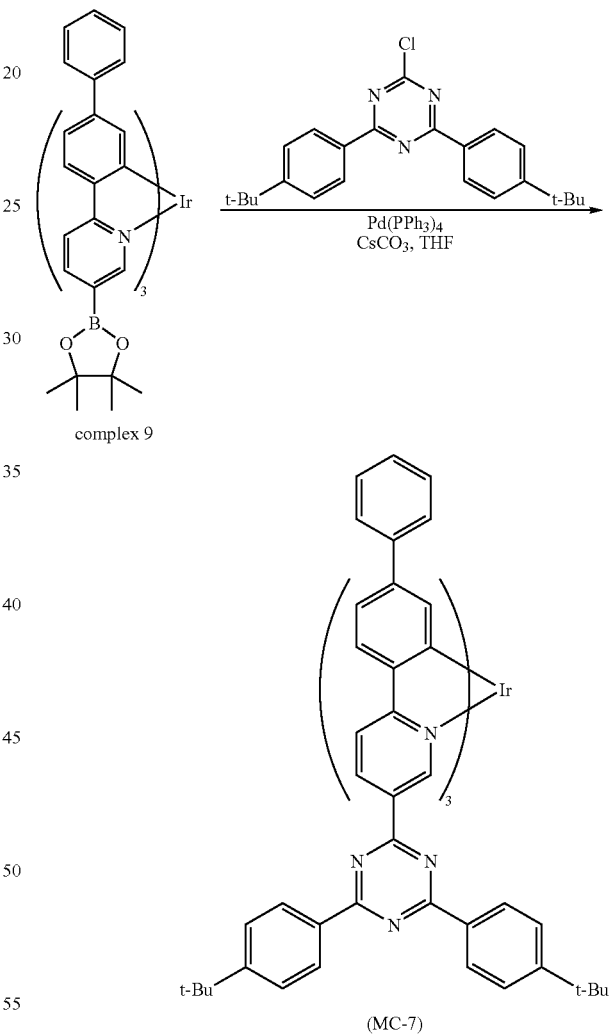

The metal complex (complex 9), 2,4-di(4'-tert-butylphenyl)-6-chloro-1,3,5-triazine, cesium carbonate, tetrakis(triphenylphosphine)palladium(0) and tetrahydrofuran are weighed into a reaction vessel in a nitrogen stream and refluxed. The obtained reaction solution is concentrated and dissolved by the addition of toluene. This solution is filtered, and the filtrate is purified by silica gel chromatography. The eluate was evaporated to dryness, and the residue is washed to obtain a metal complex represented by the formula (MC-7).

Comparative Example 1

A metal complex represented by the following formula:

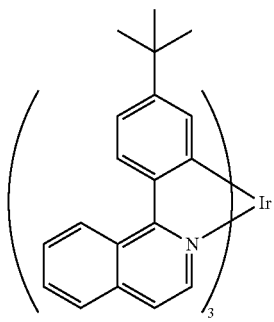

was synthesized by a method described in WO03/040256A2.

The photoluminescence quantum yield of this metal complex was measured in the same way as in Example 3. Light emission with a peak at 643 nm was observed, and the quantum yield was 51%.

Subsequently, an EL device was prepared in the same way as in Example 4 except that the metal complex represented by the formula was used instead of the metal complex (MC-4) in Example 4.

To the obtained device, a voltage was applied to obtain red EL emission with a peak at 620 nm. The luminous efficiency was 5.6 cd/A at the maximum. This device was driven for 50 hours, with initial brightness set to 4000 cd/m$^2$. As a result, the device remained at 45% brightness with respect to the initial brightness.

The invention claimed is:

1. A metal complex represented by the following formula (1):

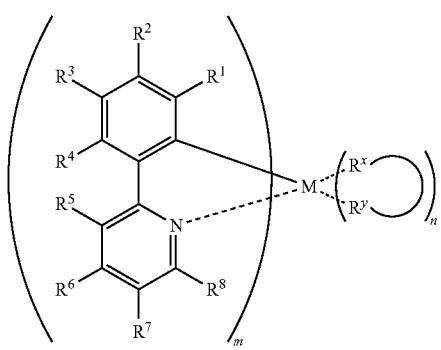

wherein M is a metal atom of iridium; $R^1$ to $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, or $R^3$ and $R^4$ or $R^5$ and $R^6$ may bond to form a ring, provided that at least one of $R^2$ and $R^7$ is a group represented by the following formula (4-7):

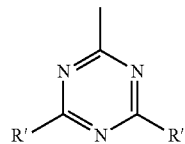

wherein each R' independently represents a $C_1$-$C_{12}$ alkoxyphenyl group or a $C_1$-$C_{12}$ alkylphenyl group, and each R' may be the same or different, and wherein m is an integer of 1 to 3, and n is an integer of 0 to 2; the moiety represented by the following formula (3):

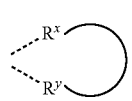

represents a monoanionic bidentate ligand; and $R^x$ and $R^y$ are an atom bonded to the metal atom M and each independently represent a carbon atom, an oxygen atom or a nitrogen atom.

2. The metal complex according to claim 1, wherein the formula (1) is represented by the following formula (1a):

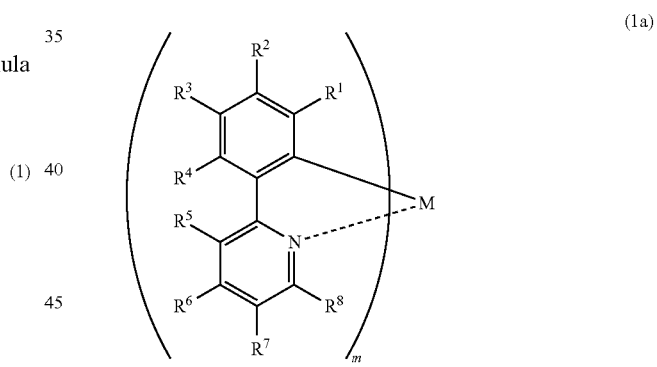

wherein M, $R^1$ to $R^8$ and m are as defined above.

3. The metal complex according to claim 1, wherein the $R^7$ is a group represented by the formula (4-7).

4. The metal complex according to claim 1, wherein the $R^2$ and the $R^7$ are each independently a group represented by the formula (4-7).

5. The metal complex according to claim 1, wherein the $R^7$ is a group represented by the formula (4-7), and the $R^2$ is a hydrogen atom.

6. The metal complex according to claim 1, wherein the metal complex exhibits phosphorescence emission with a peak wavelength of 550 nm to 800 nm in a PL emission spectrum.

7. A method for producing a metal complex according to claim 1, comprising performing a coupling reaction between a heterocyclic aromatic compound having a halogen atom or an alkyl sulfonate group and a compound represented by any of the following formulas (A-1) to (A-3):

(A-1)

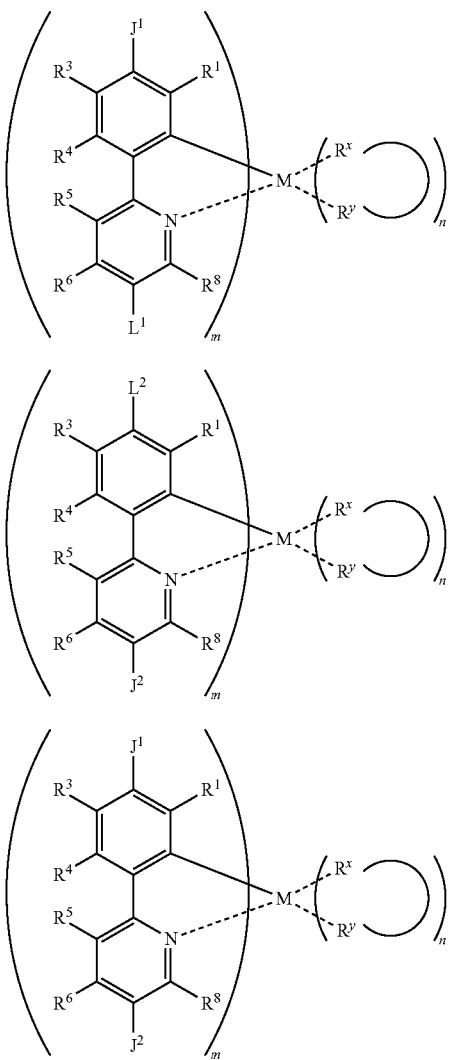

(A-2)

(A-3)

(3)

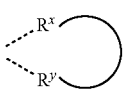

represents a monoanionic bidentate ligand; $R^x$ and $R^y$ are an atom bonded to the metal atom M and each independently represent a carbon atom, an oxygen atom or a nitrogen atom; and $J^1$ and $J^2$ are each independently a group represented by the following formulas (B-1) to (B-6):

(B-1)

(B-2)

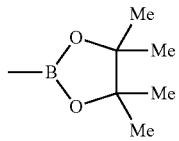

(B-3)

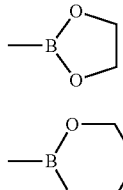

(B-4)

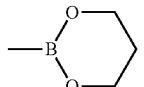

(B-5)

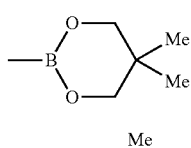

(B-6)

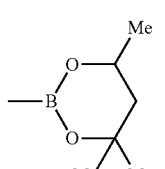

wherein the method provides for the substitution of a group of formula (4-7) for at least one of $J^1$ and $J^2$.

8. A polymer compound containing a residue of a metal complex according to claim 1.

9. The polymer compound according to claim 8, wherein the polymer compound is a conjugated polymer.

10. The polymer compound according to claim 8, wherein the polymer compound contains a group represented by the following formula (I):

—Ar—          (I)

wherein Ar represents an arylene group, a divalent heterocyclic group or a divalent aromatic amine group, and these groups may have a substituent.

11. The polymer compound according to claim 10, wherein the arylene group is a phenylene group which may have a substituent, a naphthylene group which may have a substituent, or a group represented by the following formula (3a):

(3a)

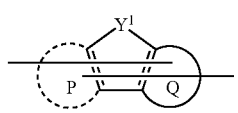

wherein M represents a metal atom of iridium; $R^1$, $R^3$, $R^4$, $R^5$, $R^6$, $R^8$, $L^1$ and $L^2$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, or $R^3$ and $R^4$ or $R^5$ and $R^6$ may bond to form a ring; m is an integer of 1 to 3, and n is an integer of 0 to 2; the moiety represented by the following formula (3):

wherein the P ring which may be absent and the Q ring each independently represent an aromatic ring, wherein two bonds are respectively present on the P ring or the Q ring in the presence of the P ring and are respectively present on a $Y^1$-containing five-membered or six-membered ring or the Q ring in the absence of the P ring; the P ring, the Q ring and the $Y^1$-containing five-membered or six-membered ring may each independently have at least one substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; $Y^1$ represents —$C(R^{11})(R^{12})$—, —$C(R^{14})(R^{15})$—$C(R^{16})(R^{17})$— or —$C(R^{32})$=$C(R^{33})$—; and $R^{11}$, $R^{12}$, $R^{14}$ to $R^{17}$, $R^{32}$ and $R^{33}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

12. The polymer compound according to claim 10, wherein the divalent heterocyclic group is a group represented by the following formula (3b):

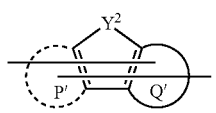

(3b)

wherein the P' ring which may be absent and the Q' ring each independently represent an aromatic ring, wherein two bonds are respectively present on the P' ring or the Q' ring in the presence of the P' ring and are respectively present on a $Y^2$-containing five-membered or six-membered ring or the Q' ring in the absence of the P' ring; the P' ring, the Q' ring and the $Y^2$-containing five-membered or six-membered ring may each independently have at least one substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; $Y^2$ represents —O—, —S—, —Se—, —$B(R^6)$—, —$Si(R^7)(R^8)$—, —$P(R^9)$—, —$PR^{10}$(=O)—, —$N(R^{13})$—, —O—$C(R^{18})(R^{19})$—, —S—$C(R^{20})(R^{21})$—, —N—$C(R^{22})(R^{23})$—, —$Si(R^{24})(R^{25})$—$C(R^{26})(R^{27})$—, —$Si(R^{28})(R^{29})$—$Si(R^{30})(R^{31})$—, —N=$C(R^{34})$— or —$Si(R^{35})$=$C(R^{36})$—; and $R^6$ to $R^{10}$, $R^{13}$, $R^{18}$ to $R^{31}$ and $R^{34}$ to $R^{36}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

13. A composition comprising a metal complex according to claim 1.

14. A liquid composition comprising a metal complex according to claim 1 and a solvent or a dispersion medium.

15. A film comprising a metal complex according to claim 1.

16. A device comprising a metal complex according to claim 1.

17. The device according to claim 16, wherein the device has electrodes comprising an anode and a cathode, and a layer disposed between the electrodes, the layer comprising the metal complex.

18. The device according to claim 16, wherein the device is a light-emitting device.

19. A planar light source which is obtained using a device according to claim 18.

20. Illumination which is obtained using a device according to claim 18.

21. A composition comprising a polymer compound according to claim 8.

22. A liquid composition comprising a polymer compound according to claim 8.

23. A film comprising a polymer compound according to claim 8.

24. A device comprising a polymer compound according to claim 8.

25. The composition according to claim 13, wherein the composition further contains a charge transport material and/or light-emitting material and wherein the charge transport material is an organic polymer compound comprising a repeating unit represented by the formula (3a) or (3b):

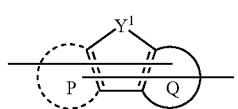

(3a)

wherein the P ring which may be absent and the Q ring each independently represent an aromatic ring, wherein two bonds are respectively present on the P ring or the Q ring in the presence of the P ring and are respectively present on a $Y^1$-containing five-membered or six-membered ring or the Q ring in the absence of the P ring; the P ring, the Q ring and the $Y^1$-containing five-membered or six-membered ring may each independently have at least one substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; $Y^1$ represents —C($R^{11}$)($R^{12}$)—, —C($R^{14}$)($R^{15}$)—C($R^{16}$)($R^{17}$)— or —C($R^{32}$)=C($R^{33}$)—; and $R^{11}$, $R^{12}$, $R^{14}$ to $R^{17}$, $R^{32}$ and $R^{33}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom;

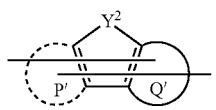

(3b)

wherein the P' ring which may be absent and the Q' ring each independently represent an aromatic ring, wherein two bonds are respectively present on the P' ring or the Q' ring in the presence of the P' ring and are respectively present on a $Y^2$-containing five-membered or six-membered ring or the Q' ring in the absence of the P' ring; the P' ring, the Q' ring and the $Y^2$-containing five-membered or six-membered ring may each independently have at least one substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group and a cyano group; $Y^2$ represents —O—, —S—, —Se—, —B($R^6$)—, —Si($R^7$)($R^8$)—, —P($R^9$), —P$R^{10}$(=O)—, —N($R^{13}$)—, —O—C($R^{18}$)($R^{19}$)—, —S—C($R^{20}$)($R^{21}$)—, —N—C($R^{22}$)($R^{23}$)—, —Si($R^{24}$)($R^{25}$)—C($R^{26}$)($R^{27}$)—, —Si($R^{28}$)($R^{29}$)—Si($R^{30}$)($R^{31}$)—, —N=C($R^{34}$)— or —Si($R^{35}$)=C($R^{36}$)—; and $R^6$ to $R^{10}$, $R^{13}$, $R^{18}$ to $R^{31}$ and $R^{34}$ to $R^{36}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

* * * * *